(12) United States Patent
Ruoslahti et al.

(10) Patent No.: US 8,912,136 B2
(45) Date of Patent: Dec. 16, 2014

(54) METHODS AND COMPOSITIONS RELATED TO CLOT-BINDING COMPOUNDS

(75) Inventors: Erkki Ruoslahti, La Jolla, CA (US); Lilach Agemy, La Jolla, CA (US); Venkata Ramana Kotamraju, Goleta, CA (US)

(73) Assignee: Sanford-Burnham Medical Research Institute, LaJolla, CA (US)

( * ) Notice: Subject to any disclaimer, the term of this patent is extended or adjusted under 35 U.S.C. 154(b) by 769 days.

(21) Appl. No.: 12/973,459

(22) Filed: Dec. 20, 2010

(65) Prior Publication Data
US 2011/0165064 A1 Jul. 7, 2011

Related U.S. Application Data

(60) Provisional application No. 61/288,083, filed on Dec. 18, 2009.

(51) Int. Cl.
| | |
|---|---|
| A61K 38/00 | (2006.01) |
| C07K 14/755 | (2006.01) |
| C07K 7/06 | (2006.01) |
| A61K 45/06 | (2006.01) |
| A61K 38/06 | (2006.01) |
| A61K 9/127 | (2006.01) |
| A61K 38/08 | (2006.01) |
| A61K 9/16 | (2006.01) |

(52) U.S. Cl.
CPC ............... *A61K 9/1272* (2013.01); *A61K 45/06* (2013.01); *A61K 38/06* (2013.01); *A61K 38/08* (2013.01); *A61K 9/1641* (2013.01)
USPC .......... 514/1.1; 514/13.7; 514/19.2; 514/21.8

(58) Field of Classification Search
None
See application file for complete search history.

(56) References Cited

U.S. PATENT DOCUMENTS

| | | | |
|---|---|---|---|
| 5,792,742 | A | 8/1998 | Gold |
| 5,897,945 | A | 4/1999 | Lieber |
| 6,759,199 | B2 | 7/2004 | Mirkin |
| 2005/0048063 | A1 | 3/2005 | Ruoslahti |
| 2008/0305101 | A1 | 12/2008 | Ruoslahti |
| 2009/0036349 | A1 | 2/2009 | Ruoslahti |

FOREIGN PATENT DOCUMENTS

| | | |
|---|---|---|
| WO | 9633171 | 10/1996 |
| WO | 2005016919 | 2/2005 |
| WO | 2005039495 | 5/2005 |
| WO | 2007108749 | 9/2007 |
| WO | 2008057282 | 5/2008 |

OTHER PUBLICATIONS

Simberg et al. PNAS vol. 104, No. 3, 2007, pp. 932-936.*
Bedford et al. Molecular Cell , n 2009, pp. 1-13.*
Pilch et al. PNAS vol. 103, No. 8, 2006, pp. 2800-2804.*
Abe, et al., "Regulation of vascular endothelial growth factor production and angiogenesis by the cytoplasmic tail of tissue factor", PNAS, 96:8663-8668 (1999).
Agemy, et al., "Nanoparticle-induced cascular blockade in human prostrate cancer", Blood, 116(15):2847-56 (2010).
Akerman, et al., "Nanocrystal targeting in vivo", PNAS, 99:12617-12621 (2002).
Beecken,et al., "Effect of antiangiogenic therapy on slowly growing, poorly vascularized tumors in mice", J. Natl. Cancer Inst., 93(5):382-87 (2001).
Bieker, et al., "Infarction of tumor vessels by NGR-peptide-directed targeting of tissue factor: experimental results and first-in-man experience", Blood, 113 (20):5019-27 2009.
Boccaccio, et al., "The MET oncogene drives a genetic programme linking cancer to haemostasis", Nature, 434:396-400 (2005).
Bode, et al., "Antibody-directed fibrinolysis. An antibody specific for both fibrin and tissue plasminogen activator", J. Biol. Chem., 264(2):944-948 (1989).
Boucher, et al., "Interstitial pressure gradients in tissue-isolated and subcutaneous tumors: implications for therapy", Cancer Res, 50:4478-4484 (1990).
Cai,et al, "Peptide-labeled near-infrared quantum dots for imaging tumor vasculature in living subjects", Nano Lett., 6:669-676 (2006).
Callow, et al, "Thermodynamic modeling and cryomicroscopy of cell-size, unilamellar, and paucilamellar liposomes", Cryobiology, 22(3):251-267 (1985).
Carmeliet, et al., "Transgenic mouse models in angiogenesis and cardiovascular disease", J. Pathol., 190(3):387-405 (2000).
Chatterjee, et al., "Upconversion fluorescence imaging of cells and small animals using lanthanide doped nanocrystals" , Biomaterials, 29(7):937-43 (2008).
DeNardo, et al., "Development of tumor targeting bioprobes ((111)In-chimeric L6 monoclonal antibody nanoparticles) for alternating magnetic field cancer therapy", Clin Cancer Res 11:7087s-7092s (2005).
Desai, et al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 12:1317-1324 (2006).
Dvorak, et al., "Regulation of extravascular coagulation by microvascular permeability", Science 227:1059-1061 (1985).
El-Sheikh, et al., "A selective tumor microvasculature thrombogen that targets a novel receptor complex in the tumor angiogenic microenvironment", Cancer Res, 65:11109-11117 (2005).
Fernandez-Urrusuno, et al., "Effect of polymeric nanoparticle administration on the clearance activity of the mononuclear phagocyte system in mice", J Biomed Mater Res, 31:401-408 (1996).
Ferrara, "Role of vascular endothelial growth factor in the regulation of angiogenesis", Kidney Int, 56(3):794-814 (1999).

(Continued)

*Primary Examiner* — James H Alstrum Acevedo
*Assistant Examiner* — Li Lee
(74) *Attorney, Agent, or Firm* — Jenkins, Wilson, Taylor & Hunt, P.A.

(57) ABSTRACT

Disclosed are compositions and methods related to clot-binding compounds. For example, disclosed are compositions comprising a surface molecule and at least one modified clot-binding compound. The modified clot-binding compound can selectively bind to clotted plasma protein, wherein the composition causes clotting and amplifies the accumulation of the composition in tumors. The modified clot-binding compound can enhance the clotting in tumors compared to its unmodified derivative. The disclosed targeting is useful for treatment of cancer and other diseases and disorders.

56 Claims, 31 Drawing Sheets

(56) References Cited

OTHER PUBLICATIONS

Fitzpatrick and Garnett, "Design, synthesis and in vitro testing of methotrexate carrier conjugates linked via oligopeptide spacers", Anticancer Drug Des., 10:1-9 (1995).
Folkman, "Angiogenesis inhibitors generated by tumors", Mol. Med., 1 (2):120-22 (1995).
Folkman, "Angiogenesis: an organizing principle for drug discovery", Natl. Rev.Drug Discov., 6(4):273-86 (2007).
Gao, et al., "Quantum-dot nanocrystals for ultrasensitive biological labeling and multicolor optical encoding", J. Biomed. Opt., 7:532-7 (2002).
Gorbet and Sefton, "Biomaterial-associated thrombosis: roles of coagulation factors, complement, platelets and leukocytes", Biomaterials, 25:5681-5703 (2004).
Han, et al., "Quantum-dot-tagged microbeads for multiplexed optical coding of biomolecules", Nature Biotechnology,19:631-35 (2001).
Hoffman, et al., "Progressive vascular changes in a transgenic mouse model of squamous cell carcinoma", Cancer Cell, 4:383-391 (2003).
Hoffman, "Imaging tumor angiogenesis with fluorescent proteins", APMIS, 112 (7-8):441-49 (2004).
Holvoet, et al., "Thrombolytic profiles of clot-targeted plasminogen activators. Parameters determining potency and initial and maximal rates", Circulation, 87:1007-1016 (1993).
Huang, et al., "Tumor infarction in mice by antibody-directed targeting of tissue factor to tumor vasculature", Science, 275: 547-550 (1997).
Hutchinson and Muller, "Transgenic mouse models of human breast cancer", Oncogene, 19:6130-6137 (2000).
Jain,et al., "Angiogenesis and lymphangiogenesis in tumors: insights from intravital microscopy",Cold. Spring Harb Symp Quant Bio., 67:239-48 (2002).
Järvinen, et al., "Molecular changes in the vasculature of injured tissues", Am. J. Pathol., 171(2):702-11 (2007).
Jemal, et al., "Cancer statistics, 2008", CA Cancer J. Clin, 58(2):71-96 ( 2008).
Jung and Jacobs, "Physical and chemical properties of superparamagnetic iron oxide MR contrast agents: ferumoxides, ferumoxtran, ferumoxsil", Magn Reson Imaging, 13:661-674 (1995).
Jung, "Surface properties of superparamagnetic iron oxide MR contrast agents: ferumoxides, ferumoxtran, ferumoxsil", Magn Reson Imaging, 13:675-691 (1995).
Karmali, et al., "Targeting of albumin-embedded paclitaxel nanoparticles to tumors", Nanomedicine, 5(1):73-82 (2009).
Kessler, et al., "Inhibition of tumor growth by RGD peptide-directed delivery of truncated tissue factor to the tumor vasculature", Clinic. Cancer Res., 11 (17):6317-24 (2005).
Khandoga, et al., "Ultrafine particles exert prothrombotic but not inflammatory effects on the hepatic microcirculation in healthy mice in vivo", Circulation, 109:1320-1325 (2004).
Kim, et al., "Preparation of multivesicular liposomes", Biochim et Biophys Acta, 728:339-348 (1983).
Lin, et al., "Photonic pseudo-gap-based modification of photoluminescence from CdS nanocrystal satellites around polymer microspheres in a photonic crystal", Appl. Phys Lett., 81:3134 (2002).
MacIntosh, et al., "Precise microdissection of human prostate cancers reveals genotypic heterogeneity", Cancer Res., 58(1):23-28 (1998).
Miller, et al., "Morphology of prostate cancer: the effects of multifocality on histological grade, tumor volume and capsule penetration", J Urol., 152 (5pt2):17409-13 (1994).
Moghimi, et al., "Long-circulating and target-specific nanoparticles: theory to practice", Pharmacol Rev 53:283-318 (2001).
Moore, et al., "Uptake of dextran-coated monocrystalline iron oxides in tumor cells and macrophages", J Magn Reson Imaging 7:1140-1145 (1997).
Nilsson, et al., "Targeted delivery of tissue factor to the ED-B domain of fibronectin, a marker of angiogenesis, mediates the infarction of solid tumors in mice", Cancer Res., 61 (2):711-16 (2001).
Oh, et al., "Subtractive proteomic mapping of the endothelial surface in lung and solid tumours for tissue-specific therapy", Nature, 429:629-635 (2004).
Pai, et al.,"Microscopic flow visualization system for fluids in magnetic field", J. of Mag. & Magnetic Mater.,194:262-66 (1999).
Park, et al., "Systematic Surface Engineering of Magnetic Nanoworms for in vivo Tumor Targeting", Small, 5(6):694-700 (2009).
Pasqualini and Ruoslahti, "Organ targeting in vivo using phage display peptide libraries", Nature, 380:364-366 (1996).
Peters, et al., "Targeting atherosclerosis by using modular, multifunctional micelles", PNAS, 106:9815-19 (2009).
Pilch, et al., "Peptides selected for binding to clotted plasma accumulate in tumor stroma and wounds", PNAS, 103: 2800-2804 (2006).
Radomski, et al., "Nanoparticle-induced platelet aggregation and vascular thrombosis", Br J Pharmacol, 146:882-93 (2005).
Ran, et al., "Infarction of solid Hodgkin's tumors in mice by antibody-directed targeting of tissue factor to tumor vasculature", Cancer Res., 58(20):4646-53 (1998).
Ruijter, et al., "Metastasising sarcoma of the aorta", Histopathology, 29 (3):278-81 (1996).
Ruoslahti, et al., "Targeting of drugs and nanoparticles to tumors", J. Cell Biol., 188(6):759-68 (2010).
Ruoslahti, "Specialization of tumour vasculature", Nat Rev Cancer 2:83-90 (2002).
Simberg, et al., "Biomimetic amplification of nanoparticle homing to tumors", PNA, 104: 932-936 (2007).
Sinek, et al., "Two-dimensional chemotherapy simulations demonstrate fundamental transport and tumor response limitations involving nanoparticles", Biomed Microdevices, 6:297-309 (2004).
Souhami, et sal., "The effect of reticuloendothelial blockade on the blood clearance and tissue distribution of liposomes", Biochim Biophys Acta, 674: 354-371 (1981).
Sugahara, et al., "Tissue-penetrating delivery of compounds and nanoparticles into tumors", Cancer Cell, 16(6):510-20 (2009).
Thorek, et al., "Superparamagnetic iron oxide nanoparticle probes for molecular imaging", Ann. Biomed. Eng., 34(1):23-38 (2006).
van der Heyde, et al., "Platelet depletion by anti-CD41 (alphaIIb) mAb Injection early but not late in the course of disease protects against *Plasmodium berghei* pathogenesis by altering the levels of pathogenic cytokines", Blood, 105: 1956-1963 (2005).
van Rooijen and Sanders, "Liposome mediated depletion of macrophages: mechanism of action, preparation of liposomes and applications", J Immunol Methods, 174: 83-93 (1994).
Wang, et al., "Composite Photonic Crystals from Semiconductor Nanocrystal/ Polyelectrolyte-Coated Colloidal Spheres", Chem. Mater., 15:2724-29 (2003).
Weissleder, et al., "Long-circulating iron oxides for MR imaging", Advanced Drug Delivery Reviews, 16:321-334 (1995).
Weissleder, et al., "Superparamagnetic iron oxide: pharmacokinetics and toxicity", AJR Am J Roentgenol, 152:167-173 (1989).
Weissleder, "Scaling down imaging: molecular mapping of cancer in mice", Natl. Review Cancer, 2(1)11-18 (2002).
Zanuy, et al., "In silica molecular engineering for a targeted replacement in a tumor-homing peptide", J Phys Chem B., 113(22):7879-89 (2009).

* cited by examiner

CREKA-SPIO DAPI

*FIG. 1A*  *FIG. 1B* tumor  liver  spleen

Antibody  CREKA-SPIO  DAPI+ merge

Fibrin(ogen)     CREKA-SPIO     DAPI+merge

Fibrin(ogen)     CREKA-SPIO     DAPI+merge

Platelets   CREKA-SPIO   merge

CRKDKC +
CR(NME)EKA-NW

CRKDKC-NW

CR(NMe)KA-SPIO    Control

CR(NMe)KA+CRK-SPIO    Control

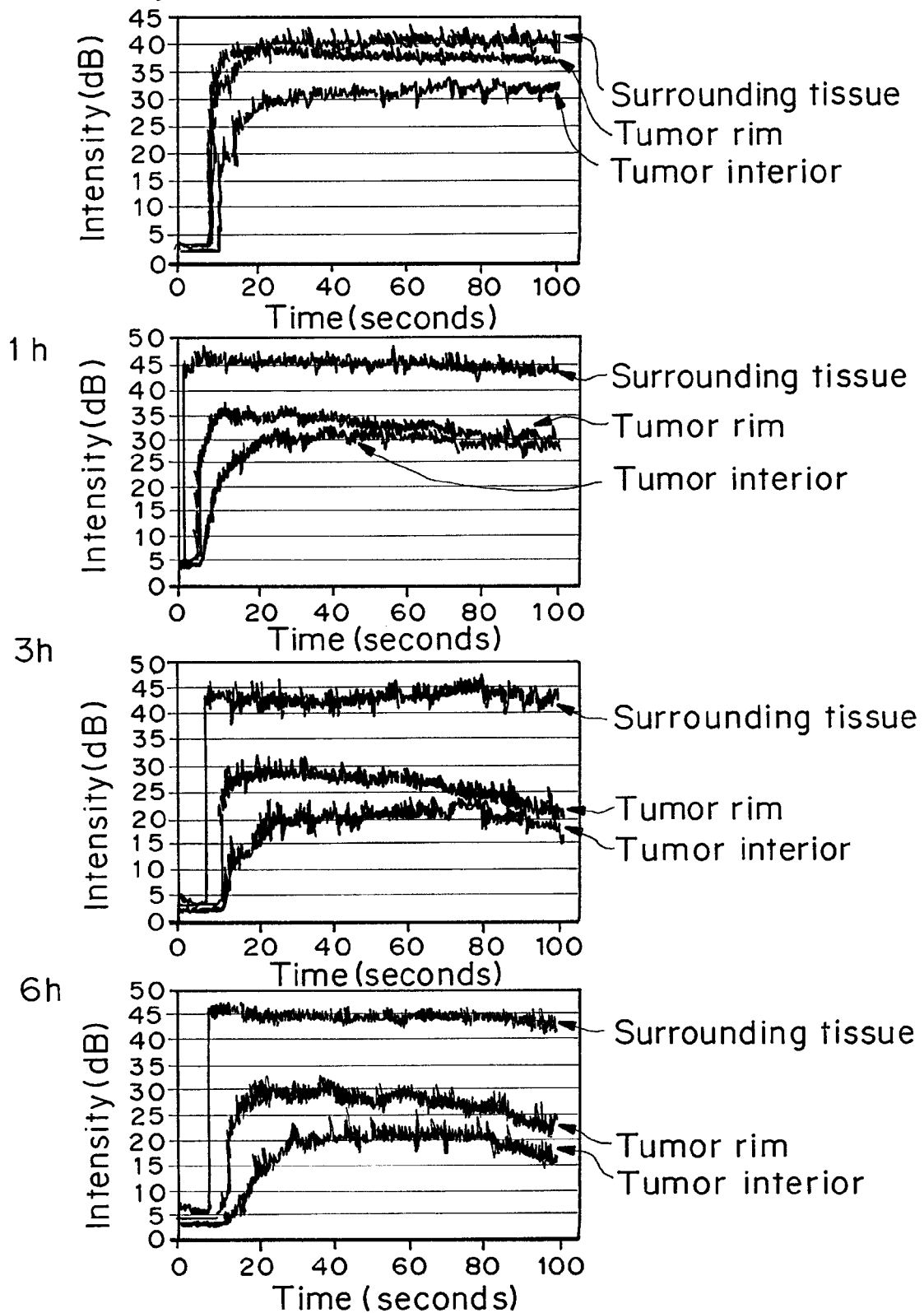

METHODS AND COMPOSITIONS RELATED TO CLOT-BINDING COMPOUNDS

CROSS-REFERENCE TO RELATED APPLICATIONS

This application claims benefit of U.S. Provisional Application No. 61/288,083, filed Dec. 18, 2009. Application No. 61/288,083, filed Dec. 18, 2009, is hereby incorporated herein by reference in its entirety.

STATEMENT REGARDING FEDERALLY SPONSORED RESEARCH

This invention was made with government support under grants P01-CA104898, P01-CA-124427, and P01-CA119335 awarded by the National Institutes of Health (NIH), grant HL070818 awarded by the National Heart, Lung and Blood Institute, grant 1S10RR017753 awarded by the National Center for Research Resources, and DMR05-20415 award by the National Science Foundation. The government has certain rights in this invention.

REFERENCE TO SEQUENCE LISTING

The Sequence Listing submitted Dec. 20, 2010 as a text file named "SBMRI_45_8402_AMD_AFD_Sequence_Listing_Text.txt," created on Dec. 6, 2010, and having a size of 3,481 bytes is hereby incorporated by reference pursuant to 37 C.F.R. §1.52(e)(5).

FIELD OF THE INVENTION

The present invention relates generally to the fields of molecular medicine, cancer biology, and cardiovascular disease, and, more specifically, to clot-binding compounds that selectively home to tumor vasculature and atherosclerotic plaques.

BACKGROUND OF THE INVENTION

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life.

Nanomedicine is an emerging field that uses nanoparticles to facilitate the diagnosis and treatment of diseases. Notable early successes in the clinic include the use of superparamagnetic nanoparticles as a contrast agent in MRI and nanoparticle-based treatment systems (Desai 2006; Weissleder 1995). The first generation of nanoparticles used in tumor treatments rely on "leakiness" of tumor vessels for preferential accumulation in tumors; however, this enhanced permeability and retention (EPR) is not a constant feature of tumor vessels (Sinek 2004) and even when present, still leaves the nanoparticles to negotiate the high interstitial fluid pressure in tumors (Sinek 2004; Boucher 1990). An attractive alternative is to target nanoparticles to specific molecular receptors in the blood vessels because they are readily available for binding from the blood stream and because tumor vessels express a wealth of molecules that are not significantly expressed in the vessels of normal tissues (Hoffman 2003; Oh 2004; Ruoslahti 2002).

Specific targeting of nanoparticles to tumors has been accomplished in various experimental systems (DeNardo 2005; Akerman 2002; Cai 2006), but the efficiency of delivery is generally low. In nature, amplified homing is an important mechanism ensuring sufficient platelet accumulation at sites of vascular injury. It involves target binding, activation, platelet-platelet binding, and formation of a blood clot. What is needed in the art is a nanoparticle delivery system in which the particles amplify their own homing.

BRIEF SUMMARY OF THE INVENTION

Disclosed are compositions comprising a surface molecule and at least one modified clot-binding compound. The modified clot-binding compound can selectively bind to clotted plasma protein, wherein the composition causes clotting and amplifies the accumulation of the composition in tumors. The modified clot-binding compound can enhance the clotting in tumors compared to its unmodified derivative.

Also disclosed are methods comprising administering to a subject any of the disclosed compositions. The composition selectively homes to clotted plasma protein, wherein the composition causes clotting and amplifies the accumulation of the composition at the site of the clotted plasma protein.

Also disclosed are methods comprising administering to a subject a plurality of different of the disclosed compositions. In some forms, each of the plurality of different compositions comprises a surface molecule and at least one modified clot-binding compound. In some forms, at least one of the plurality of different compositions comprises a surface molecule and at least one modified clot-binding compound. In some forms, each of the plurality of different compositions selectively homes to clotted plasma protein. In some forms, at least one of the plurality of compositions selectively homes to clotted plasma protein. In some forms, each of the compositions causes clotting and amplifies the accumulation of the composition at the site of the clotted plasma protein. In some forms, at least one of the compositions causes clotting and amplifies the accumulation of the composition at the site of the clotted plasma protein.

The modified clot-binding compound can comprise a methylated clot-binding compound. The methylated clot-binding compound can comprise a methylated amino acid segment. The methylated amino acid segment can be selected from amino acid segments comprising a methylated derivative of amino acid sequence CREKA (SEQ ID NO: 1) or a conservative variant thereof, amino acid segments comprising a methylated derivative of amino acid sequence CREKA (SEQ ID NO:1), amino acid segments consisting of a methylated derivative of amino acid sequence CREKA (SEQ ID NO:1), and amino acid segments consisting of a methylated derivative amino acid sequence REK. The methylated amino acid segment can comprise a methylated derivative of amino acid sequence CREKA (SEQ ID NO: 1) or a conservative variant thereof. The methylated amino acid segment can comprise a methylated derivative of amino acid sequence CREKA (SEQ ID NO:1). The methylated amino acid segment can consist of a methylated derivative of amino acid sequence CREKA (SEQ ID NO:1). The methylated amino acid segment can consist of a methylated derivative of amino acid sequence REK.

The amino acid sequence can be N- or C-methylated in at least one position. The amino acid sequence can be C(NMe) REKA (SEQ ID NO:8), CR(NMe)EKA (SEQ ID NO:9), CR(CMe)EKA (SEQ ID NO:10), CRE(NMe)KA (SEQ ID NO:11), CRE(CMe)KA (SEQ ID NO:12), or CR(NMe)E (NMe)KA (SEQ ID NO:13). The amino acid sequence can be CR(NMe)EKA (SEQ ID NO:9), CRE(CMe)KA (SEQ ID NO:11), or CR(NMe)E(NMe)KA (SEQ ID NO:13).

The composition can further comprise a plurality of clot-binding compounds, wherein the clot-binding compounds selectively bind to clotted plasma protein, wherein the plurality of clot-binding compounds causes clotting and amplifies the accumulation of the composition in tumors. The plurality of clot-binding compounds can each and/or collectively selectively bind to clotted plasma protein. For example, some or all of the plurality of clot-binding compounds can selectively bind to clotted plasma protein. One or more of the plurality of clot-binding compounds can be modified clot-binding compounds, wherein the modified clot-binding compounds enhance the clotting in tumors compared to their unmodified derivatives. One or more of the modified clot-binding compounds of the plurality of clot-binding compounds can comprise a methylated clot-binding compound. One or more of the methylated clot-binding compounds of the plurality of clot-binding compounds can comprise a methylated amino acid segment.

Each of the methylated amino acid segments of the plurality of clot-binding compounds can be independently selected from amino acid segments comprising a methylated derivative of amino acid sequence CREKA (SEQ ID NO: 1) or a conservative variant thereof, amino acid segments comprising a methylated derivative of amino acid sequence CREKA (SEQ ID NO:1), amino acid segments consisting of a methylated derivative of amino acid sequence CREKA (SEQ ID NO:1), and amino acid segments consisting of a methylated derivative amino acid sequence REK. The methylated amino acid segments of the plurality of clot-binding compounds can each independently comprise a methylated derivative of amino acid sequence CREKA (SEQ ID NO: 1) or a conservative variant thereof. The methylated amino acid segments of the plurality of clot-binding compounds can each independently comprise a methylated derivative of amino acid sequence CREKA (SEQ ID NO:1). The methylated amino acid segments of the plurality of clot-binding compounds can each independently consist of a methylated derivative of amino acid sequence CREKA (SEQ ID NO:1). The methylated amino acid segments can each independently consist of a methylated derivative of amino acid sequence REK.

The methylated amino acid segments of the plurality of clot-binding compounds can each comprise a methylated derivative of amino acid sequence CREKA (SEQ ID NO: 1) or a conservative variant thereof. The methylated amino acid segments of the plurality of clot-binding compounds can each comprise a methylated derivative of amino acid sequence CREKA (SEQ ID NO:1). The methylated amino acid segments of the plurality of clot-binding compounds can each consist of a methylated derivative of amino acid sequence CREKA (SEQ ID NO:1). The methylated amino acid segments of the plurality of clot-binding compounds can each consist of a methylated derivative of amino acid sequence REK.

In some forms, the surface molecule can be thrombogenic. In some forms, the modified clot-binding compound can be thrombogenic.

The composition can further comprising one or more tumor-homing compounds. One or more of the tumor-homing compounds can comprise an amino acid segment. One or more of the amino acid segments of the tumor-homing compounds can comprise the amino acid sequence CRKDKC (SEQ ID NO:5) or a conservative derivative thereof or the amino acid sequence CGKRK (SEQ ID NO:7) or a conservative derivative thereof. One or more of the tumor-homing compounds can be thrombogenic.

The composition can bind inside tumor blood vessels. The composition can reduce tumor growth. The surface molecule can comprise an iron oxide nanoworm. The surface molecule can comprise an iron oxide nanoparticle. The surface molecule can comprise an albumin nanoparticle. The surface molecule can comprise a liposome. The surface molecule can comprise a microparticle. The surface molecule can comprise a fluorocarbon microbubble.

The composition can comprise at least 100 clot-binding compounds. The composition can comprise at least 1000 clot-binding compounds. The composition can comprise at least 10,000 clot-binding compounds.

The composition can further comprise one or more moieties. The moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, an image contrast agent, a fluorophore, fluorescein, rhodamine, a radionuclide, indium-111, technetium-99, carbon-11, and carbon-13. At least one of the moieties can be a therapeutic agent. The therapeutic agent can comprise a compound or composition for treating cancer. The therapeutic agent can comprise a compound or composition to induce programmed cell death or apoptosis. The therapeutic agent can be Abraxane. The therapeutic agent can be paclitaxel. The therapeutic agent can be taxol. In some forms, at least one of the moieties can be thrombogenic. In some forms, at least one of the moieties can not a clot-binding compound. In some forms, none of the moieties are clot-binding compounds. In some forms, at least one of the moieties is a homing compound, wherein the homing compound is not a clot-binding compound. At least one of the moieties can be a detectable agent. The detectable agent can be FAM.

The composition can selectively homes to tumor vasculature, wound sites, or both. The composition can have a therapeutic effect. The therapeutic effect can be a slowing in the increase of or a reduction of tumor burden. The therapeutic effect can be a slowing of the increase of or reduction of tumor size. The therapeutic effect can be a reduction or blocking of blood circulation in a tumor. The therapeutic effect can be a reduction or cessation of bleeding at a wound site. The therapeutic effect can be a decrease in the time for bleeding to stop at a wound site. The therapeutic effect can comprise a reduction in inflammation, an increase in speed of wound healing, reduction in amounts of scar tissue, decrease in pain, decrease in swelling, decrease in necrosis, or a combination.

The clotting can have a therapeutic effect. The subject can have one or more sites to be targeted, wherein the composition homes to one or more of the sites to be targeted. The subject can have a tumor, wherein the composition has a therapeutic effect on the tumor.

In some forms, the composition can comprise a sufficient number and composition of clot-binding compounds such that the composition causes clotting and amplifies the accumulation of the composition in tumors. Sufficiency of the number and composition of clot-binding compounds (modified or otherwise) can be determined by assessing clotting and amplification of the accumulation of the composition in tumors in a non-human animal.

The composition can comprise a sufficient density and composition of clot-binding compounds such that the composition causes clotting and amplifies the accumulation of the composition in tumors. Sufficiency of the density and composition of clot-binding compounds can be determined by assessing clotting and amplification of the accumulation of the composition in tumors in a non-human animal.

A plurality of the clot-binding compounds can each be independently selected from an amino acid segment comprising the amino acid sequence REK, a fibrin-binding peptide, a clot-binding antibody, and a clot-binding small organic molecule. A plurality of the clot-binding compounds can each independently comprise an amino acid segment comprising the amino acid sequence REK. Modified clot-binding compounds can be independently selected from an amino acid segment comprising a modified form of the amino acid sequence REK, a modified form of a fibrin-binding peptide, a modified form of a clot-binding antibody, and a modified form of a clot-binding small organic molecule. The modified clot-binding compounds can each independently comprise an amino acid segment comprising a modified form of the amino acid sequence REK. A particularly useful modification is methylation.

The amino acid segments of clot-binding compounds can each be independently selected from amino acid segments comprising the amino acid sequence CREKA (SEQ ID NO: 1) or a conservative variant thereof, amino acid segments comprising the amino acid sequence CREKA (SEQ ID NO:1), amino acid segments consisting of the amino acid sequence CREKA (SEQ ID NO:1), and amino acid segments consisting of the amino acid sequence REK. The amino acid segments can each independently comprise the amino acid sequence CREKA (SEQ ID NO: 1) or a conservative variant thereof. The amino acid segments can also each independently comprise the amino acid sequence CREKA (SEQ ID NO:1). The amino acid segment can also consist of the amino acid sequence CREKA (SEQ ID NO:1). The amino acid segment can consist of the amino acid sequence REK.

A plurality of the clot-binding compounds can each comprise a fibrin-binding peptide. The fibrin-binding peptides can independently be selected from the group consisting of fibrin binding proteins and fibrin-binding derivatives thereof. In another example, a plurality of the clot-binding compounds can each comprise a clot-binding antibody. Furthermore, a plurality of the clot-binding compounds can each comprise a clot-binding small organic molecule.

In some forms, each of the at least one of the plurality of different compositions selectively homes to clotted plasma protein, wherein each of the at least one of the plurality of compositions causes clotting and amplifies the accumulation of the compositions at the site of the clotted plasma protein. In some forms, at least one of the plurality of different compositions comprises a surface molecule and at least one unmodified clot-binding compound, wherein the unmodified clot-binding compound selectively binds to clotted plasma protein. In some forms, at least one of the plurality of different compositions comprises a surface molecule and at least one homing compound, wherein the homing compound is not a clot-binding compound. In some forms, the homing compound can selectively bind to tumor vasculature. In some forms, the homing compound can be a tumor-homing compound. In some forms, the tumor-homing compound can comprises an amino acid segment. In some forms, the amino acid segment of the tumor-homing compound can comprise the amino acid sequence CRKDKC (SEQ ID NO:5) or a conservative derivative thereof, or the amino acid sequence CGKRK (SEQ ID NO:7) or a conservative derivative thereof. In some forms, at least two of the plurality of different compositions can differ in the homing compounds of which the compositions are comprised. In some forms, at least two of the plurality of different compositions can differ in the clot-binding compounds of which the compositions are comprised.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A-1D show tumor homing of CREKA pentapeptide. Fluorescein-conjugated CREKA peptide (200 μg per mouse) was injected into mice bearing syngeneic B16 melanoma tumors. Representative microscopic fields are shown to illustrate homing of fluorescein-CREKA to fibrin-like structures in tumors in wild type mice (A, arrow) and lack of homing in fibrinogen null mice (B). (C) The CREKA phage binds to clotted plasma proteins in the tube, while non-recombinant control phage shows little binding. (D) Dextran-coated iron oxide nanoparticles conjugated with fluorescein-CREKA bind to clotted plasma proteins, and the binding is inhibited by free CREKA peptide. The inset in (D) shows the microscopic appearance of the clot-bound CREKA-SPIO. Magnification: A-B, 200×; D, 600×.

FIGS. 3A, 3B and 3C show the accumulation of CREKA-SPIO nanoparticles in tumor vessels. Mice bearing MDA-MB-435 xenografts were injected with Ni-liposomes and CREKA-SPIO nanoparticles as described in the legend to FIG. 2. The mice were perfused 6 hours after the nanoparticle injection and tissues were collected. (A) Upper panels: Co-localization (*) of nanoparticle fluorescence with CD31 staining in blood vessels; Middle panels: Co-localization (*) of nanoparticle fluorescence and anti-fibrin(ogen) staining in tumor blood vessels. Inset—an image showing CREKA-SPIO distributed along fibrils in a tumor blood vessel; Lower panels: Lack of co-localization of nanoparticle fluorescence with anti-CD41 staining for platelets. (B) Intravital confocal microscopy of tumors using DiI-stained red blood cells as a marker of blood flow. The arrow points to a vessel in which stationary erythrocytes indicate obstruction of blood flow. Blood flow in the vessel above is not obstructed. Six successive frames from a 1-min movie (Movie 2 in Supplementary Material) are shown. (C) CREKA-coated liposomes co-localize with fibrin in tumor vessels. The results are representative of 3 independent experiments. Magnification: A and C, 600×, B, 200×.

FIG. 10A: Quantification of fluorescence with Image J software. Several N/C-methylated CREKA analogs produced stronger fluorescence than unmodified CREKA. Error bars show mean±SEM (n=3-4). FIG. 10B: Representative images from mice injected with CREKA, CR(NMe)EKA or C(NMe)REKA peptide. Dotted lines show where the organs were placed, and a line outlines the tumor. The middle and right panels show confocal images from mice injected with the indicated peptides. FAM-labeled CREKA peptide in which the glutamic acid is N-methylated accumulates in tumor tissue more strongly than unmodified CREKA. Nuclei were stained with DAPI, and blood vessels were visualized with CD31 staining. Magnification×200.

FIG. 12A: Iron oxide nanoworms coated with FAM-labeled CRKDKC or CGKRK were intravenously injected into nude mice bearing 22Rv-1 orthotopic human prostate cancer tumors. Tumors were harvested 5 hrs later, and tumor sections were stained with anti-CD-31 and examined by confocal microscopy. FIG. 12B: A mixture of nanoworms coated with FAM-labeled CRKDKC peptide (light gray) and rhodamine-labeled CREKA peptide (gray) was intravenously injected (2.5 mg Fe/kg of each nanoworm preparation) into nude mice bearing 22Rv-1 tumors, and tissues were harvested 5 hrs later. Tumor sections were stained with anti-CD-31 and anti-fibrino(gen), and examined by confocal microscopy. The magnification is ×100 (or 400×). Nuclei were stained with DAPI. FIG. 12C: Cryosections of 22Rv-1 orthotopic tumor from mice injected with PBS, or nanoworms coated with CREKA or CR(NMe)EKA, or a mixture of CRKDKC and CREKA nanoworms were immunohistochemically stained with an anti-fibrino(gen) antibody (dark shaded areas). The sample were subjected to image analysis with Scanscope to quantify fibrino(gen)-positive areas. The insets show examples of the positive staining.

FIG. 13A: T2-weighted MR images. A mixture of equal proportions of CRKDKC-coated and CR(NMe)EKA-coated nanoworms (total dose 5 mg/kg) were intravenously injected into tumor-bearing mice. The particles were allowed to circulate for the indicated period of time. Gray scales and pseudo-colored images of axial plains through the tumors are shown. Gadolinium (Gd) and Feridex (Fe) were used as reference standards. The nanoworms highlight the blood vessels in the tumors. FIG. 13B: Histograms showing the quantitative changes in tumor iron content at different time points. Only the targeted nanoworms show significant accumulation in the tumors with time. Note that the scale is different in panels 1 and 2.

FIG. 14A: Tumor volume one day after the last injection. Similar results were obtained in two independent experiments (n=10 (PBS, CRKDKC), 12 (CR(NMe)EK and, 12 CRKDKC+CR(NMe)EKA). The black line indicates average of tumor volume. Statistical analysis was performed with Student's t-test. Double asterisk, p<0.01. FIG. 14B: H&E staining showing a large necrotic area in the middle of a treated tumor and blocked blood vessels in the viable tumor rim. Similarly sized tumors in the group that received CRKDKC particles, which home to tumor vessels but do not cause clotting, show no necrosis or blocked blood vessels.

FIGS. 15A and 15B: Fluorescence images of tumor-homing CRK-mixed with CR(NMe)EKA-conjugated SPIO nanoparticles day after last injection. Tumor sections were stained with anti-CD-31 (FIG. 15A) or anti-fibrino(gen) (FIG. 15B) and examined by confocal microscopy. Scale bars 200 μm (top) and 50 μm (bottom). Nuclei were stained with DAPI (small circular specs), mixture peptides conjugated SPIO (bright areas), and blood vessels were visualized with CD31 (FIG. 15A) Fibrinogen (light gray) (FIG. 15B) staining No damage or fibrin-filled blood vessels were detected in normal organs of the treated tumor mice in histological examination and fibrin(ogen) staining.

FIGS. 17A and 17B shows CEUS imaging of blood circulation in tumors of mice treated with peptide-coated nanoworms. (A) Mice preinjected with Ni-liposomes were subsequently injected with a mixture of CREKA-NWs and CRKDKC-NWs and, after the indicated periods of time, injected with an ultrasound contrast agent. CEUS and conventional ultrasound (US) images obtained at the different time points are shown. The images are representative of 3 tumors imaged. (B) Enhancement-analysis curves of blood flow in different tumor regions and the surrounding tissue from experiments described in panel A. The orientation of the tumors is slightly different between the time points because the mice were anesthetized for each scan and reintroduced to the ultrasound instrument. n=3.

DETAILED DESCRIPTION OF THE INVENTION

Figure 1C:
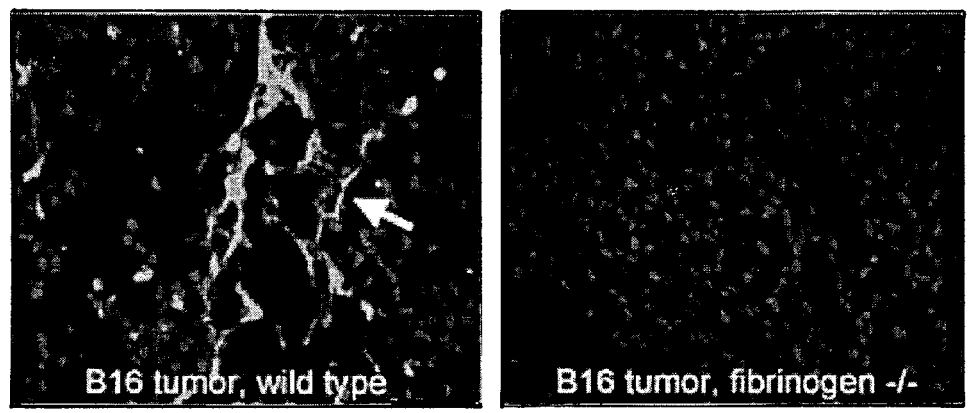
Figure 1C:
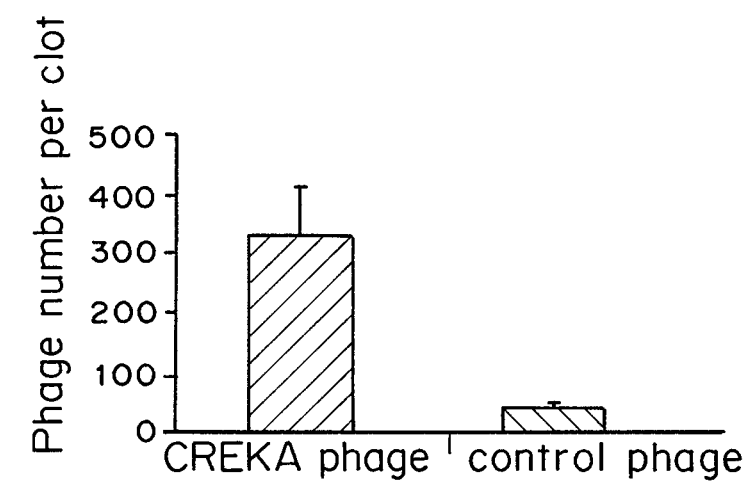

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed are compositions comprising a surface molecule and at least one modified clot-binding compound. The modified clot-binding compound can selectively bind to clotted plasma protein, wherein the composition causes clotting and amplifies the accumulation of the composition in tumors. The modified clot-binding compound can enhance the clotting in tumors compared to its unmodified derivative.

Also disclosed are methods comprising administering to a subject any of the disclosed compositions. The composition selectively homes to clotted plasma protein, wherein the composition causes clotting and amplifies the accumulation of the composition at the site of the clotted plasma protein.

Also disclosed are methods comprising administering to a subject a plurality of different of the disclosed compositions. In some forms, each of the plurality of different compositions comprises a surface molecule and at least one modified clot-binding compound. In some forms, at least one of the plurality of different compositions comprises a surface molecule and at least one modified clot-binding compound. In some forms, each of the plurality of different compositions selectively homes to clotted plasma protein. In some forms, at least one of the plurality of compositions selectively homes to clotted plasma protein. In some forms, each of the compositions causes clotting and amplifies the accumulation of the composition at the site of the clotted plasma protein. In some forms, at least one of the compositions causes clotting and amplifies the accumulation of the composition at the site of the clotted plasma protein.

The modified clot-binding compound can comprise a methylated clot-binding compound. The methylated clot-binding compound can comprise a methylated amino acid segment. The methylated amino acid segment can be selected from amino acid segments comprising a methylated derivative of amino acid sequence CREKA (SEQ ID NO: 1) or a conservative variant thereof, amino acid segments comprising a methylated derivative of amino acid sequence CREKA (SEQ ID NO:1), amino acid segments consisting of a methylated derivative of amino acid sequence CREKA (SEQ ID NO:1), and amino acid segments consisting of a methylated derivative amino acid sequence REK. The methylated amino acid segment can comprise a methylated derivative of amino acid sequence CREKA (SEQ ID NO: 1) or a conservative variant thereof. The methylated amino acid segment can comprise a methylated derivative of amino acid sequence CREKA (SEQ ID NO:1). The methylated amino acid segment can consist of a methylated derivative of amino acid sequence CREKA (SEQ ID NO:1). The methylated amino acid segment can consist of a methylated derivative of amino acid sequence REK.

The amino acid sequence can be N- or C-methylated in at least one position. The amino acid sequence can be C(NMe)REKA (SEQ ID NO:8), CR(NMe)EKA (SEQ ID NO:9), CR(CMe)EKA (SEQ ID NO:10), CRE(NMe)KA (SEQ ID NO:11), CRE(CMe)KA (SEQ ID NO:12), or CR(NMe)E(NMe)KA (SEQ ID NO:13). The amino acid sequence can be CR(NMe)EKA (SEQ ID NO:9), CRE(CMe)KA (SEQ ID NO:11), or CR(NMe)E(NMe)KA (SEQ ID NO:13).

The composition can further comprise a plurality of clot-binding compounds, wherein the clot-binding compounds selectively bind to clotted plasma protein, wherein the plurality of clot-binding compounds causes clotting and amplifies the accumulation of the composition in tumors. One or more of the plurality of clot-binding compounds can be modified clot-binding compounds, wherein the modified clot-binding compounds enhance the clotting in tumors compared to their unmodified derivatives. One or more of the modified clot-binding compounds of the plurality of clot-binding compounds can comprise a methylated clot-binding compound. One or more of the methylated clot-binding compounds of the plurality of clot-binding compounds can comprise a methylated amino acid segment.

Each of the methylated amino acid segments of the plurality of clot-binding compounds can be independently selected from amino acid segments comprising a methylated derivative of amino acid sequence CREKA (SEQ ID NO: 1) or a conservative variant thereof, amino acid segments comprising a methylated derivative of amino acid sequence CREKA (SEQ ID NO:1), amino acid segments consisting of a methylated derivative of amino acid sequence CREKA (SEQ ID NO:1), and amino acid segments consisting of a methylated derivative amino acid sequence REK. The methylated amino acid segments of the plurality of clot-binding compounds can each independently comprise a methylated derivative of amino acid sequence CREKA (SEQ ID NO: 1) or a conservative variant thereof. The methylated amino acid segments of the plurality of clot-binding compounds can each independently comprise a methylated derivative of amino acid sequence CREKA (SEQ ID NO:1). The methylated amino acid segments of the plurality of clot-binding compounds can each independently consist of a methylated derivative of amino acid sequence CREKA (SEQ ID NO:1). The methylated amino acid segments can each independently consist of a methylated derivative of amino acid sequence REK.

The methylated amino acid segments of the plurality of clot-binding compounds can each comprise a methylated derivative of amino acid sequence CREKA (SEQ ID NO: 1) or a conservative variant thereof. The methylated amino acid segments of the plurality of clot-binding compounds can each comprise a methylated derivative of amino acid sequence CREKA (SEQ ID NO:1). The methylated amino acid segments of the plurality of clot-binding compounds can each consist of a methylated derivative of amino acid sequence CREKA (SEQ ID NO:1). The methylated amino acid segments of the plurality of clot-binding compounds can each consist of a methylated derivative of amino acid sequence REK.

In some forms, the surface molecule can be thrombogenic. In some forms, the modified clot-binding compound can be thrombogenic.

The composition can further comprising one or more tumor-homing compounds. One or more of the tumor-homing compounds can comprise an amino acid segment. One or more of the amino acid segments of the tumor-homing compounds can comprise the amino acid sequence CRKDKC (SEQ ID NO:5) or a conservative derivative thereof or the amino acid sequence CGKRK (SEQ ID NO:7) or a conservative derivative thereof. One or more of the tumor-homing compounds can be thrombogenic.

The composition can bind inside tumor blood vessels. The composition can reduce tumor growth. The surface molecule can comprise an iron oxide nanoworm. The surface molecule can comprise an iron oxide nanoparticle. The surface molecule can comprise an albumin nanoparticle. The surface molecule can comprise a liposome. The surface molecule can comprise a microparticle. The surface molecule can comprise a fluorocarbon microbubble.

The composition can comprise at least 100 clot-binding compounds. The composition can comprise at least 1000 clot-binding compounds. The composition can comprise at least 10,000 clot-binding compounds.

The composition can further comprise one or more moieties. The moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, an image contrast agent, a fluorophore, fluorescein, rhodamine, a radionuclide, indium-111, technetium-99, carbon-11, and carbon-13. At least one of the moieties can be a therapeutic agent. The therapeutic agent can comprise a compound or composition for treating cancer. The therapeutic agent can comprise a compound or composition to induce programmed cell death or apoptosis. The therapeutic agent can be Abraxane. The therapeutic agent can be paclitaxel. The therapeutic agent can be taxol. In some forms, at least one of the moieties can be thrombogenic. In some forms, at least one of the moieties is not a clot-binding compound. In some forms, none of the moieties are clot-binding compounds. In some forms, at least one of the moieties is a homing compound, wherein the homing compound is not a clot-binding compound. At least one of the moieties can be a detectable agent. The detectable agent can be FAM.

The composition can selectively homes to tumor vasculature, wound sites, or both. The composition can have a therapeutic effect. The therapeutic effect can be a slowing in the increase of or a reduction of tumor burden. The therapeutic effect can be a slowing of the increase of or reduction of tumor size. The therapeutic effect can be a reduction or blocking of blood circulation in a tumor. The therapeutic effect can be a reduction or cessation of bleeding at a wound site. The therapeutic effect can be a decrease in the time for bleeding to stop at a wound site. The therapeutic effect can comprise a reduction in inflammation, an increase in speed of wound healing, reduction in amounts of scar tissue, decrease in pain, decrease in swelling, decrease in necrosis, or a combination.

The clotting can have a therapeutic effect. The subject can have one or more sites to be targeted, wherein the composition homes to one or more of the sites to be targeted. The subject can have a tumor, wherein the composition has a therapeutic effect on the tumor.

In some forms, the composition can comprise a sufficient number and composition of clot-binding compounds such that the composition causes clotting and amplifies the accumulation of the composition in tumors. Sufficiency of the number and composition of clot-binding compounds (modified or otherwise) can be determined by assessing clotting and amplification of the accumulation of the composition in tumors in a non-human animal.

The composition can comprise a sufficient density and composition of clot-binding compounds such that the composition causes clotting and amplifies the accumulation of the composition in tumors. Sufficiency of the density and composition of clot-binding compounds (modified or otherwise) can be determined by assessing clotting and amplification of the accumulation of the composition in tumors in a non-human animal.

A plurality of the clot-binding compounds can each be independently selected from an amino acid segment comprising the amino acid sequence REK, a fibrin-binding peptide, a clot-binding antibody, and a clot-binding small organic molecule. A plurality of the clot-binding compounds can each independently comprise an amino acid segment comprising the amino acid sequence REK. Modified clot-binding compounds can be independently selected from an amino acid segment comprising a modified form of the amino acid sequence REK, a modified form of a fibrin-binding peptide, a modified form of a clot-binding antibody, and a modified form of a clot-binding small organic molecule. The modified clot-binding compounds can each independently comprise an amino acid segment comprising a modified form of the amino acid sequence REK. A particularly useful modification is methylation.

The amino acid segments of clot-binding compounds can each be independently selected from amino acid segments comprising the amino acid sequence CREKA (SEQ ID NO: 1) or a conservative variant thereof, amino acid segments comprising the amino acid sequence CREKA (SEQ ID NO:1), amino acid segments consisting of the amino acid sequence CREKA (SEQ ID NO:1), and amino acid segments consisting of the amino acid sequence REK. The amino acid segments can each independently comprise the amino acid sequence CREKA (SEQ ID NO: 1) or a conservative variant thereof.

The amino acid segments can also each independently comprise the amino acid sequence CREKA (SEQ ID NO:1). The amino acid segment can also consist of the amino acid sequence CREKA (SEQ ID NO:1). The amino acid segment can consist of the amino acid sequence REK.

A plurality of the clot-binding compounds can each comprise a fibrin-binding peptide. The fibrin-binding peptides can independently be selected from the group consisting of fibrin binding proteins and fibrin-binding derivatives thereof. In another example, a plurality of the clot-binding compounds can each comprise a clot-binding antibody. Furthermore, a plurality of the clot-binding compounds can each comprise a clot-binding small organic molecule.

In some forms, each of the at least one of the plurality of different compositions selectively homes to clotted plasma protein, wherein each of the at least one of the plurality of compositions causes clotting and amplifies the accumulation of the compositions at the site of the clotted plasma protein. In some forms, each of the at least one of the plurality of different compositions can selectively home to clotted plasma protein, wherein each of the at least one of the plurality of compositions causes clotting and amplifies the accumulation of the compositions at the site of the clotted plasma protein. In some forms, at least one of the plurality of different compositions comprises a surface molecule and at least one unmodified clot-binding compound, wherein the unmodified clot-binding compound selectively binds to clotted plasma protein. In some forms, at least one of the plurality of different compositions comprises a surface molecule and at least one homing compound, wherein the homing compound is not a clot-binding compound. In some forms, the homing compound can selectively bind to tumor vasculature. In some forms, the homing compound can be a tumor-homing compound. In some forms, the tumor-homing compound can comprises an amino acid segment. In some forms, the amino acid segment of the tumor-homing compound can comprise the amino acid sequence CRKDKC (SEQ ID NO:5) or a conservative derivative thereof, or the amino acid sequence CGKRK (SEQ ID NO:7) or a conservative derivative thereof. In some forms, at least two of the plurality of different compositions can differ in the homing compounds of which the compositions are comprised. In some forms, at least two of the plurality of different compositions can differ in the clot-binding compounds of which the compositions are comprised. In some forms, each of the plurality of different compositions selectively homes to clotted plasma protein, wherein each of the at least one of the plurality of compositions causes clotting and amplifies the accumulation of the compositions at the site of the clotted plasma protein.

Further disclosed are compositions that not only home to tumors, but also amplify their own homing. The system is based on a clot-binding compound that recognizes clotted plasma proteins and selectively homes to tumors, where it binds to vessel walls and tumor stroma. Surface molecules coupled with the clot-binding compounds can accumulate in tumor vessels or at wound sites, where they induce additional local clotting, thereby producing new binding sites for more particles. The system mimics platelets, which also circulate freely but accumulate at a diseased site and amplify their own accumulation at that site. The clotting-based amplification greatly enhances tumor imaging, and a drug carrier function is also envisioned.

In developing new strategies for treating solid tumors, methods that involve targeting the vasculature of the tumor, rather than the tumor cells themselves, offer distinct advantages. Inducing a blockade of the blood flow through the tumor, e.g., through tumor vasculature specific fibrin formation, interferes with the influx and efflux processes in a tumor site, thus resulting in anti-tumor effect. Arresting the blood supply to a tumor can be accomplished through shifting the procoagulant-fibrinolytic balance in the tumor-associated vessels in favor of the coagulating (clotting) processes by specific exposure to clotting agents.

Compositions comprising modified clot-binding compounds are directed to the tumor cells themselves. There, they accumulate and induce additional clotting. A number of appropriate clot-binding compounds have been identified that can be modified and that are specifically or preferentially expressed, localized, adsorbed to or inducible on the cells or in the environment of the tumor vasculature and/or stroma. These are discussed in more detail below.

The disclosed compositions can, for example, cause clotting (thrombogenesis), can increase or enhance clotting at sites where the composition homes or is targeted, and/or can accumulate and increase or enhance accumulation of the composition at sites where the composition homes or is targeted. Such compositions can be considered thrombogenic compositions. These effects of the disclosed compositions can be caused by and/or enhanced by inclusion in the composition of, for example, one or more thrombogenic clot-binding compounds, one or more thrombogenic surface molecules, one or more thrombogenic compounds, one or more thrombogenic peptides, one or more thrombogenic clot-binding peptides, and/or one or more thrombogenic moieties. For example, the disclosed compositions can be comprised of one or more thrombogenic clot-binding compounds, one or more thrombogenic surface molecules, one or more thrombogenic compounds, one or more thrombogenic peptides, one or more thrombogenic clot-binding peptides, and/or one or more thrombogenic moieties. The disclosed compositions also can be comprised of one or more non-thrombogenic clot-binding compounds, one or more non-thrombogenic surface molecules, one or more non-thrombogenic compounds, one or more non-thrombogenic peptides, one or more non-thrombogenic clot-binding peptides, and/or one or more non-thrombogenic moieties.

A. Clot-Binding Compounds

The clot-binding compound can be any compound with the ability to interact with clots and/or components of clots such as clotted plasma proteins. It has been discovered that by using modified forms of clot-binding compounds the effectiveness of the clot amplification and of the effect on tumors can be increased. The composition can also comprise a sufficient number and composition of clot-binding compounds (modified or not) such that the composition causes clotting and amplifies the accumulation of the composition in tumors and at the site of injury. In one example, sufficiency of the number and composition of clot-binding compounds can be determined by assessing clotting and amplification of the accumulation of the composition in tumors in a non-human animal. In another example, sufficiency of the number and composition of clot-binding compounds can be determined by assessing clotting and amplification of the accumulation of the composition in at sites of clotting and at the site of injury. Clot-binding compounds can be modified or unmodified.

A plurality of the clot-binding compounds can each be independently selected from, for example, an amino acid segment comprising the amino acid sequence REK, an amino acid segment comprising the amino acid sequence CAR (such as CARSKNKDC (SEQ ID NO:6)), an amino acid segment comprising the amino acid sequence CRK (such as CRKDKC (SEQ ID NO:5)), a fibrin-binding peptide, a peptide that binds clots and not fibrin (such as CGLIIQKNEC(CLT1, SEQ ID NO: 2) and CNAGESSKNC(CLT2, SEQ ID NO: 3)), a clot-binding antibody, and a clot-binding small organic molecule. A plurality of the clot-binding compounds can each independently comprise an amino acid segment comprising the amino acid sequence REK. Such peptides are also described in U.S. Patent Application Publication No. 2008/0305101, which is hereby incorporated by reference for its description of such peptides. Peptides comprising amino acid sequences CAR or CRK are also described in U.S. Patent Application Publication No. 2009/0036349, which is hereby incorporated by reference for its description of such peptides.

The composition can comprise any number of clot-binding compounds. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more clot-binding compounds. The composition can also comprise any number in between those numbers listed above.

The term "homing molecule" as used herein, means any molecule that selectively homes in vivo to specified target sites or tissues in preference to normal tissue. Similarly, the term "homing peptide" or "homing peptidomimetic" means a peptide that selectively homes in vivo to specified target sites or tissues in preference to normal tissue. It is understood that a homing molecule that selectively homes in vivo to, for example, tumors can home to all tumors or can exhibit preferential homing to one or a subset of tumor types.

By "selectively homes" it is meant that in vivo, the homing molecule binds preferentially to the target as compared to non-target. For example, the homing molecule can bind preferentially to clotted plasma of one or more tumors, wound tissue, or blood clots, as compared to non-tumoral tissue or non-wound tissue. Such a homing molecule can selectively home, for example, to tumors. Selective homing to, for example, tumors generally is characterized by at least a two-fold greater localization within tumors (or other target), as compared to several tissue types of non-tumor tissue. A homing molecule can be characterized by 5-fold, 10-fold, 20-fold or more preferential localization to tumors (or other target) as compared to several or many tissue types of non-tumoral tissue, or as compared to most or all non-tumoral tissue. Thus, it is understood that, in some cases, a homing molecule homes, in part, to one or more normal organs in addition to homing to the target tissue. Selective homing can also be referred to as targeting.

Useful clot-binding compound can include, for example, clot-binding peptides, clot-binding antibodies, clot-binding small organic molecules, thrombogenic clot-binding compounds, thrombogenic clot-binding peptides, thrombogenic clot-binding antibodies, thrombogenic clot-binding small organic molecules, non-thrombogenic clot-binding compounds, non-thrombogenic clot-binding peptides, non-thrombogenic clot-binding antibodies, and/or non-thrombogenic clot-binding small organic molecules.

The composition can comprise a sufficient number, density, and/or composition of clot-binding compounds such that the composition causes clotting and amplifies the accumulation of the composition in tumors. Sufficiency of the number, density, and/or composition of clot-binding compounds (modified or otherwise) can be determined by assessing clotting and amplification of the accumulation of the composition in tumors in a non-human animal.

The density of clot-binding compounds on a surface molecule can be described in any suitable manner. For example, the density can be expressed as the number of clot-binding compounds per, for example, a given area, surface area, volume, unit, subunit, arm, etc. of the surface molecule. The density can also be relative to, for example, the area, surface area, volume, unit, subunit, arm, etc. of the entire surface molecule or to the area, surface area, volume, unit, subunit, arm, etc. of a portion of the surface molecule. For example, a sufficient density of clot-binding compound can be present in a portion of the surface molecule. The presence of this dense portion can cause clotting and amplify the accumulation of the composition. Thus, a composition having a sufficient density of clot-binding compounds can have a threshold density (or above) for the entire surface molecule or for just one or more portions of the surface molecule.

The density can be measured or calculated in any suitable manner. For example, the number or amount of clot-binding compounds present on a surface molecule or group of surface molecules can be measured by, for example, detecting the level or intensity of signal produced by labeled clot-binding compounds and calculating the density based on the structural characteristics of the surface molecule.

The density or threshold density of clot-binding compounds can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 clot-binding compounds per square nM of the entire or a portion of the surface molecule. The composition can also comprise any density in between those densities listed above.

The density or threshold density of clot-binding compounds can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 clot-binding compounds per square $\mu M$ of the entire or a portion of the surface molecule. The composition can also comprise any density in between those densities listed above.

The density or threshold density of clot-binding compounds can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 clot-binding compounds per cubic nM of the entire or a portion of the surface molecule. The composition can also comprise any density in between those densities listed above.

The density or threshold density of clot-binding compounds can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 clot-binding compounds per cubic μM of the entire or a portion of the surface molecule. The composition can also comprise any density in between those densities listed above.

1. Modified Clot-Binding Compounds

The disclosed clot-binding compounds can include modified forms of clot-binding compounds. The clot-binding compounds can have any useful modification. For example, some modifications can stabilize the clot-binging compound. For example, the disclosed clot-binding compounds include methylated clot-binding compounds. Methylated clot-binding compounds are particularly useful when the clot-binding compound includes a protein, peptide or amino acid segment. For example, a clot-binding compound can be a modified clot-binding compound, where, for example, the modified clot-binding compound includes a modified amino acid segment or amino acid sequence. For example, a modified clot-binding compound can be a methylated clot-binding compound, where, for example, the methylated clot-binding compound includes a methylated amino acid segment or amino acid sequence. Other modifications can be used, either alone or in combination. Where the clot-binding compound is, or includes, a protein, peptide, amino acid segment and/or amino acid sequences, the modification can be to the protein, peptide, amino acid segment, amino acid sequences and/or any amino acids in the protein, peptide, amino acid segment and/or amino acid sequences. Amino acid and peptide modifications are known to those of skill in the art, some of which are described below and elsewhere herein. Methylation is a particularly useful modification for the disclosed clot-binding compounds.

It has been discovered that by using modified forms of clot-binding compounds the effectiveness of the clot amplification and of the effect on tumors can be increased. The composition can also comprise a sufficient number and composition of clot-binding compounds (modified or not) such that the composition causes clotting and amplifies the accumulation of the composition in tumors and at the site of injury. In one example, sufficiency of the number and composition of modified and/or unmodified clot-binding compounds can be determined by assessing clotting and amplification of the accumulation of the composition in tumors in a non-human animal. Such methods are discussed in more detail below.

A plurality of modified and/or unmodified clot-binding compounds can each be independently selected from, for example, an amino acid segment comprising a modified or unmodified form of the amino acid sequence REK, an amino acid segment comprising a modified or unmodified form of the amino acid sequence CAR (such as CARSKNKDC (SEQ ID NO:6)), an amino acid segment comprising a modified or unmodified form of the amino acid sequence CRK (such as CRKDKC (SEQ ID NO:5)), a modified or unmodified form of a fibrin-binding peptide, a modified or unmodified form of a peptide that binds clots and not fibrin (such as CGLIIQKNEC(CLT1, SEQ ID NO: 2) and CNAGESSKNC (CLT2, SEQ ID NO: 3)), a modified or unmodified form of a clot-binding antibody, and a modified or unmodified form of a clot-binding small organic molecule. A plurality of the clot-binding compounds can each independently comprise an amino acid segment comprising a modified or unmodified form of the amino acid sequence REK. Such peptides are also described in U.S. Patent Application Publication No. 2008/0305101, which is hereby incorporated by reference for its description of such peptides. Peptides comprising amino acid sequences CAR or CRK are also described in U.S. Patent Application Publication No. 2009/0036349, which is hereby incorporated by reference for its description of such peptides.

The composition can comprise any number of modified and/or unmodified clot-binding compounds. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more modified and/or unmodified clot-binding compounds. The composition can also comprise any number in between those numbers listed above.

As used herein, a "methylated derivative" of a protein, peptide, amino acid segment, amino acid sequence, etc. refers to a form of the protein, peptide, amino acid segment, amino acid sequence, etc. that is methylated. Unless the context indicates otherwise, reference to a methylated derivative of a protein, peptide, amino acid segment, amino acid sequence, etc. does no include any modification to the base protein, peptide, amino acid segment, amino acid sequence, etc. other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations. As another example, reference to a methylated derivative of an amino acid segment that includes amino acid substitutions would include methylated forms of the amino acid sequence of the amino acid segment and methylated forms of the amino acid sequence of the amino acid segment include amino acid substitutions.

Peptides can have a variety of modifications. Modifications can be used to change or improve the properties of the peptides. For example, the disclosed peptides can be N-methylated, O-methylated, S-methylated, C-methylated, or a combination at one or more amino acids.

The amino and/or carboxy termini of the disclosed peptides can be modified. Amino terminus modifications include methylation (e.g., —$NHCH_3$ or —$N(CH_3)_2$), acetylation (e.g., with acetic acid or a halogenated derivative thereof such as α-chloroacetic acid, α-bromoacetic acid, or .alpha.-iodoacetic acid), adding a benzyloxycarbonyl (Cbz) group, or blocking the amino terminus with any blocking group containing a carboxylate functionality defined by RCOO— or sulfonyl functionality defined by R—$SO_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the disclosed peptides, or incorporate a desamino or descarboxy residue at the termini of the peptide, so that there is no terminal amino or carboxyl group, to decrease susceptibility to proteases or to restrict the conformation of the peptide. C-terminal functional groups of the disclosed peptides include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower ($C_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods [e.g., as described in Hruby, et al. (1990) Biochem J. 268:249-262].

The disclosed peptides also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis [See, Morgan and Gainor (1989) Ann. Rep. Med. Chem. 24:243-252]. These techniques include, but are not limited to, replacing the peptide backbone with a backbone composed of phosphonates, amidates, carbamates, sulfonamides, secondary amines, and N-methylamino acids.

2. Peptides and Amino Acid Segments

In some forms, the clot-binding compound can be or include a peptide, peptidomimetic, and/or amino acid segment. Unless the context indicates otherwise, reference herein to "peptide" is intended to refer also to amino acid segments, which can form a part of, or constitute an entire, peptide. The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides and amino acid segments can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

The disclosed amino acid segments can have, for example, a relatively short length of less than six, seven, eight, nine, ten, 12, 15, 20, 25, 30, 35 or 40 residues. The disclosed amino acid segments also can be useful in the context of a significantly longer sequence. Thus, the amino acid segments can have, for example, a length of up to 50, 100, 150, 200, 250, 300, 400, 500, 1000 or 2000 residues. In particular embodiments, an amino acid segment can have a length of at least 10, 20, 30, 40, 50, 60, 70, 80, 90, 100 or 200 residues. In further embodiments, an amino acid segment can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins, protein sequences, peptides, peptides sequences, and amino acid sequences, it is understood that the nucleic acids that can encode those sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Molecules can be produced that resemble peptides, but which are not connected via a natural peptide linkage. For example, linkages for amino acids or amino acid analogs can include —CH$_2$NH—, —CH$_2$S—, —CH$_2$—CH$_2$—, —CH=CH—(cis and trans), —COCH$_2$—, —CH(OH)CH$_2$—, and —CHH$_2$SO—(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$); Spatola et al. Life Sci 38:1243-1249 (1986) (—CHH$_2$—S); Hann J. Chem. Soc Perkin Trans. I 307-314 (1982) (—CH—CH—, cis and trans); Almquist et al. J. Med. Chem. 23:1392-1398 (1980) (—COCH$_2$—); Jennings-White et al. Tetrahedron Lett 23:2533 (1982) (—COCH$_2$—); Szelke et al. European Appin, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as β-alanine, γ-aminobutyric acid, and the like.

Also disclosed are bifunctional peptides, which contain the clot-binding peptide fused to a second peptide having a separate function. Such bifunctional peptides have at least two functions conferred by different portions of the full-length molecule and can, for example, display anti-angiogenic activity or pro-apoptotic activity in addition to the ability to enhance clotting.

Also disclosed are isolated multivalent peptides that include at least two subsequences each independently containing a peptide or amino acid segment (for example, the amino acid sequence SEQ ID NO: 1, or a conservative variant or peptidomimetic thereof). The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. This is in addition to the multiple clot-binding compounds that can comprise the disclosed compositions. In a further embodiment, the multivalent peptide can contain identical subsequences, such as repeats of SEQ ID NO: 1. In a further embodiment, the multivalent peptide contains contiguous identical or non-identical subsequences, which are not separated by any intervening amino acids.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an N$^\alpha$—C$^\alpha$ cyclized amino acid; an N$^\alpha$.-methylated amino acid; a β- or γ-amino cycloalkane carboxylic acid; an α,β-unsaturated amino acid; a β,β-dimethyl or β-methyl amino acid; a β-substituted-2,3-methano amino acid; an N—C$^\epsilon$ or C$^\alpha$—C$^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with cancerous cells.

3. Homing Peptides

There are several examples in the art of peptides that home to clotted plasma protein. Examples include REK, peptides comprising REK, CREKA (SEQ ID NO: 1), and peptides comprising CREKA (SEQ ID NO: 1). The amino acid segments can also be independently selected from amino acid segments comprising the amino acid sequence CREKA (SEQ ID NO: 1) or a conservative variant thereof, amino acid segments comprising the amino acid sequence CREKA (SEQ ID NO:1), amino acid segments consisting of the amino acid sequence CREKA (SEQ ID NO:1), and amino acid segments consisting of the amino acid sequence REK. The amino acid segments can each independently comprise the amino acid sequence CREKA (SEQ ID NO: 1) or a conservative variant thereof.

The amino acid segments can also each independently comprise the amino acid sequence CREKA (SEQ ID NO:1). The amino acid segment can also consist of the amino acid sequence CREKA (SEQ ID NO:1). The amino acid segment can consist of the amino acid sequence REK.

4. Other Clot-Binding Peptides

The clot-binding compound can also comprise a fibrin-binding peptide (FBP). Examples of fibrin-binding peptides are known in the art (Van Rooijen N, Sanders A (1994) J Immunol Methods 174: 83-93; Moghimi S M, Hunter A C, Murray J C (2001) Pharmacol Rev 53: 283-318; U.S. Pat. No. 5,792,742, all herein incorporated by reference in their entirety for their teaching concerning fibrin binding peptides).

Clot-binding peptides can also bind to proteins other than fibrin. Example include peptides that bind to fibronectin that has become incorporated into a clot (Pilch et al., (2006) PNAS, 103: 2800-2804, hereby incorporated in its entirety for its teaching concerning clot-binding peptides). An example of clot-binding peptides include, but is not limited to, CGLIIQKNEC (CLT1, SEQ ID NO: 2) and CNAGESSKNC (CLT2, SEQ ID NO: 3). The amino acid segments can also be independently selected from amino acid segments comprising the amino acid sequence CLT1 or CLT2 (SEQ ID NOS: 2 or 3) or a conservative variant thereof, amino acid segments comprising the amino acid sequence CLT1 or CLT2 (SEQ ID NOS: 2 or 3), or amino acid segments consisting of the amino acid sequence CLT1 or CLT2 (SEQ ID NOS: 2 or 3). The amino acid segments can each independently comprise the amino acid sequence CLT1 or CLT2 (SEQ ID NOS: 2 or 3) or a conservative variant thereof.

The amino acid segments can also each independently comprise the amino acid sequence CLT1 or CLT2 (SEQ ID NOS: 2 or 3). The amino acid segment can also consist of the amino acid sequence CLT1 or CLT2 (SEQ ID NOS: 2 or 3).

The amino acid segments can also each independently comprise the amino acid sequence CARSKNKDC (SEQ ID NO:6)), and the amino acid sequence CRK (such as CRKDKC (SEQ ID NO:5). Peptides comprising amino acid sequences CAR or CRK are also described in U.S. Patent Application Publication No. 2009/0036349, which is hereby incorporated by reference for its description of such peptides.

5. Clot-Binding Antibodies

The clot-binding compound can comprise a clot-binding antibody. Examples of clot-binding antibodies are known in the art (Holvoet et al. Circulation, Vol 87, 1007-1016, 1993; Bode et al. J. Biol. Chem., Vol. 264, Issue 2, 944-948, January, 1989; Huang et al. Science 1997: Vol. 275. no. 5299, pp. 547-550, all of which are herein incorporated by reference in their entirety for their teaching concerning clot-binding antibodies).

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to bind to, or otherwise interact with, clots. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222: 581, 1991).

Human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (JA) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

6. Small Organic Molecules

The clot-binding compound can also be a small organic molecule. Small organic molecules that are capable of interacting with, or binding to, clots are known in the art. These molecules can also be identified by methods known in the art, such as combinatorial chemistry. Some forms of small organic molecules can be organic molecules having a molecular weight of less than 1000 Daltons.

Combinatorial chemistry includes but is not limited to all methods for isolating small molecules that are capable of interacting with a clot, molecules associated with a clot such as fibrin or fibronectin, or clotted plasma protein, for example. One synthesizes a large pool of molecules and subjects that complex mixture to some selection and enrichment process, such as the detection of an interaction with clots.

Using methodology well known to those of skill in the art, in combination with various combinatorial libraries, one can isolate and characterize those small molecules which bind to or interact with the desired target. The relative binding affinity of these compounds can be compared and optimum compounds identified using competitive binding studies, which are well known to those of skill in the art. For example, a competitive binding study using CREKA (SEQ ID NO: 1) can be used.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes. Libraries of small organic molecules generally comprise at least 2 organic compounds, often at least about 25, 100 500 different organic compounds, more usually at least about 1000 different organic compounds, preferably at least about 2500 different organic compounds, more preferably at least about 5000 different organic compounds and most preferably at least about 10,000 or more different organic compounds. Libraries may be selected or constructed such that each individual molecule of the library may be spatially separated from the other molecules of the library (e.g., each member of the library is present in a separate microtiter well) or two or more members of the library may be combined if methods for deconvolution are readily available. The methods by which the library of organic compounds is prepared will not be critical to the invention.

B. Tumor-Homing Compounds

The disclosed compositions can also include one or more tumor-homing compounds. Tumor-homing compounds are compounds that selectively home to tumors and tumor-associated tissue. Many compounds that target, bind to, and/or home to tumors are known, most of which can be used as tumor-homing compounds in the disclosed compositions. Because tumors can include clot-related proteins, some clot-binding and clot-homing compounds can also be tumor-homing compounds. Such tumor-homing clot-binding compounds can be used as tumor-homing compounds as described herein.

Tumor-homing compounds can each be independently selected from, for example, an amino acid segment comprising the amino acid sequence REK, an amino acid segment comprising the amino acid sequence CAR (such as CARSKNKDC (SEQ ID NO:6)), an amino acid segment comprising the amino acid sequence CRK (such as CRKDKC (SEQ ID NO:5)), a fibrin-binding peptide, a peptide that binds clots and not fibrin (such as CGLIIQKNEC (CLT1, SEQ ID NO: 2) and CNAGESSKNC (CLT2, SEQ ID NO: 3)), a clot-binding antibody, and a clot-binding small organic molecule. A plurality of the clot-binding compounds can each independently comprise an amino acid segment comprising the amino acid sequence REK. Such peptides are also described in U.S. Patent Application Publication No. 2008/0305101, which is hereby incorporated by reference for its description of such peptides. Peptides comprising amino acid sequences CAR or CRK are also described in U.S. Patent Application Publication No. 2009/0036349, which is hereby incorporated by reference for its description of such peptides.

The composition can comprise any number of tumor-homing compounds. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more tumor-homing compounds. The conjugate can also comprise any number in between those numbers listed above.

The tumor-homing compound can also comprise a fibrin-binding peptide (FBP). Examples of fibrin-binding peptides are known in the art (Van Rooijen N, Sanders A (1994) J Immunol Methods 174: 83-93; Moghimi S M, Hunter A C, Murray J C (2001) Pharmacol Rev 53: 283-318; U.S. Pat. No. 5,792,742, all herein incorporated by reference in their entirety for their teaching concerning fibrin binding peptides).

Tumor-homing compounds can also bind to proteins other than fibrin. Example include peptides that bind to fibronectin that has become incorporated into a clot (Pilch et al., (2006) PNAS, 103: 2800-2804, hereby incorporated in its entirety for its teaching concerning clot-binding peptides). An example of clot-binding peptides include, but is not limited to, CGLIIQKNEC (CLT1, SEQ ID NO: 2) and CNAGESSKNC (CLT2, SEQ ID NO: 3). The amino acid segments can also be independently selected from amino acid segments comprising the amino acid sequence CLT1 or CLT2 (SEQ ID NOS: 2 or 3) or a conservative variant thereof, amino acid segments comprising the amino acid sequence CLT1 or CLT2 (SEQ ID NOS: 2 or 3), or amino acid segments consisting of the amino acid sequence CLT1 or CLT2 (SEQ ID NOS: 2 or 3). The amino acid segments can each independently comprise the amino acid sequence CLT1 or CLT2 (SEQ ID NOS: 2 or 3) or a conservative variant thereof.

The amino acid segments can also each independently comprise the amino acid sequence CLT1 or CLT2 (SEQ ID NOS: 2 or 3). The amino acid segment can also consist of the amino acid sequence CLT1 or CLT2 (SEQ ID NOS: 2 or 3).

The amino acid segments can also each independently comprise the amino acid sequence CARSKNKDC (SEQ ID NO:6)), and the amino acid sequence CRK (such as CRKDKC (SEQ ID NO:5). Peptides comprising amino acid sequences CAR or CRK are also described in U.S. Patent Application Publication No. 2009/0036349, which is hereby incorporated by reference for its description of such peptides.

Tumor-homing compounds can also be modified. Any of the modifications described herein for clot-binding compounds can also be used with the disclosed tumor-homing compounds. Tumor-homing compounds can be thrombogenic or non-thrombogenic.

C. Surface Molecules

The surface molecules, alternatively referred to as a surface particles, disclosed herein can be conjugated with clot-binding compounds in such a way that the composition is delivered to a clot, where it can accumulate and cause further clotting. The surface molecule can be any substance that can be used with the clot-binding compounds, and is not restricted by size or substance. Examples include, but are not limited to, nanoparticles (such as iron oxide nanoparticles or albumin nanoparticles), liposomes, small organic molecules, microparticles, or microbubbles, such as fluorocarbon microbubbles. The term surface molecule is used to identify a component of the disclosed composition but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be conjugated with a plurality of clot-binding compounds such that at least some of the clot-binding compounds are presented and/or accessible on the surface of the surface molecule. A variety of examples of suitable surface molecules are described and disclosed herein.

The surface molecule can be detectable, or can be a therapeutic agent such as Abraxane™. The section below, which discusses moieties that can be detectable or therapeutic, also applies to the surface molecule. Surface molecules can be thrombogenic or non-thrombogenic.

1. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohoms, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

2. Liposomes

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 nm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

D. Moieties

The composition disclosed herein can further comprise one or more moieties. For example, the moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, an image contrast agent, a fluorophore, fluorescein, rhodamine, a radionuclide, indium-111, technetium-99, carbon-11, and carbon-13. At least one of the moieties can be a therapeutic agent. Examples of therapeutic agents are paclitaxel and taxol. At least one of the moieties can be a detectable agent.

As used herein, the term "moiety" is used broadly to mean a physical, chemical, or biological material that generally imparts a biologically useful function to a linked or conjugated molecule. As disclosed herein, the properties of the moiety can also be found in a surface molecule, or both the surface molecule and the moiety can share one of the traits disclosed herein. For example, the surface molecule can comprise a detectable agent, while the moiety can comprise a therapeutic agent. This also applies for the clot-binding compound, which can also comprise one or more of the properties of moieties as disclosed herein. The description of therapeutic and detectable agents which follows is intended to apply to any of moieties, surface molecules, or clot-binding compounds. Thus, for example, moieties can be conjugated to, coupled to, or can be part of the disclosed surface molecules, clot-binding compounds, compositions, or conjugates of surface molecules and clot-binding compounds.

A moiety can be any natural or normatural material including, without limitation, a biological material, such as a cell, phage or other virus; an organic chemical such as a small molecule; a radionuclide; a nucleic acid molecule or oligonucleotide; a polypeptide; or a peptide. Useful moieties include, but are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a composition. Moieties can be thrombogenic or non-thrombogenic.

1. Therapeutic Agents

The moiety can be a therapeutic agent. As used herein, the term "therapeutic agent" means a molecule which has one or more biological activities in a normal or pathologic tissue. A variety of therapeutic agents can be used as a moiety. The therapeutic agent can comprise a compound or composition for treating cancer. The therapeutic agent can comprise a compound or composition to induce programmed cell death or apoptosis.

In some embodiments, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful with the compositions disclosed herein. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cancer chemotherapeutic agent useful with the compositions disclosed herein also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a useful cancer chemotherapeutic agent. Similarly, a vinca alkaloid such as vindesine, vinblastine or vinorelbine; or an antimetabolite such as 5-fluorouracil, 5-fluorouridine or a derivative thereof can be a useful cancer chemotherapeutic agent.

A platinum agent also can be a useful cancer chemotherapeutic agent. Such a platinum agent can be, for example, cisplatin or carboplatin as described, for example, in Crown, Seminars in Oncol. 28:28-37 (2001). Other useful cancer chemotherapeutic agents include, without limitation, methotrexate, mitomycin-C, adriamycin, ifosfamide and ansamycins.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a composition for treatment of breast cancer (Fisher et al., J. Natl. Cancer Instit. 90:1371-1388 (1998)).

The therapeutic agent can be an antibody such as a humanized monoclonal antibody. As an example, the anti-epidermal growth factor receptor 2 (HER2) antibody, trastuzumab (Herceptin; Genentech, South San Francisco, Calif.) can be a therapeutic agent useful for treating HER2/neu overexpressing breast cancers (White et al., Annu Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-$\alpha$ (TNF-$\alpha$), tumor necrosis factor-$\beta$ (TNF-$\beta$), granulocyte macrophage colony stimulating factor (GM-CSF), granulocyte colony stimulating factor (G-CSF), interferon .alpha. (IFN-$\alpha$); interferon .gamma. (IFN-$\gamma$), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., *J. Neurooncol.* 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. Int. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of anti-thrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

The compositions disclosed herein can also be used at a site of inflammation or injury. Moieties useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful to target a wound or other infected sites. Thus, for example, also disclosed are moieties comprising an antimicrobial peptide, where the composition is selectively internalized and exhibits a high toxicity to the targeted area. Useful antimicrobial peptides can have low mammalian cell toxicity when not incorporated into the composition. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of Escherichia coli, Pseudomonas aeruginosa or Staphylococcus aureus. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic .alpha.-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:151-155 (1990).; and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into the composition disclosed herein can have low mammalian cell toxicity when linked to the composition. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM.

In one embodiment, disclosed are compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art.

An antimicrobial peptide that induces significant mitochondrial swelling at, for example, 50 µM, 40 µM, 30 µM, 20 µM, 10 µM, or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197:109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the disclosed compositions and methods. Thus, it is understood that the compositions disclosed herein can contain one or more of such therapeutic agents and that additional components can be included as part of the composition, if desired. As a non-limiting example, it can be desirable in some cases to utilize an oligopeptide spacer between the clot-binding compound and the therapeutic agent (Fitzpatrick and Garnett, Anticancer Drug Des. 10:1-9 (1995)).

Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work best if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The disclosed compounds can use any of these or similar agents.

2. Detectable Agents

The moiety in the disclosed compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique, a magnetic resonance technique, or an ultrasound technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethaneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and 1-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011, 686); positron emitters, such as Cu-64, C-11, and 0-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or T1-201.

The use of Technitium-99m (Tc-99m) is preferable and has been described in other applications, for example, see U.S. Pat. Nos. 4,418,052 and 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N-,N',N'',N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbiurn(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to the composition in such a way so as not to interfere with the ability of the clot-binding compound to interact with the clotting site. In some embodiments, the detectable agent can be chemically bound to the clot-binding compound. In some embodiments, the detectable agent can be chemically bound to a moiety that is itself chemically bound to the clot-binding compound, indirectly linking the imaging and targeting moieties.

3. Homing Molecules

Homing molecules other than clot-binding compounds, can be used in the disclosed compositions. For example, disclosed are homing molecules that selectively home to, for example, clotted plasma of one or more tumors, wound tissue, or blood clots. A variety of homing molecules can be used in the disclosed compositions, conjugates and methods. Such homing molecules include, without limitation, peptides as disclosed herein. The disclosed compounds, compositions, conjugates and methods can include or use the disclosed homing molecules in various forms, including peptides and peptidomimetics as disclosed. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby.

As used herein, the term "molecule" is used broadly to mean a polymeric or non-polymeric organic chemical such as a small molecule drug; a nucleic acid molecule such as an RNA, a DNA such as a cDNA or oligonucleotide; a peptide; or a protein such as a growth factor or an antibody or fragment thereof such as an Fv, Fd, or Fab fragment or another antibody fragment containing the antigen-binding domain.

In some embodiments, a homing molecule can be a molecule that selectively homes to, for example, clotted plasma of one or more tumors, wound tissue, or blood clots and which is not an antibody or antigen-binding fragment thereof. The term "antibody" is an art-recognized term that refers to a peptide or polypeptide containing one or more complementarity determining regions (CDRs). See, for example, Borrabaeck, Antibody Engineering 2nd Edition, Oxford University Press, New York (1995).

Homing, including preferential and/or selective homing, does not mean that the homing molecule does not bind to any normal and/or non-targeted areas (for example, non-tumor, non-clot, and/or non-wound). In some embodiments, homing selectivity can be, for example, at least about 20-fold, at least about 30-fold, at least about 50-fold, at least about 75-fold, at least about 100-fold, at least about 150-fold, or at least about 200-fold selective for a corresponding target in terms of relative $K_i$ over other non-target components. In some embodiments, the homing molecule can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, the homing molecule can have a $K_i$ value against a target of less than about 50 µM, less than about 25 µM, less than about 20 µM, less than about 15 µM, less than about 10 µM, less than about 5 µM, less than about 3 µM, or less than about 1 µM, less than about 500 nM, less than about 250 nM, less than about 200 nM, less than about 150 nM, less than about 100 nM, or less than about 75 nM. In some preferred embodiments, the homing molecule can have a $K_i$ value against a target of more than about 50 µM, more than about 25 µM, more than about 20 µM, more than about 15 µM, more than about 10 µM, more than about 5 µM, more than about 3 µM, or more than about 1 µM, more than about 500 nM, more than about 250 nM, more than about 200 nM, more than about 150 nM, more than about 100 nM, more than about 50 nM, more than about 25 nM, more than about 20 nM, more than about 15 nM, more than about 10 nM, more than about 5 nM, more than about 3 nM, or more than about 1 nM. In some preferred embodiments, the targeting moiety binds its target with a $K_D$ less than about $10^{-4}$ M, less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M.

Binding in the context of a homing molecule recognizing and/or binding to its target generally involves non-covalent binding and interactions, for example where a homing molecule can bind or attach to its target by non-covalent binding. Binding can be either high affinity or low affinity, preferably high affinity. Examples of binding forces that can be useful include, but are not limited to, non-covalent bonds, such as dipole interactions, electrostatic forces, hydrogen bonds, hydrophobic interactions, ionic bonds, and/or van der Waals forces. Binding can also involve covalent binding, for example where a homing molecule can bind, attach or otherwise couple to its target by covalent binding.

E. Pharmaceutical Compositions and Carriers

The disclosed compositions can be administered in vivo either alone or in a pharmaceutically acceptable carrier. By "pharmaceutically acceptable" is meant a material that is not biologically or otherwise undesirable, i.e., the material can be administered to a subject, along with the composition disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells). Carriers can be thrombogenic or non-thrombogenic.

1. Pharmaceutically Acceptable Carriers

The compositions disclosed herein can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

F. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, peptides, etc., are also disclosed. Thus, the products produced using the molecular modeling approaches that involve the disclosed compositions are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

G. Compositions with Similar Functions

It is understood that the compositions disclosed herein have certain functions, such as binding to clots or enhancing clot formation. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

H. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits can include the compositions disclosed herein.

I. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

J. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

K. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

L. Peptide Synthesis

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NO:1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Methods

Disclosed herein are methods comprising administering to a subject one or more of the compositions disclosed herein. The composition can selectively home to clotted plasma protein. The composition can cause clotting and amplify the accumulation of the composition at the site of the clotted plasma protein. Some forms of the method comprise administering to a subject the composition disclosed herein, wherein the composition selectively homes to clotted plasma protein, wherein the composition causes clotting and amplifies the accumulation of the composition at the site of the clotted plasma protein. The composition can selectively homes to tumor vasculature, wound sites, or both.

Also disclosed are methods comprising administering to a subject a plurality of different of the disclosed compositions. In some forms, each of the plurality of different compositions comprises a surface molecule and at least one modified clot-binding compound. In some forms, at least one of the plurality of different compositions comprises a surface molecule and at least one modified clot-binding compound. In some forms, each of the plurality of different compositions selectively homes to clotted plasma protein. In some forms, at least one of the plurality of compositions selectively homes to clotted plasma protein. In some forms, each of the compositions causes clotting and amplifies the accumulation of the composition at the site of the clotted plasma protein. In some forms, at least one of the compositions causes clotting and amplifies the accumulation of the composition at the site of the clotted plasma protein.

In one example, the composition can have a therapeutic effect. This can be achieved by the enhanced clot formation that occurs because of the composition. This effect can be enhanced by the delivery of a therapeutic agent to the site of the tumor or wound site.

The therapeutic effect can be a slowing in the increase of or a reduction of tumor burden. This slowing in the increase of, or reduction in the tumor burden, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in the increase of, or reduction in the tumor burden of, compared with a non-treated tumor, or a tumor treated by a different method.

The therapeutic effect can also be a reduction or blocking of blood circulation in a tumor. This reduction or blocking of blood circulation in a tumor, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in effective blocking of blood circulation in a tumor, compared with a non-treated tumor, or a tumor treated by a different method.

The therapeutic effect can also be a reduction or cessation of bleeding at a wound site. This reduction or cessation of bleeding at a wound site can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more reduction or cessation of bleeding at a wound site compared to a non-treated wound, or a wound treated with a different method.

The therapeutic effect can also be a decrease in the time for bleeding to stop in a wound site. This reduction or cessation of bleeding at a wound site can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more decrease in the time for bleeding to stop at a wound site compared to a non-treated wound, or a wound treated with a different method.

The therapeutic effect can also comprises a reduction in inflammation, an increase in speed of wound healing, reduction in amounts of scar tissue, decrease in pain, decrease in swelling, decrease in necrosis, or a combination. This effect can be a 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement compared to a non-treated subject, or a subject treated with a different method.

Furthermore, the clotting itself can have a therapeutic effect, as disclosed elsewhere herein. The subject can have one or more sites to be targeted, wherein the composition homes to one or more of the sites to be targeted. For example, the subject can have multiple tumors or sites of injury.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

The disclosed compositions can also be administered following decoy particle pretreatment to reduce uptake of the compositions by reticuloendothelial system (RES) tissues. Such decoy particle pretreatment can prolong the blood half-life of the particles and increases tumor targeting.

The method can further comprise, following administering, detecting the disclosed compositions. The disclosed compositions can be detected by fluorescence, CT scan, PET or MRI. The disclosed compositions can be detected by fluorescence. The disclosed compositions can conjugate with tumor vasculature or a tumor in a subject.

In some forms, each of the at least one of the plurality of different compositions selectively homes to clotted plasma protein, wherein each of the at least one of the plurality of compositions causes clotting and amplifies the accumulation of the compositions at the site of the clotted plasma protein. In some forms, at least one of the plurality of different compositions comprises a surface molecule and at least one unmodified clot-binding compound, wherein the unmodified clot-binding compound selectively binds to clotted plasma protein. In some forms, at least one of the plurality of different compositions comprises a surface molecule and at least one homing compound, wherein the homing compound is not a clot-binding compound. In some forms, the homing compound can selectively bind to tumor vasculature. In some forms, the homing compound can be a tumor-homing compound. In some forms, the tumor-homing compound can comprise an amino acid segment. In some forms, the amino acid segment of the tumor-homing compound can comprise the amino acid sequence CRKDKC (SEQ ID NO:5) or a conservative derivative thereof, or the amino acid sequence CGKRK (SEQ ID NO:7) or a conservative derivative thereof. In some forms, at least two of the plurality of different compositions can differ in the homing compounds of which the compositions are comprised. In some forms, at least two of the plurality of different compositions can differ in the clot-binding compounds of which the compositions are comprised.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

Biomimetic Amplification of Nanoparticle Homing to Tumors

Nanoparticle-based diagnostics and therapeutics are useful because multiple functions can be built into the particles. One such function is an ability to home to specific sites in the body. Described herein are biomimetic particles that not only home to tumors, but also amplify their own homing. The system is based on a peptide that recognizes clotted plasma proteins and selectively homes to tumors, where it binds to vessel walls and tumor stroma. Iron oxide nanoparticles and liposomes coated with this tumor-homing peptide accumulate in tumor vessels, where they induce additional local clotting, thereby producing new binding sites for more particles. The system mimics platelets, which also circulate freely but accumulate at a diseased site and amplify their own accumulation at that site. The clotting-based amplification greatly enhances tumor imaging, and the addition of a drug carrier function to the particles can also be used.

1. Results

Figure 5A:
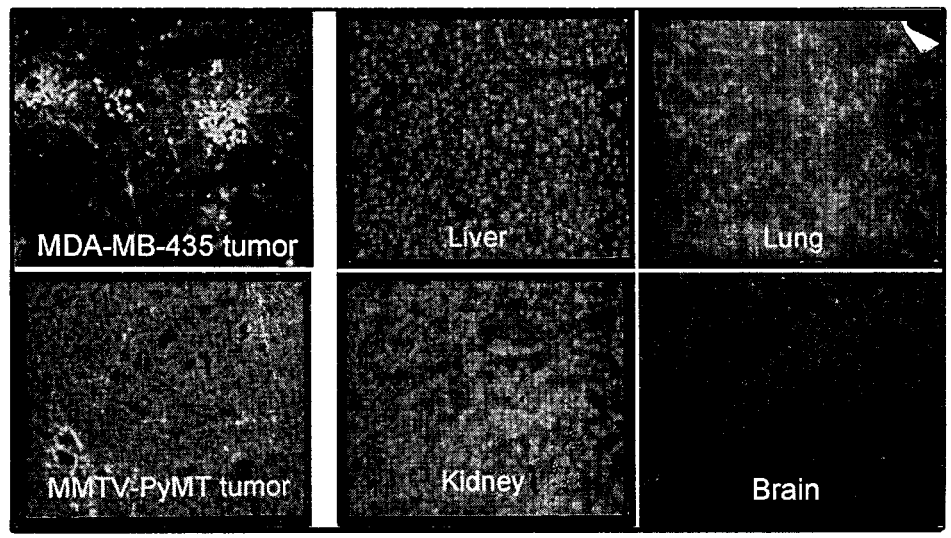
FIGS. 5A and 5B show tumor homing of CREKA peptide. (A). Balb/c nude mice bearing MDA-MB-435 human breast cancer xenograft tumors or transgenic MMTV PyMT mice with breast tumors were intravenously injected with 0.1 mg of fluorescein-CREKA. The animals were sacrificed by perfusion 24 hours post-injection and tissue sections were examined by fluorescent microscopy. Right panel, control organs of MDA-MB 435 tumor mice. Magnification 200×. (B). Whole animal imaging of MDA-MB-435 tumor mouse injected 6 hours earlier with 30 µg of Alexa Fluor 647-labeled CREKA. Maestro imaging system (Cambridge Research Inc., Woburn, Mass.) was used to acquire and process the image. The arrow points to the tumor and the arrowhead to the urinary bladder. Note that the peptide is excreted into the urine and does not accumulate in the liver.
Figure 5B:
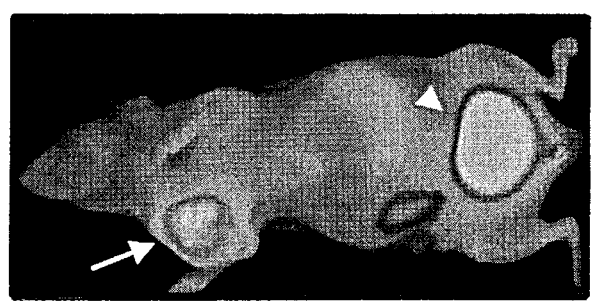

CREKA peptide. A tumor-homing peptide was used to construct targeted nanoparticles. This peptide was identified by in vivo screening of phage-displayed peptide libraries (Hoffman 2003; Pasqualini 1996) for tumor homing in tumor-bearing MMTV-PyMT transgenic breast cancer mice (Hutchinson 2000). The most frequently represented peptide sequence in the selected phage preparation was CREKA (cys-arg-glu-lys-ala; SEQ ID NO:1). The CREKA peptide was synthesized with a fluorescent dye attached to the N-terminus and the in vivo distribution of the peptide was studied in tumor-bearing mice. Intravenously injected CREKA peptide was readily detectable in the PyMT tumors, and in MDA-MB-435 human breast cancer xenografts, minutes to hours after the injection. The peptide formed a distinct meshwork in the tumor stroma (FIG. 5), and it also highlighted the blood vessels in the tumors. The CREKA peptide was essentially undetectable in normal tissues. In agreement with the microscopy results, whole body imaging using CREKA peptide labeled with the fluorescent dye Alexa 647 revealed peptide accumulation in the breast cancer xenografts, and in the bladder, reflecting elimination of excess peptide into the urine (FIG. 5B).

Tumors contain a meshwork of clotted plasma proteins in the tumor stroma and the walls of vessels, but no such meshwork is detectable in normal tissues (Dvorak 1985; Abe 1999; Pilch 2006). The mesh-like pattern produced by the CREKA peptide in tumors prompted the study of whether clotted plasma proteins can be the target of this peptide. The peptide was tested in fibrinogen knockout mice, which lack the fibrin meshwork in their tumors. Like previously identified clot-binding peptides (Pilch 2006), intravenously injected CREKA peptide failed to accumulate in B16F1 melanomas grown in the fibrinogen null mice, but formed a brightly fluorescent meshwork in B16F1 tumors grown in normal littermates of the null mice (FIGS. 1A and B). In agreement with this result, the CREKA phage, but not the control insert-less phage, bound to clotted plasma proteins in vitro (FIG. 1C). These results establish CREKA as a clot-binding peptide. Its structure makes it an attractive peptide to use in nanoparticle targeting because, unlike other clot-binding peptides, which are cyclic 10 amino-acid peptides (Pilch 2006), CREKA is linear and contains only 5 amino acids. Moreover, the sulfhydryl group of the single cysteine residue is not required to provide binding activity and can be used to couple the peptide to other moieties.

Figure 6:
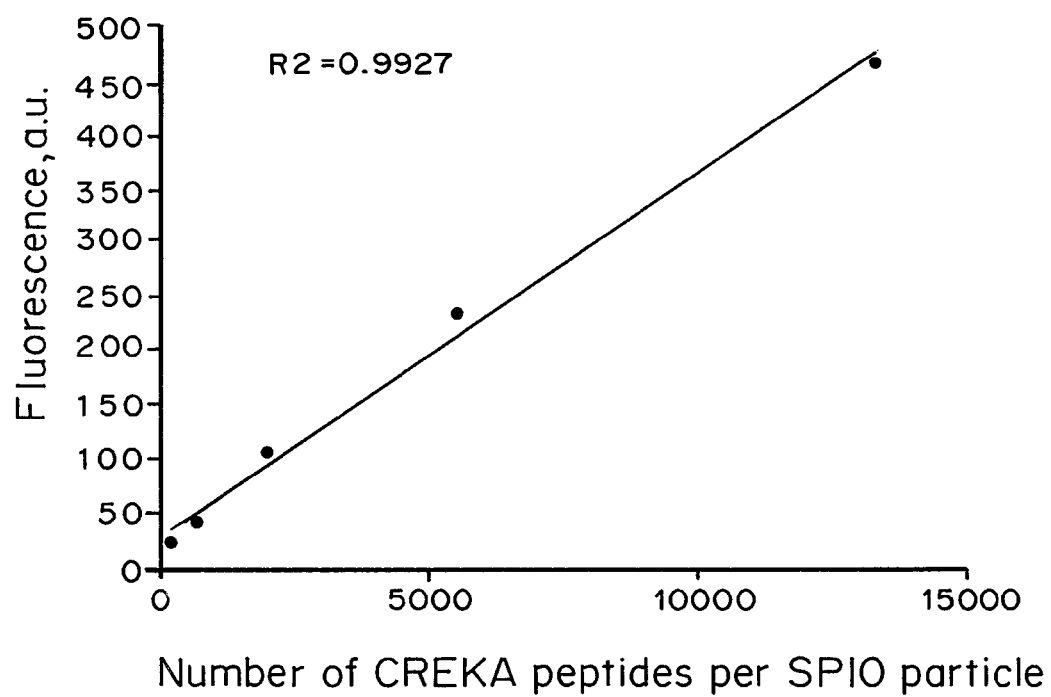
FIG. 6 shows fluorescence intensity of iron oxide nanoparticles (CREKA-SPIO) coupled to various levels of substitution with fluorescein-labeled CREKA peptide. Fluorescence emitted by the conjugated particles is linearly related to the level of substitution. A.U.=Arbitrary Units.

Peptide-coated nanoparticles. Fluorescein-labeled CREKA or fluorescein was coupled onto the surface of 50 nm superparamagnetic, amino dextran-coated iron oxide (SPIO) nanoparticles. Such particles have been extensively characterized with regard to their chemistry, pharmacokinetics, and toxicology, and are used as MRI contrast agents (Jung 1995; Jung 1995; Weissleder 1989). Coupling of the fluorescein-labeled peptides to SPIO produced strongly fluorescent particles. Releasing the peptide from the particles by hydrolysis increased the fluorescence further by a factor of about 3. These results indicate that the proximity of the fluorescein molecules at the particle surface causes some quenching of the fluorescence. Despite this, fluorescence from the coupled fluorescein peptide was almost linearly related to the number of peptide molecules on the particle (FIG. 6), allowing for the tracking of the number of peptide moieties on the particle by measuring particle fluorescence, and the use of fluorescence intensity as a measure of the concentration of particles in samples. CREKA-SPIO was used with at least 8,000 peptide molecules per particle in the in vivo experiments. The CREKA-SPIO nanoparticles bound to mouse and human plasma clots in vitro, and the binding was inhibited by the free peptide (FIG. 1D), The nanoparticles distributed along a fibrillar meshwork in the clots (inset in FIG. 1D). These results show that the particle-bound peptide retains its binding activity toward clotted plasma proteins.

Figure 2A:
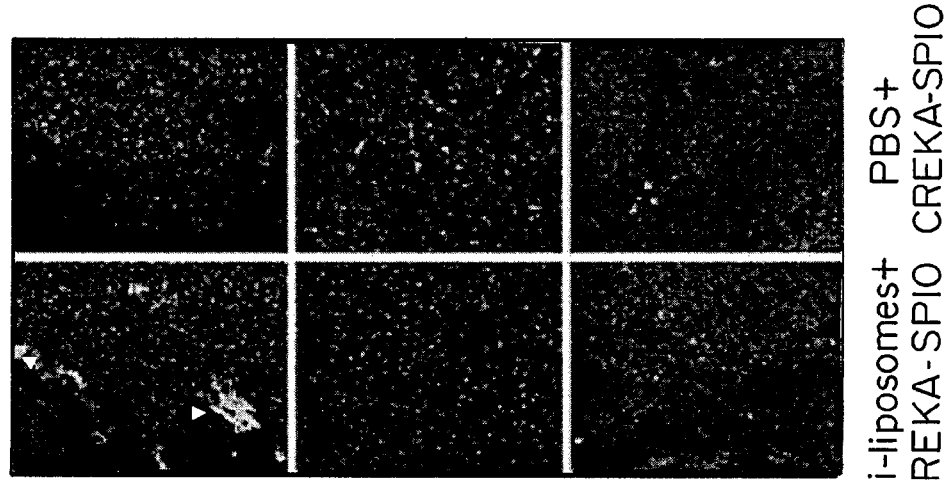
FIGS. 2A-2D show tumor homing of CREKA-conjugated iron oxide particles. CREKA-SPIO particles were intravenously injected (4 mg Fe/kg) into Balb/c nude mice bearing MDA-MB-435 human breast cancer xenograft tumors measuring 1-1.5 cm in diameter. The mice were sacrificed by perfusion 5-6 hours later and tissues were examined for CREKA-SPIO fluorescence (arrowhead). Nuclei were stained with DAPI (gray spots seen all over image). (A) Distribution of CREKA-SPIO in tissues from MDA-MB-435 tumor mice that received 2 hours earlier an injection of PBS (A, upper panels) or Ni/DSPC/CHOL liposomes (Ni-liposomes) containing 0.2 μmol Ni in 200 μl of PBS (A, lower panels). (B) Plasma circulation half-life of CREKA-SPIO following different treatments. At least 4 time points were collected. Data were fitted to mono-exponential decay using Prizm software (GraphPad, San Diego, Calif.), and the half-life values were compared in unpaired t-test (***$p<0.0001$, n=10). (C) Accumulation of CREKA-SPIO nanoparticles in tumor vessels. Mice were injected and tissues collected as in panel A. Fluorescent intravascular CREKA-SPIO particles overlap with iron oxide viewed in transmitted light. Magnification: 600×. (D) Control organs of Ni-liposome/CREKA-SPIO-injected mice. Occasional spots of fluorescence are seen in the kidneys and lungs. The fluorescence seen in the heart did not differ from uninjected controls, indicating that it is autofluorescence. Representative results from at least 3 independent experiments are shown. Magnification A and D, 200×; C, 600×.
Figure 2B:
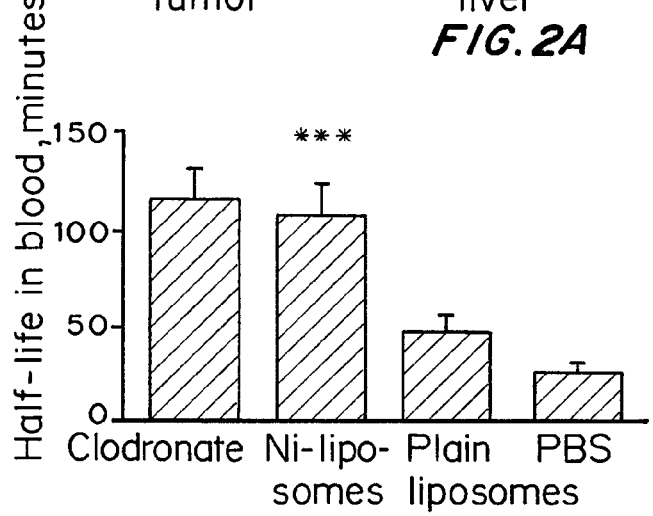

Tumor homing versus liver clearance of CREKA-SPIO. Initial experiments showed that intravenously injected CREKA-SPIO nanoparticles did not accumulate effectively in MDA-MB-435 breast cancer xenografts. In contrast, a high concentration of particles was seen in reticuloendothelial system (RES) tissues (FIG. 2A, upper panels). As the free CREKA peptide effectively homes to these tumors (FIG. 5), it was hypothesized that the RES uptake was a major obstacle to the homing of the nanoparticles. The role of the RES in the clearance of CREKA-SPIO was confirmed by depleting RES macrophages in the liver with liposomal clodronate (Van Rooijen 1994). This treatment caused about a 5-fold prolongation in particle half-life (FIG. 2B). Particulate material was eliminated from the circulation because certain plasma proteins bind to the particles and mediate their uptake by the RES (opsonization; Moghimi 2001; Moore 1997). Injecting decoy particles that eliminate plasma opsonins is another commonly used way of blocking RES uptake (Souhami 1981; Fernandez-Urrusuno 1996). Liposomes coated with chelated $Ni^{2+}$ were tested as a potential decoy particle because it was surmised that iron oxide and $Ni^{2+}$ would attract similar plasma opsonins, and Ni-liposomes could therefore deplete them from the systemic circulation. Indeed, SDS-PAGE analysis showed that significantly less plasma protein bound to SPIO in the blood of mice that had been pre-treated with Ni-liposomes.

Figure 1D:
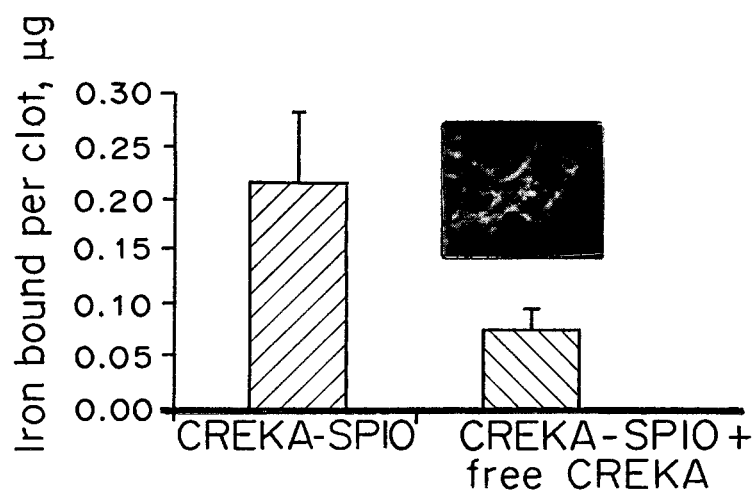
Figure 2C:
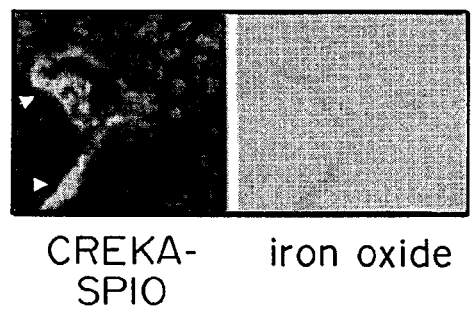
Figure 2D:
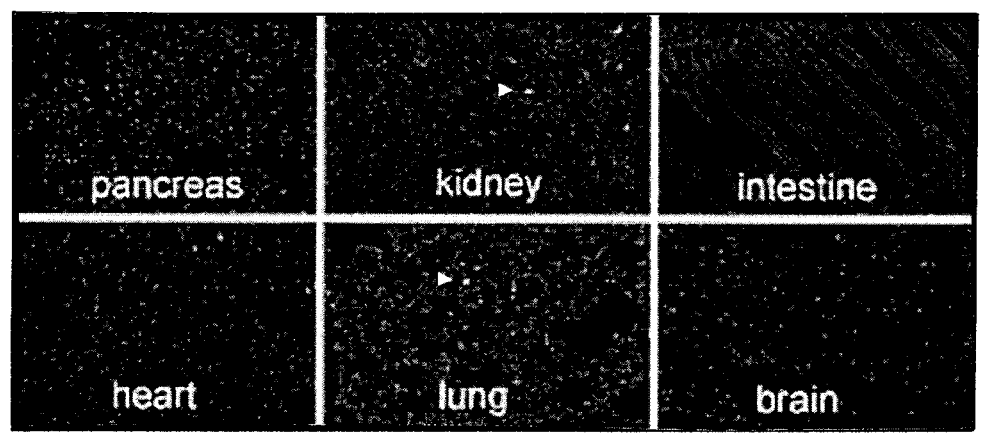

Intravenously injected Ni-liposomes prolonged the half-life of the SPIO and CREKA-SPIO in the blood by a factor of about 5 (FIG. 2B). The Ni-liposome pretreatment whether done 5 min or 48 h prior to the injection of CREKA-SPIO, greatly increased the tumor homing of the nanoparticles, which primarily localized in tumor blood vessels (FIG. 2A lower tumor panel and FIG. 2D). The local concentration of particles was so high that the brownish color of iron oxide was visible in the optical microscope (FIG. 2C, right panel), indicating that the fluorescent signal observed in tumor vessels was from intact CREKA-SPIO. Fewer particles were seen in the liver after the Ni-liposome pre-treatment, but accumulation in the spleen was unchanged or even enhanced (FIG. 2A). Other organs contained minor amounts of CREKA-SPIO particles or no particles at all, whether Ni-liposomes were used or not (FIG. 1D). Plain liposomes were tested as decoy particles. These liposomes prolonged the blood half-life and tumor homing of subsequently injected CKEKA-SPIO (FIG. 2B), showing the existence of a common clearance mechanism for liposomes and SPIO.

Figure 3C:
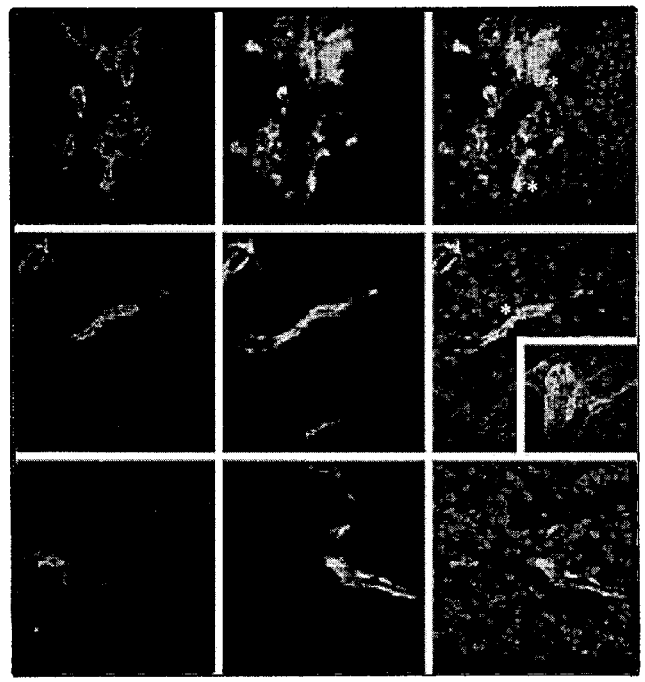
Figure 3C:
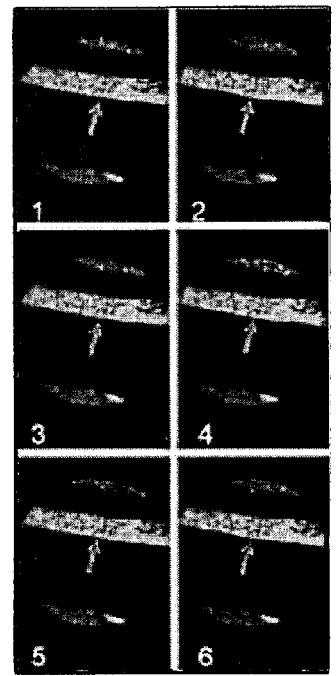
Figure 3C:
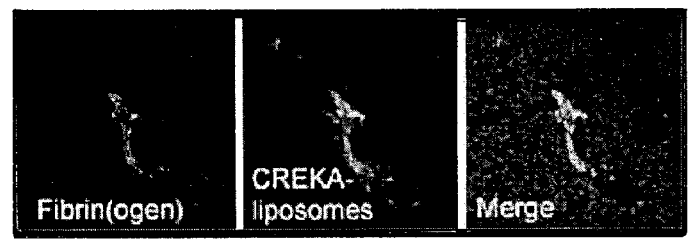

Nanoparticle-induced blood clotting in tumor vessels. CREKA-SPIO particles administered after liposome pre-treatment primarily colocalized with tumor blood vessels, with some particles appearing to have extravasated into the surrounding tissue (FIG. 3A, top panels). Significantly, up to 20% of tumor vessel lumens were filled with fluorescent masses. These structures stained for fibrin (FIG. 3A, middle panels), showing that they are blood clots impregnated with nanoparticles. In some of the blood vessels the CREKA-SPIO nanoparticles were distributed along a meshwork (inset), possibly formed of fibrin and associated proteins, and similar to the pattern shown in the inset of FIG. 1D.

Figure 7:
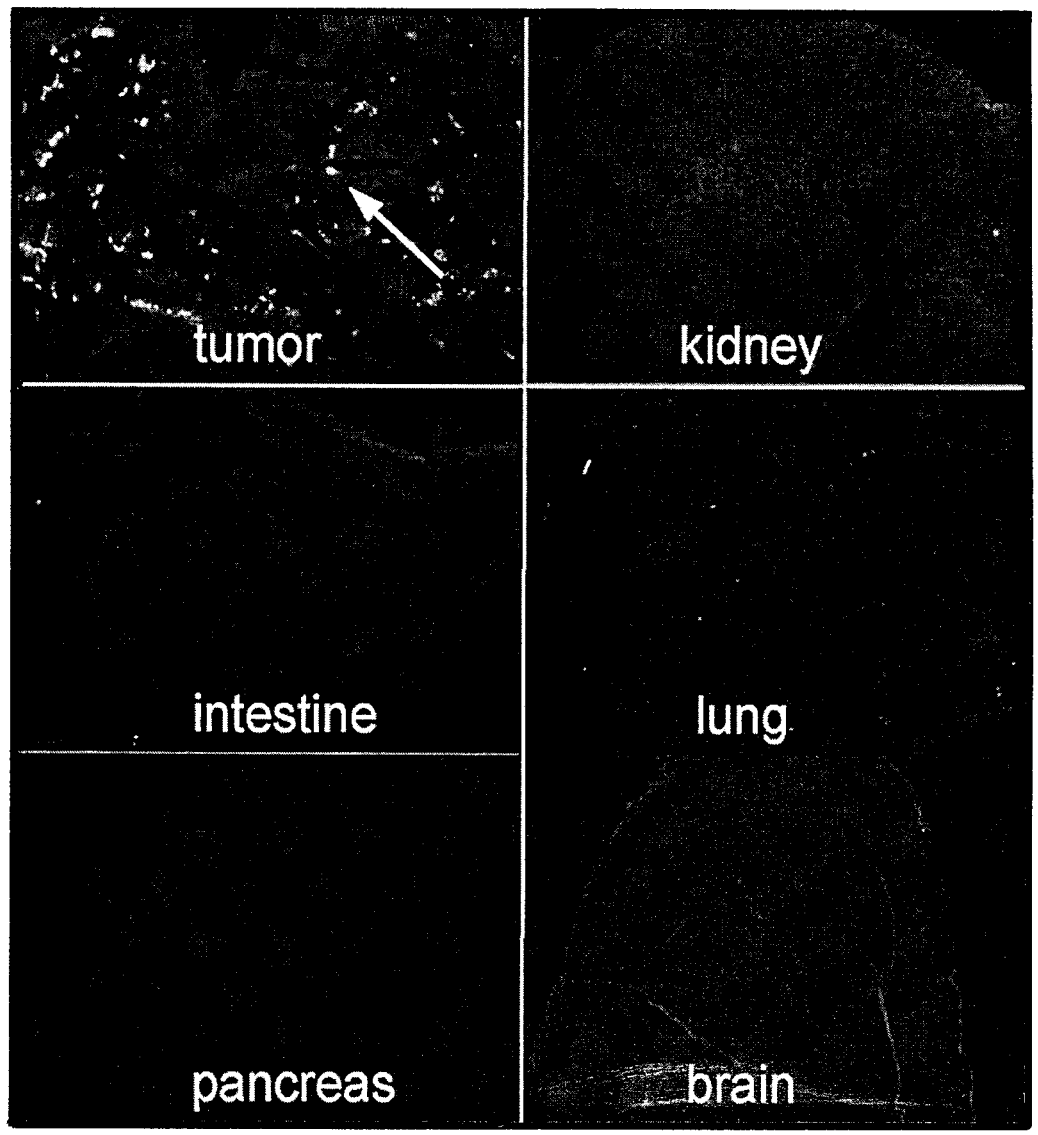
FIG. 7 shows CREKA-SPIO nanoparticles accumulate in tumor tissue, but not in non-RES normal tissues. The low magnification (40×) was used to produce these images because only blood vessels in which clotting had concentrated the CREKA-SPIO fluorescence (white spots) are visible at this magnification. Note the entrapment of nanoparticles in clots in tumor tissue (arrow), but not in non-RES normal tissues. The injections were carried out and the tissues prepared for analysis as in FIG. 2. A representative experiment out of 10 is shown.
Figure 8A:
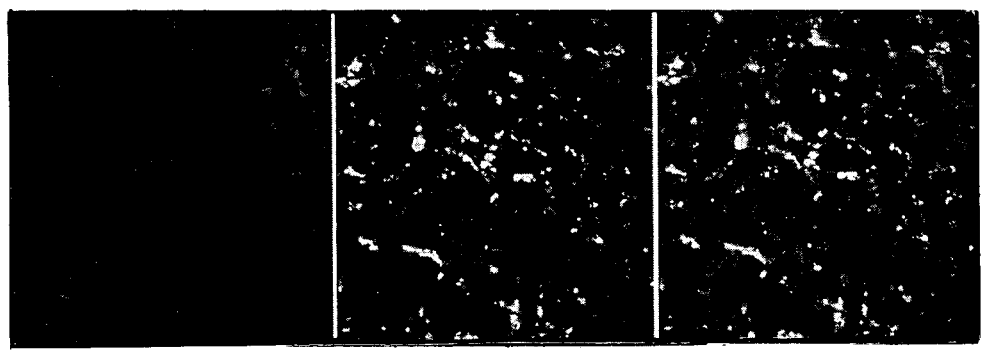
FIGS. 8A and 8B show lack of colocalization of fibrin (ogen) staining and CREKA-SPIO in the liver. The fibrin (ogen)-positive structures can be background from fibrinogen production by the liver, as it does not co-localize with the nanoparticles (A), and the liver from a non-injected mouse showed similar fibrin(ogen) staining (B). Magnification 600×.
Figure 8B:
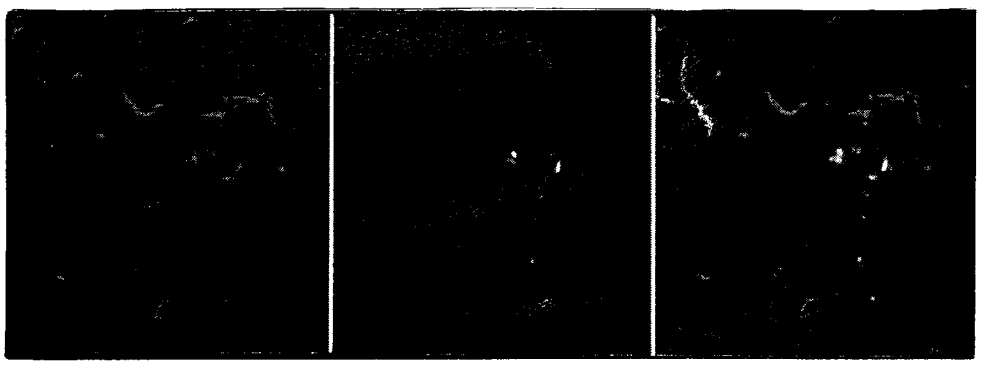

Among the non-RES tissues, the kidneys and lungs contained minor amounts of specific CREKA-SPIO fluorescence (FIG. 2D). However, low magnification images, which reveal only blood vessels with clots in them, showed no clotting in these tissues, with the exception of very rare clots in the kidneys (FIG. 7). Despite massive accumulation of nanoparticles in the liver no colocalization between fibrin(ogen) staining and CREKA-SPIO fluorescence in liver vessels (FIG. 8) was seen. Moreover, liver tissue from a non-injected mouse also stained for fibrin(ogen) (FIG. 8B), presumably reflecting fibrinogen production by hepatocytes. Thus, the clotting induced by CREKA-SPIO nanoparticles is essentially confined to tumor vessels.

Figure 9A:
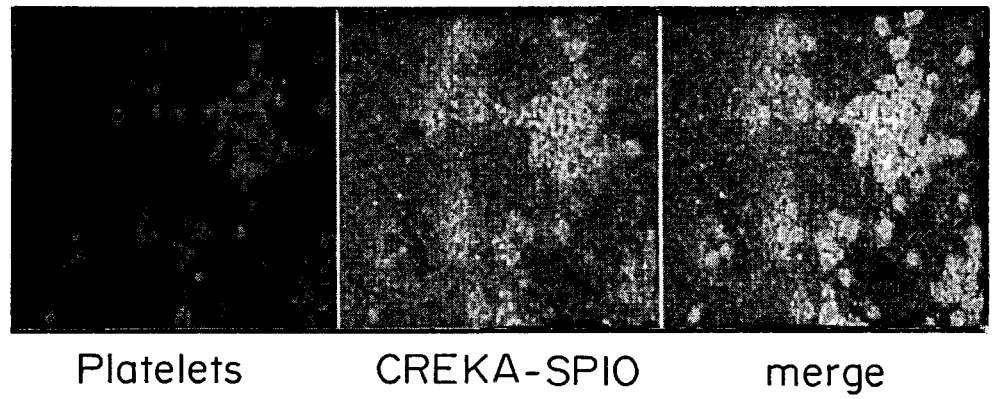
FIGS. 9A and 9B show the role of platelets in nanoparticle homing. (A). Blood was drawn 5 min post-injection of 4 mg/kg of CREKA-SPIO into mice and a 50 µl aliquot was run through a magnetic column. Bound CREKA-SPIO particles were eluted from the column, concentrated on a slide, and stained with anti-CD41 antibody. Some of the particles appear to be associated with platelets. (B). A low-magnification image (40×) showing CREKA-SPIO homing and clot formation in a tumor from a platelet-depleted mouse. Platelet depletion was accomplished by treating mice with 0.1 mg of an anti-CD41 monoclonal antibody as described (Van der Heyde and Gramaglia (2005)). The mice subsequently received Ni-liposomes/CREKA-SPIO as described in the legend of FIG. 2. The anti-platelet treatment did not decrease the incidence of fluorescent clots (compare with the tumor panel in FIG. 7).
Figure 9B:
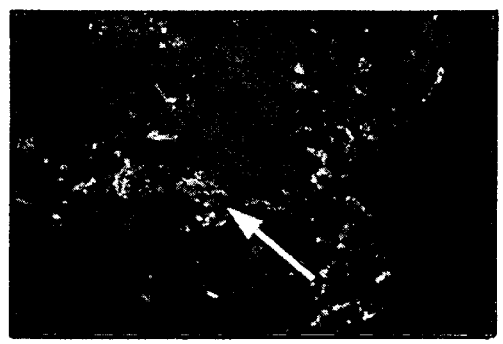

Nanoparticles can cause platelet activation and enhance thrombogenesis (Radomski 2005; Khandoga 2004). Some CREKA-SPIO nanoparticles (<1%) recovered from blood were associated with platelets (FIG. 9A), but staining for a platelet marker showed no colocalization between the platelets and CREKA-SPIO nanoparticles in tumor vessels (FIG. 3A, lower panels). Thrombocytopenia was also induced by injecting mice with an anti-CD41 monoclonal antibody (Van der Heyde 2005) and no noticeable effect on CREKA-SPIO homing to the MDA-MB-435 tumors was found (FIG. 9B). These results indicate that platelets are not involved in the homing pattern of CREKA-SPIO.

The deep infiltration of clots by nanoparticles showed that these clots must have formed at the time particles were circulating in blood, rather than before the injection. This was tested with intravital confocal microscopy, using DiI-labeled erythrocytes as a flow marker. There was time-dependent clot formation and obstruction of blood flow in tumor blood vessels with parallel entrapment of CREKA-SPIO in the forming clots (FIG. 3B).

It was next tested whether the clotting-inducing effect was specific for SPIO particles, or could be induced with a different CREKA-coated particle. Liposomes into which fluorescein-CREKA peptide was incorporated that was coupled to lipid-tailed polyethylene glycol (PEG) was used. Like CREKA-SPIO, the CREKA-liposomes selectively homed to tumors and co-localized with fibrin within tumor vessels (FIG. 3C), showing that CREKA liposomes are also capable of causing clotting in tumor vessels. No clotting was seen when control SPIO or control liposomes were injected in the tumor mice.

Clotting-amplified tumor targeting. The contribution of clotting to the accumulation of CREKA-SPIO in tumor vessels was also studied. Quantitative analysis of tumor magnetization with a Superconducting Quantum Interference Device (SQUID) (FIG. 4A) and measurement of the fluorescence signal revealed about 6-fold greater accumulation of CREKA-SPIO in Ni-liposome-pretreated mice compared to PBS-pretreated mice. Aminated SPIO control particles did not significantly accumulate in the tumors (FIG. 4A).

Figure 4A:
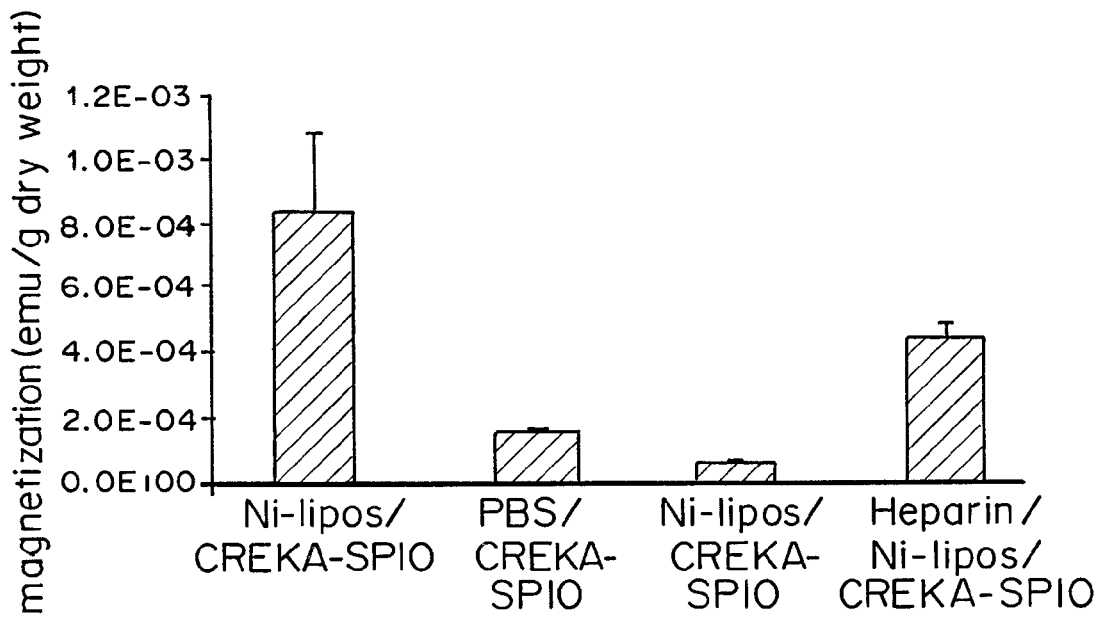
FIGS. 4A-4D show the effect of blood clotting on nanoparticle accumulation in tumors. Mice bearing MDA-MB-435 human breast cancer xenografts were intravenously injected with PBS or a bolus of 800 U/kg of heparin followed 120 min later by Ni-liposomes (or PBS) and CREKA-SPIO (or control nanoparticles). The mice received additional heparin by intraperitoneal injections (a total of 1000 U/kg) or PBS throughout the experiment. (A) Tumors were removed 6 hours after the nanoparticle injection, and magnetic signal in the tumor after different treatments was determined with SQUID. Aminated dextran SPIO served as a particle control (control SPIO). SPIO nanoparticle concentration in tissues is represented by the saturation magnetization value (electromagnetic unit, emu) of the tissue at 1T magnetic field after the subtraction of the diamagnetic and the paramagnetic background of blank tissue. The magnetization values were normalized to dry weight of the tissue. Results from 3 experiments are shown. (B) A representative example of the appearance of CREKA-SPIO particles in tumor vessels of mice treated with heparin. (C) Quantification of heparin effect on clotting in blood vessels. Mice were pretreated with PBS (white bars) or heparin (black bars) as described above, followed by Ni liposomes/CREKA-SPIO nanoparticles. Three sections from two tumors representing each treatment were stained with anti-CD31 for blood vessels, and the percentage of vessels positive for fluorescence and fluorescent clots was determined. Note that heparin did not significantly change the percentage of blood vessels containing particles, but dramatically decreased the incidence of the lumens that are filled with fluorescence. (D) Near-infrared imaging of mice that received Ni-liposomes followed by Cy7-labeled CREKA-SPIO with or without heparin pretreatment. The images were acquired 8 hours after the injection of the CREKA-SPIO particles using an Odyssey 2 NIR scanner (Li-COR Biosciences, Lincoln, Nebr.). The images shown are composites of 2 colors, gray (700 nm channel, body and chow autofluorescence) and white (800 nm channel, Cy7). Arrows point to the tumors, arrowheads to the liver. Note the strong decrease in signal from the tumor in the heparin-pretreated mouse. A representative experiment out of 3 is shown.
Figure 4B:
Figure 4D:
Figure 4C:
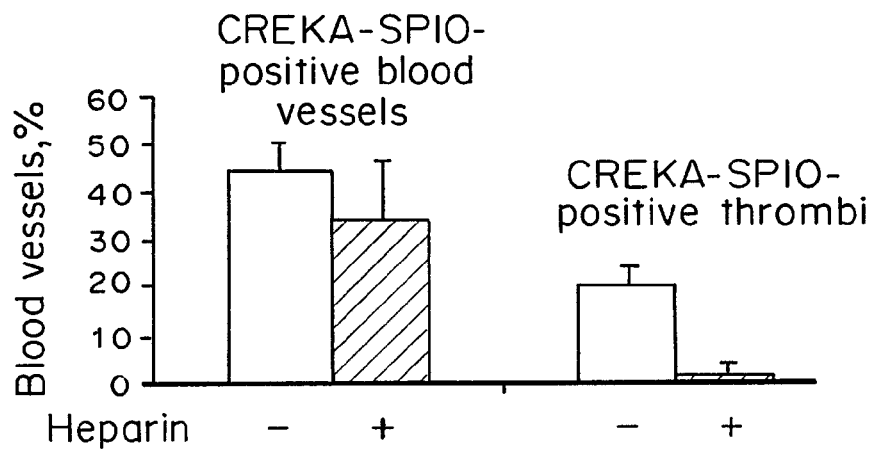

The SQUID measurements revealed that injecting heparin, which is a strong clotting inhibitor, prior to injection of CREKA-SPIO, reduced tumor accumulation of nanoparticles by more than 50% (FIG. 4A). Microscopy showed that heparin reduced the fibrin-positive/CREKA-SPIO positive structures within tumor vessels, but that the particles still bound along the walls of the vessels, presumably to preexisting fibrin deposits (a representative image is shown in FIG. 4B). Separate quantification of the homing pattern showed that heparin did not significantly reduce the number of vessels with nanoparticles bound to the vessel walls, but essentially eliminated the intravascular clotting (FIG. 4C). Thus, the binding of CREKA-SPIO to tumor vessels does not require the clotting activity that is associated with these particles, but clotting improves the efficiency of the tumor homing.

The clotting induced by CREKA-SPIO caused a particularly strong enhancement of tumor signal in whole-body scans. CREKA-SPIO nanoparticles labeled with Cy7, a near infrared fluorescent compound, effectively accumulated in tumors (FIG. 4D, image on the left, arrow), with a significant signal from the liver as well (arrowhead). The reduction in the tumor signal obtained with heparin (FIG. 4D, image on the right) appeared greater in the fluorescence measurements than the 50% value determined by SQUID, possibly because the concentrated signal from the clots enhanced optical detection of the fluorescence. These results show that the clotting induced by CREKA-SPIO provides a particular advantage in tumor imaging.

2. Discussion

This example describes an example of a nanoparticle system that provides effective accumulation of the particles in tumors. The system is based on four elements: First, coating of the nanoparticles with a tumor-homing peptide that binds to clotted plasma proteins endows the particles with a specific affinity for tumor vessels (and tumor stroma). Second, decoy particle pretreatment prolongs the blood half-life of the particles and increases tumor targeting. Third, the tumor-targeted nanoparticles cause intravascular clotting in tumor blood vessels. Fourth, the intravascular clots attract more nanoparticles into the tumor, amplifying the targeting.

A peptide with specific affinity for clotted plasma proteins was chosen as the targeting element for the nanoparticles. The interstitial spaces of tumors contain fibrin and proteins that become cross-linked to fibrin in blood clotting, such as fibronectin (Dvorak 1985; Pilch 2006). The presence of these products in tumors, but not in normal tissues, can be a result of leakiness of tumor vessels, which allows plasma proteins to enter from the blood into tumor tissue, where the leaked fibrinogen is converted to fibrin by tissue procoagulant factors (Dvorak 1985; Abe 1999). The clotting creates new binding sites that can be identified and accessed with synthetic peptides (Pilch 2006). The present results show that the CREKA-modified nanoparticles not only bind to blood and plasma clots, but can also induce localized tumor clotting. The nature of the particle is not limited for this activity, as it was found that both CREKA-coated iron oxide and micron-sized CREKA-coated liposomes cause clotting in tumor vessels. The binding of one or more clotting products by the CREKA-modified particles can shift the balance of clotting and clot dissolution in the direction of clot formation, and the presence of this activity at the surface of particles can facilitate contact-dependent coagulation.

Some nanomaterials are capable of triggering systemic thrombosis (Gorbet 2004), but here the thrombosis induced by the CREKA particles was confined to tumor vessels. The high concentration of the targeted particles in tumor vessels can explain the selective localization of the thrombosis to tumor vessels. However, since no detectable clotting was seen in the liver, where the nanoparticles also accumulate at high concentrations, other factors must be important. The procoagulant environment common in tumors can be a major factor contributing to the tumor specificity of the clotting (Boccaccio 2005).

A major advantage of nanoparticles is that multiple functions can be incorporated onto a single entity. Described herein is an in vivo function for nanoparticles; self-amplifying tumor homing enabled by nanoparticle-induced clotting in tumor vessels and the binding of additional nanoparticles to the clots. This nanoparticle system combines several other functions into one particle: specific tumor homing, avoidance of the RES, and effective tumor imaging. Optical imaging was used in this work, but the JO platform also enables MRI imaging. The clotting caused by CREKA-SPIO nanoparticles in tumor vessels serves to focally concentrate the particles in a manner that appears to improve tumor detection by microscopic and whole-body imaging techniques.

Another function of the targeted particles is that they cause physical blockade of tumor vessels by local embolism. Blood vessel occlusion by embolism or clotting can reduce tumor growth (Huang 1997; El-Sheikh 2005). To date, a 20% occlusion rate in tumor vessels has been achieved. Due to the modular nature of nanoparticle design, the functions described herein can be incorporated into particles with additional activities. Drug-carrying nanoparticles that accumulate in tumor vessels and slowly release the drug payload while simultaneously occluding the vessels can be used with the methods and compositions disclosed herein.

3. Materials and Methods

Phage screening, tumors and peptides. In vivo screening of a peptide library with the general structure of $CX_7C$ (SEQ ID NO: 4), where C is cysteine and X is any amino acid, was carried out as described (Oh 2004) using 65- to 75-day-old transgenic MMTV PyMT mice (Hutchinson 2000). These mice express the polyoma virus middle T antigen (MT) under the transcriptional control of the mouse mammary tumor virus (MMTV), leading to the induction of multi-focal mammary tumors in 100% of carriers. MDA-MB-435 tumors in nude mice and peptide synthesis have been described (Laakkonen 2002; Laakkonen 2004). B16F1 murine melanoma tumors were grown in fibrinogen null mice (Suh 1995) and their normal littermates and used when they reached 0.5-1 cm in size (Pilch 2006).

Nanoparticles and liposomes. Amino group-functionalized dextran-coated superparamagnetic iron oxide nanoparticles (50 nm nanomag-D-SPIO; Micromod Partikeltechnologie GmbH, Rostock, Germany) were coupled with CREKA peptide using a crosslinker. The final coupling ratio was 30 nmol fluorescein-labeled peptide molecules per mg iron oxide, or 8,000 peptides/particle. For near-infrared labeling with Cy7, about 20% of the amines were derivatized with Cy7-NHS ester (GE Healthcare Bio-Sciences, Piscataway, N.J.), and the remaining amines were used for conjugating the peptide. Detail on the SPIO and the preparation of liposomes are described below. Clodronate was purchased from Sigma and incorporated into liposomes as described (Van Rooijen and Sanders (1994)).

Nanoparticle injections. For intravenous injections, the animals were anesthetized with intraperitoneal Avertin, and liposomes (2 μmol DSPC) and/or nanoparticles (1-4 mg Fe/kg body weight) were injected into the tail vein. The animals were sacrificed 5-24 h post-injection by cardiac perfusion with PBS under anesthesia, and organs were dissected and analyzed for particle homing. To suppress liver macrophages, mice were intravenously injected with liposomal clodronate suspension (100 μl per mouse), and the mice were used for experiments 24 hours later.

Phage and nanoparticle binding to clots. Phage binding to clotted plasma proteins was determined as described (Pilch 2006). CREKA-SPIO and control SPIO were added to freshly formed plasma clots in the presence or absence of free CREKA peptide. After 10 min incubation, the clots were washed 4 times in PBS, transferred to a new tube and digested in 100 μl concentrated nitric acid. The digested material was diluted in 2 ml distilled water and the iron concentration was determined using inductively coupled plasma-optical emission spectroscopy (ICP-OES, PerkinElmer, Norwalk, Conn.).

Nanoparticle preparation. When necessary to achieve high peptide coupling density, additional amino groups were added to commercially obtained SPIO as follows: First, to crosslink the particles before the amination step, 3 ml of the colloid (~10 mgFe/ml in double-distilled water) was added to 5 ml of 5M NaOH and 2 ml of epichlorohydrin (Sigma, St. Louis, Mo.). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford Ill.). Amino groups were added to the surface of the particles as follows: 0.02 ml of concentrated ammonium hydroxide (30%) was added to 1 ml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn Calif.), rinsed with PBS three times, and eluted from the column with 1 ml PBS.

To conjugate CREKA peptide to SPIO, the particles were re-suspended at a concentration of 1 mg Fe/ml, and heterobifunctional linker N-[a-maleimidoacetoxy]succinimide ester (AMAS; Pierce) was added (2.5 mg linker per 2 mg Fe) under vortexing. After incubation at room temperature for 40 min, the particles were washed 3 times with 10 ml PBS on a MACS column. The peptide with free terminal cysteine was then added (100 μg peptide per 2 mg Fe). After incubation overnight at 4° C. the particles were washed again and re-suspended in PBS at a concentration of 0.35 mg/ml of Fe). To quantify the number of peptide molecules conjugated to the particles, a known amount of stock or AMAS-activated particles was incubated with varying amounts of the peptide. After completion of the incubation the particles were pelleted at 100.000 G using Beckman TLA 100.3 ultracentrifuge rotor (30 min) and the amount of the unbound peptide was quantified by fluorescence. To cleave the conjugated peptide from the particles, the particles were incubated at 37° C. overnight at pH 10. The concentration of free peptide in the supernatant was determined by reading fluorescence and by using the calibration curve obtained for the same peptide. The fluorescence intensity of known amounts of particles was plotted as a function of peptide conjugation density, and the slope equation was used to determine conjugation density in different batches.

Liposome preparation. To prepare liposomes, 1,2-Distearoyl-sn-glycero-3-phosphocholine (DSPC), cholesterol, and 1,2-Dioleoyl-sn-glycero-3-{[N(5-amino-1-carboxypentyl) iminodiacetic acid]succinyl} (nickel salt) (all from Avanti Polar Lipids, Alabaster Ala.), were mixed in chloroform at a molar ratio of 57:37:10 and evaporated in a rotary evaporator until dry. The lipids were hydrated in PBS to a final DSPC concentration 10 mM. The lipid mixture was extensively bath sonicated for 10 min at 55° C. to facilitate liposome formation. For plain liposomes only DSPC and cholesterol were used at a molar ratio of 57:37.

CREKA-decorated liposomes were prepared by reacting PEG-DSPE-maleimide (Avanti) with a 2-fold molar excess of CREKA. The reaction was performed at room temperature under nitrogen in PBS buffer, pH 7.4. After the reaction had been completed in 2 hours, the product (yellow precipitate) was washed by centrifugation and dissolved in ethanol. The ethanol solution was stored at −20° C. CREKA-PEG was incorporated by adding a liposome suspension to a dried film of CREKA-PEG-DSPE, heating to 55° C. while vortexing for 1 hour. Control liposomes were prepared as above but using FITC-PEG-DSPE instead. The liposome preparations were kept at 4° C. until used.

Analysis of protein binding by nanoparticles. To test the binding of soluble plasma proteins to SPIO nanoparticles, the particles were incubated with citrated mouse plasma at a concentration of 1-2 mg iron/ml plasma. Alternatively, the particles were injected into animals and plasma was collected 5-10 min post-injection. The particles were washed on the magnetic column to remove non-bound proteins, and the particles were boiled in 10% SDS for 20 min. The iron oxide was pelleted by ultracentrifugation (100.000 g, 10 min) and the eluted proteins in the supernatant were precipitated with acetone overnight at −20° C. The protein pellet was analyzed by SDS-PAGE, and the gels were silver stained (SilverQuest, Invitrogen, Carlsbad, Calif.). For mass spectrometric analysis, proteins extracted from the particles were reconstituted in water; a protein aliquot was digested with trypsin and analyzed using Applied Biosystems PE SCIEX QSTARR liquid chromatograph Q-TOF mass spectrometer, Foster City, Calif. The data were analyzed using Mascot search engine (Matrix Science, Boston, Mass.).

Nanoparticle clearance. Heparinized capillaries were used to draw 50 µA of blood from the periorbital plexus at different times after nanoparticle injection, the blood was centrifuged at 300 g for 2 min, and a 10 µA aliquot of platelet-rich plasma was diluted into 600 µl 1M Tris solution, pH 8.4. Fluorescence was determined on a PerkinElmer (Norwalk, Conn.) LS50B spectrofluorometer, and plotted as a function of the time the particles had circulated.

Intravital microscopy. Tumor blood flow in MDA-MB 435 xenograft-bearing mice was observed by intravital microscopy. Mice were pre-injected with Ni-liposomes and $5 \times 10^8$ of DiI-labeled erythrocytes. A skin flap was moved aside to expose the tumors, and the mice were intravenously injected with 4 mg/kg of fluorescein-CREKA-SPIO (time "0"). The tumors were scanned with IV-100 intravital laser scanning microscope (Olympus Corp., Tokyo, Japan) using an IV-OB35F22W29 MicroProbe objective (Olympus Corp., Tokyo, Japan). Movies were recorded at 10 min intervals up to 120 min post-injection.

Magnetic measurements of the tissue samples using Superconducting Quantum Interference Device (SQUID) magnetometer. Tissue samples were frozen immediately upon collection, lyophilized, weighed, and placed in gelatin capsules. The capsules were inserted into the middle of transparent plastic straws for magnetic measurements made using a Quantum Design MPMS2 SQUID magnetometer (San Diego, Calif.) operated at 150 K. The samples were exposed to direct current magnetic fields in stepwise increments up to one Tesla. Corrections were made for the diamagnetic contribution of tissue, capsule and straw.

B. Example 2

Nanoparticle-Induced Vascular Blockade in Tumors

Iron oxide particles (nanoworms; SPIO) coated with the tumor-homing peptide CREKA (SEQ ID NO:1) specifically home to tumor vessels which contain clotted plasma proteins recognized by this peptide. The CREKA particles cause additional clotting, which amplifies the tumor homing. The amplification greatly enhances tumor imaging, but did not cause enough clotting in tumor vessels to inhibit tumor growth as much as desired. Chemical modifications to the CREKA (SEQ ID NO:1), such as methylation, was shown to further increase the efficiency of the system to achieve a level of blood vessel occlusion in a prostate cancer model that does inhibit tumor growth. Also, by incorporating one or more other tumor-homing compounds or clot-binding compounds in conjunction with the chemically modified CREKA peptide the level of blood vessel occlusion could be further amplified.

1. Results

As discussed in Example 1 iron oxide particles coated with CREKA (SEQ ID NO:1) is a tumor-homing system. CREKA can be chemically modified to enhance the tumor homing activity.

Experiments showed that intravenously injected CREKA-SPIO nanoparticles effectively home to 22Rv-1 tumors in mice. The spleen and liver were the only non-tumor tissues that contained significant CREKA-SPIO fluorescence due to non-specific uptake of nanoparticles.

The tumor homing can be improved in the CREKA-SPIO system using several different approaches. For instance, the homing activity can be enhanced by chemical modification of the CREKA peptide. Another example for improving the homing activity of the system is combining CREKA or a chemically modified CREKA peptide with another tumor-homing or clot-binding peptides on the SPIO.

Methylated CREKA was shown to enhance the homing activity. The methylation of CREKA can be done on each amino acid independently either as N-methylation or C-methylation (also known as α-methylation). The methylated or non-methylated CREKA peptides studied here include CREKA, C(NMe)REKA, CR(NMe)EKA, CR(CMe)EKA, CRE(NMe)KA, CRE(CMe)KA, and CR(NMe)E(NMe). Each of the listed CREKA peptides can be combined with one or more other tumor-homing compound on SPIO. Tumor-homing compounds tested with CREKA peptides were CRKDKC (SEQ ID NO:5) and CGKRK (SEQ ID NO:7).

The enhanced CREKA peptide increased the homing of SPIO to tumor blood vessels, particularly to vessels the in tumor interior. Another tumor blood vessel-homing peptide was combined with CREKA on SPIO. As many as 70% of tumor blood vessels were positive for nanoparticle fluorescence when we injected a mixture of SPIO conjugated with CREKA together with SPIO conjugated with a different tumor-homing peptide. Both treatments increased the number of tumor vessels blocked by clotting with no increase in clotting within vessels in normal tissues. The treatment produced a highly significant reduction in tumor growth.

Figure 10A:
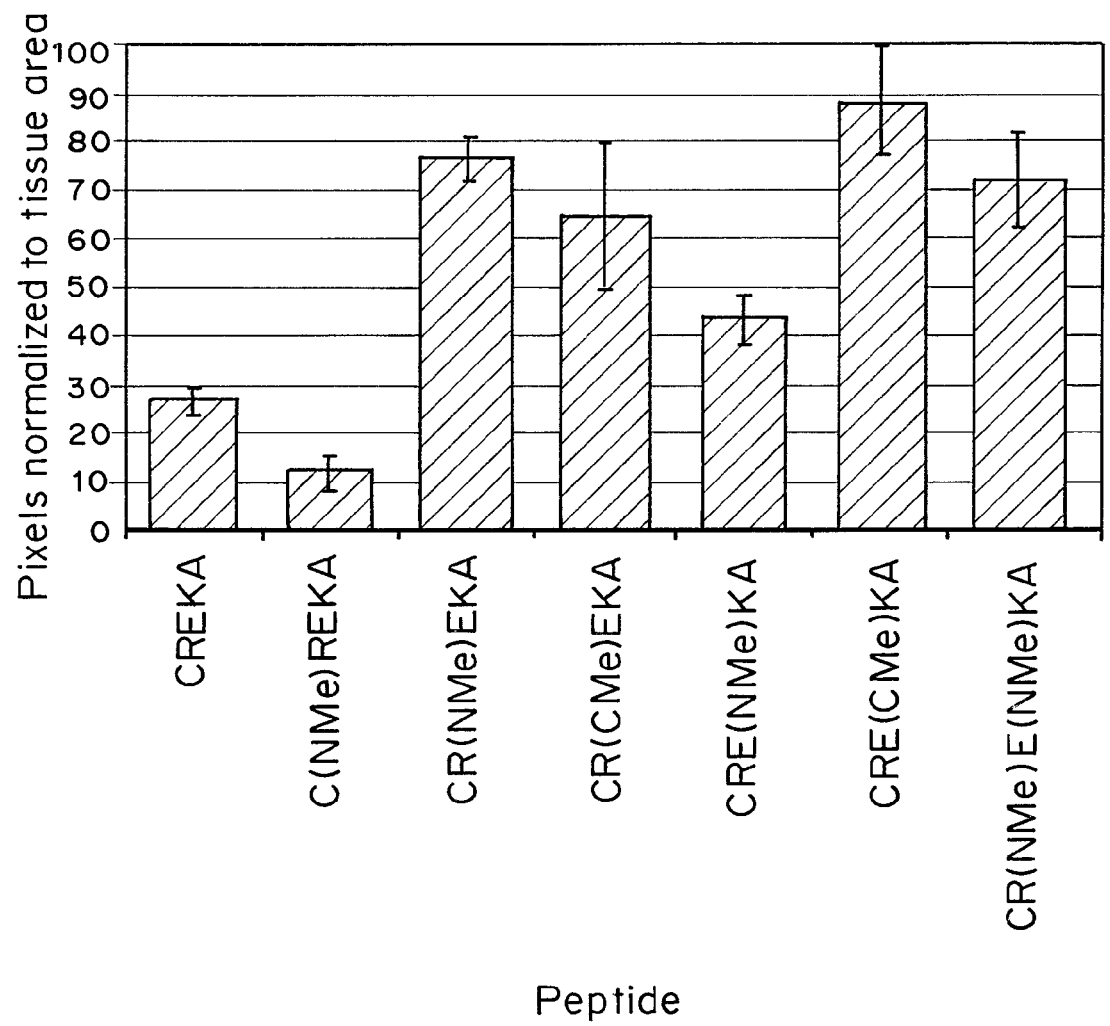
FIGS. 10A and 10B show tumor accumulation of CREKA peptide and its N-methylated and C-methylated variants. Mice bearing orthotropic 22Rv-1 xenograft tumors were intravenously injected with 200 µg of FAM-conjugated CREKA or methylated CREKA peptides. The peptides were allowed to circulate for 3 hrs. The mice were then perfused through the heart with PBS, and organs were collected and viewed under UV light.
Figure 10B:
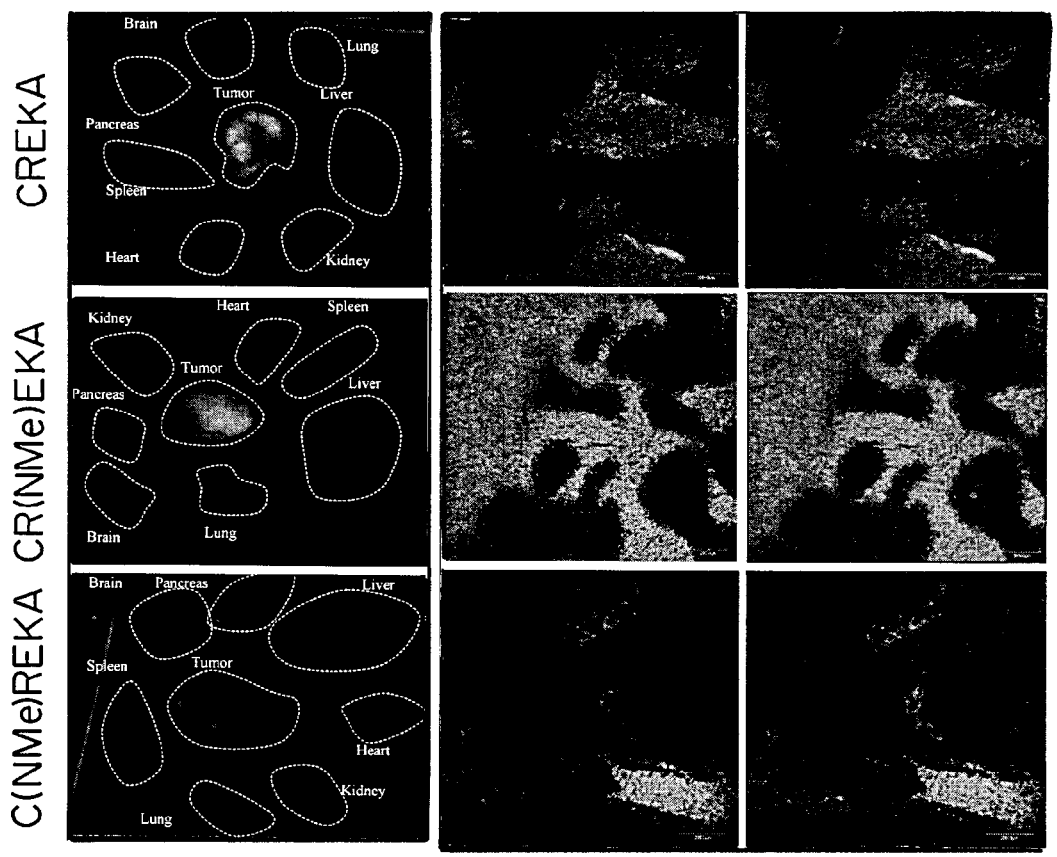

Tumor accumulation of CREKA peptide and its N-methylated and C-methylated variants. The accumulation of N-methylated and C-methylated derivatives of CREKA was measured in mice bearing orthotropic 22Rv-1 xenograft tumors. The mice were intravenously injected with 200 µg of FAM-conjugated CREKA or methylated CREKA peptides derivatives. The peptides were allowed to circulate for 3 hrs. The mice were then perfused through the heart with PBS, and organs were collected and the fluorescence was measured under UV light. The fluorescence was analyzed with Image J software. Most N/C-methylated CREKA analogs produced stronger fluorescence compared to the unmodified CREKA. CR(NMe)EKA, CR(CMe)EKA, CRE(NMe)KA, CRE(CMe)KA, and CR(NMe)E(NMe) all showed significantly more fluorescence compared to CREKA. C(NMe)REKA was the only methylated CREKA that did not show an enhanced fluorescence compared to the unmodified CREKA (see FIG. 10A). In FIG. 10B the enhanced fluorescence of CR(NMe) EKA is shown in the tumor compared to both CREKA and C(NMe)REKA peptide. It is shown that FAM-labeled CREKA peptide in which the glutamic acid is N-methylated accumulates in tumor tissue more strongly than unmodified CREKA.

Figure 11:
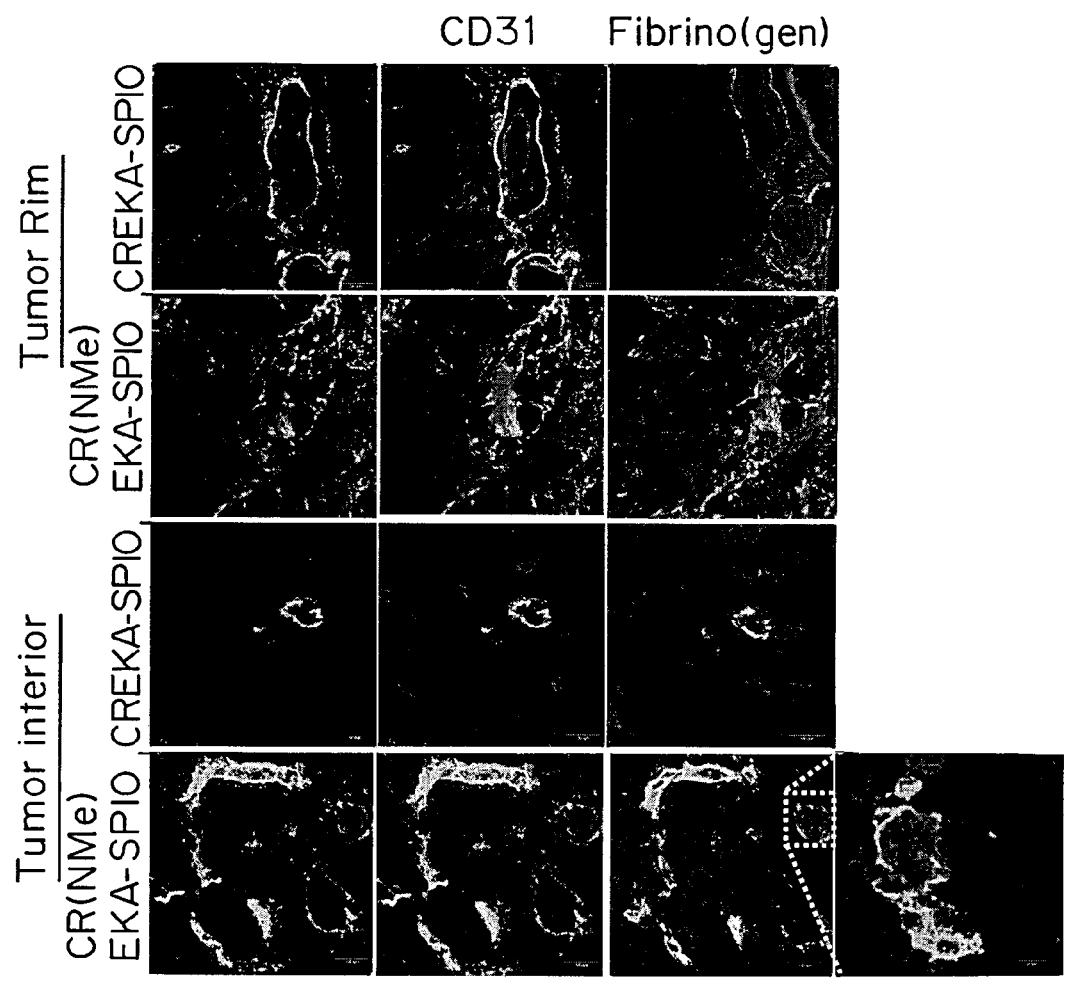
FIG. 11 shows N-methylated CREKA peptide improves the homing of iron oxide nanoworms to blood vessels in tumor interior. Nanoworms coated with FAM-labeled CREKA peptide or its N-methylated variant, were intravenously injected into nude mice bearing 22Rv-1 orthotropic human prostate cancer tumors. Tumors were harvested 5 hrs later, and tumor sections were stained with anti-CD-31 or anti-fibrino(gen) and examined by confocal microscopy. CREKA-coated nanoworms cause clotting in tumor vessels and amplify their own homing (Simberg et al., 2006). The N-methyl compound is more effective than the unmodified peptide, particularly in accumulating in the interior of tumors and inducing clotting. Magnification ×200. The lower right panel shows a high magnification (×400) view of the dotted area in the nearby panel. Peptide-conjugated particles are visible; blood vessels and clotting were separately visualized with anti-CD31 or anti-fibrin(ogen) staining.

N-methylated CREKA peptide improves the homing of iron oxide nanoworms to blood vessels in tumor interior. The accumulation of nanoworms coated with the FAM-labeled N-methylated derivative of CREKA and unmodified CREKA was measured in nude mice bearing 22Rv-1 orthotropic human prostate cancer tumors. The mice were intravenously injected with FAM-labeled CREKA peptide or its N-methylated variant. The peptides were circulated for 5 hrs and the tumors were harvested thereafter. The tumor sections were stained with anti-CD-31 or anti-fibrino(gen) and examined by confocal microscopy. CREKA-coated nanoworms cause clotting in tumor vessels and amplify their own homing (Simberg et al., *Proc. Natl. Acad. Sci. USA* 104: 932-936 (2007)). The N-methyl compound was shown to be more effective than the unmodified peptide, particularly in accumulating in the interior of tumors and inducing clotting (see FIG. 11).

Figure 12A:
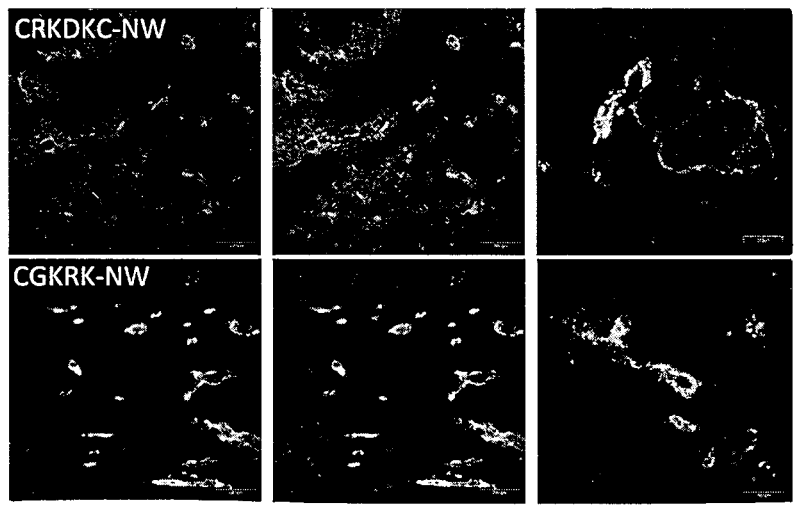
FIGS. 12A-12C show that combination of CREKA with another tumor-homing peptide enhances the efficiency of homing and CREKA-induced clotting.
Figure 12B:
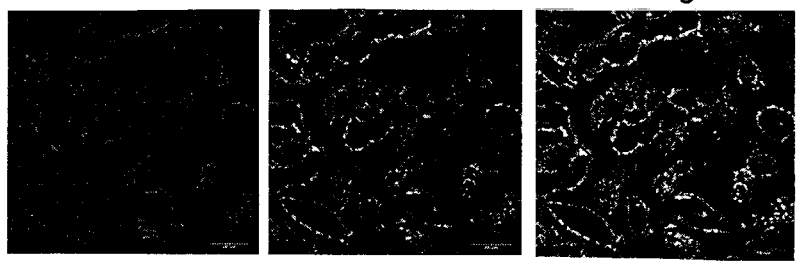
Figure 12B:
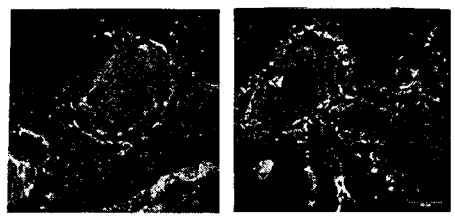
Figure 12C:
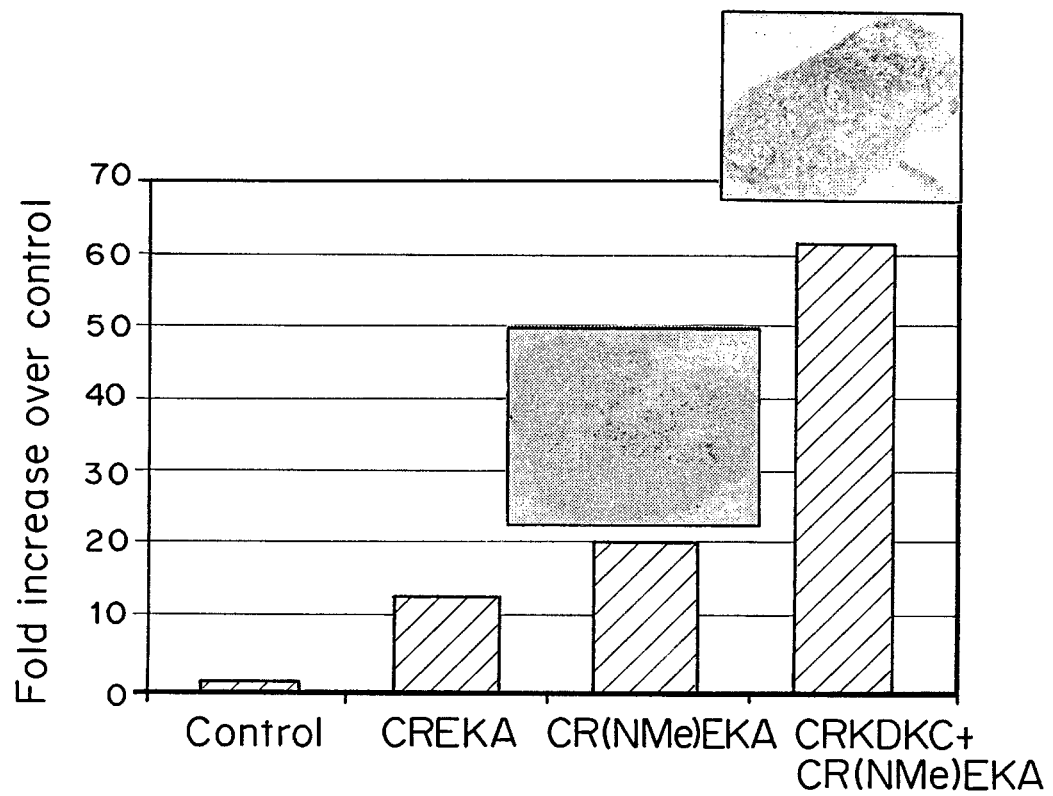

A combination of CREKA with another tumor-homing peptide enhances the efficiency of homing and CREKA-induced clotting. Iron oxide nanoworms coated with FAM-labeled CRKDKC (SEQ ID NO:5) or CGKRK (SEQ ID NO:7) were intravenously injected into nude mice bearing 22Rv-1 orthotopic human prostate cancer tumors. Tumors were harvested 5 hrs later, and tumor sections were stained with anti-CD-31 and examined by confocal microscopy. A mixture of nanoworms coated with FAM-labeled CRKDKC peptide (green) and rhodamine-labeled CREKA peptide was intravenously injected (2.5 mg Fe/kg of each nanoworm preparation) into nude mice bearing 22Rv-1 tumors, and tissues were harvested 5 hrs later. Tumor sections were stained with anti-CD-31 and anti-fibrino(gen), and examined by confocal microscopy. The magnification is ×100 (400× in the right lower panel). Nuclei were stained with DAPI. Cryosections of 22Rv-1 orthotopic tumor from mice injected with PBS, or nanoworms coated with CREKA or CR(NMe)EKA, or a mixture of CRKDKC and CREKA nanoworms were immunohistochemically stained with an anti-fibrino(gen) antibody. The sample were subjected to image analysis with Scanscope to quantify fibrino(gen)-positive areas. The results show that the combination of methylated CREKA with another tumor-homing peptide CRKDKC (SEQ ID NO:5) enhances the efficiency of homing and CREKA-induced clotting (see FIG. 12C).

Figure 13A:
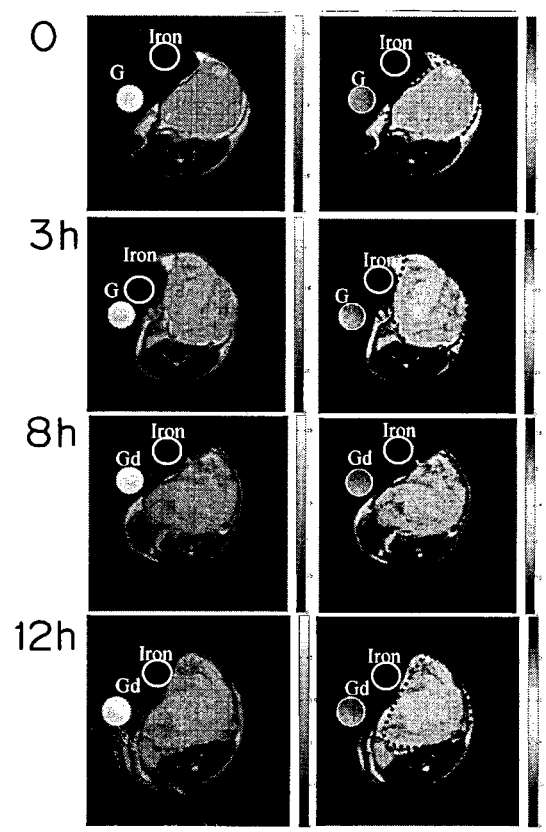
FIGS. 13A and 13B show MR imaging of 22Rv-1 human prostate cancer orthotopic xenografts using peptide-coated iron oxide nanoworms.
Figure 13B:
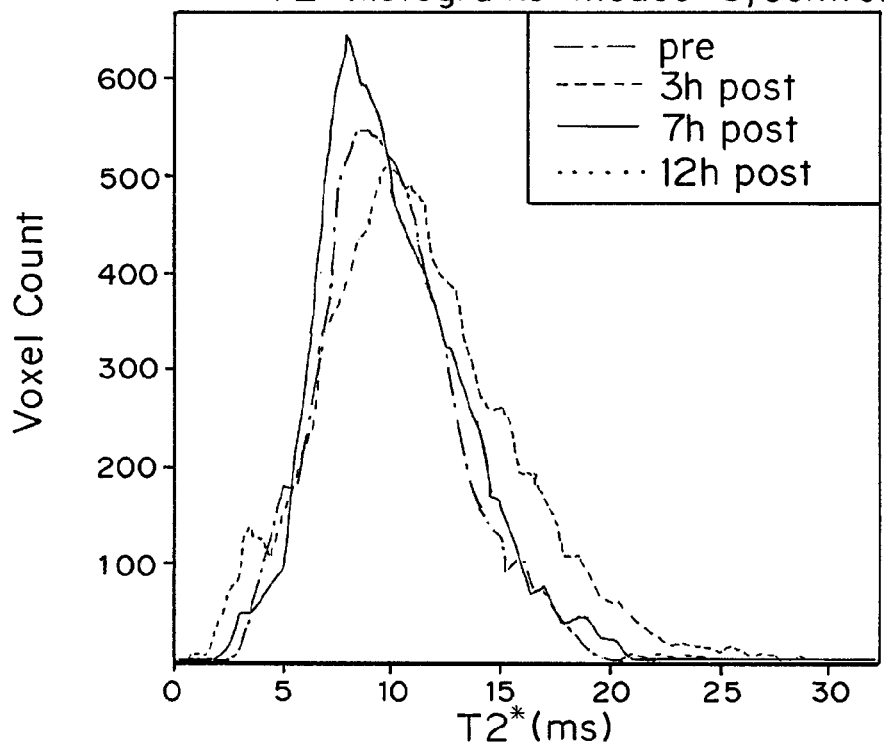
Figure 13B:
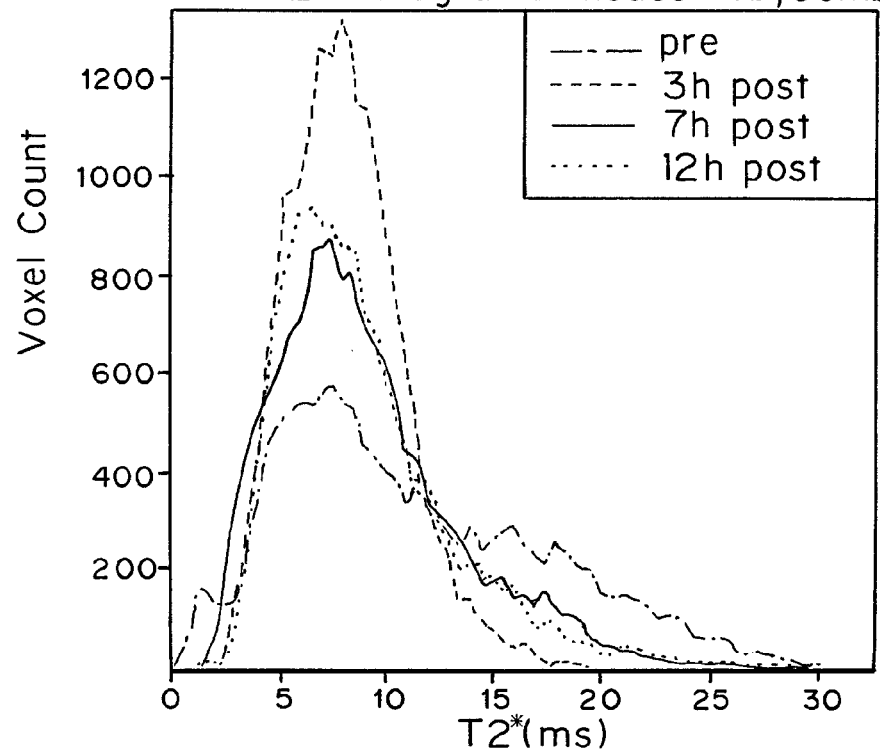

MR imaging of 22Rv-1 human prostate cancer orthotopic xenografts using peptide-coated iron oxide nanoworms shows increased targeting of the cancer xenographs. T2-weighted MR images. A mixture of equal proportions of CRKDKC-coated (SEQ ID NO:5) and CR(NMe)EKA-coated (SEQ ID NO:1) nanoworms (total dose 5 mg/kg) were intravenously injected into tumor-bearing mice. The particles were allowed to circulate for the indicated period of time. Images of axial plains through the tumors are shown. Gadolinium (Gd) and Feridex (Fe) were used as reference standards. The nanoworms highlight the blood vessels in the tumors (see FIG. 13A). Histograms showing the quantitative changes in tumor iron content at different time points. Only the targeted nanoworms show significant accumulation in the tumors with time (see FIG. 13B).

Figure 14A:
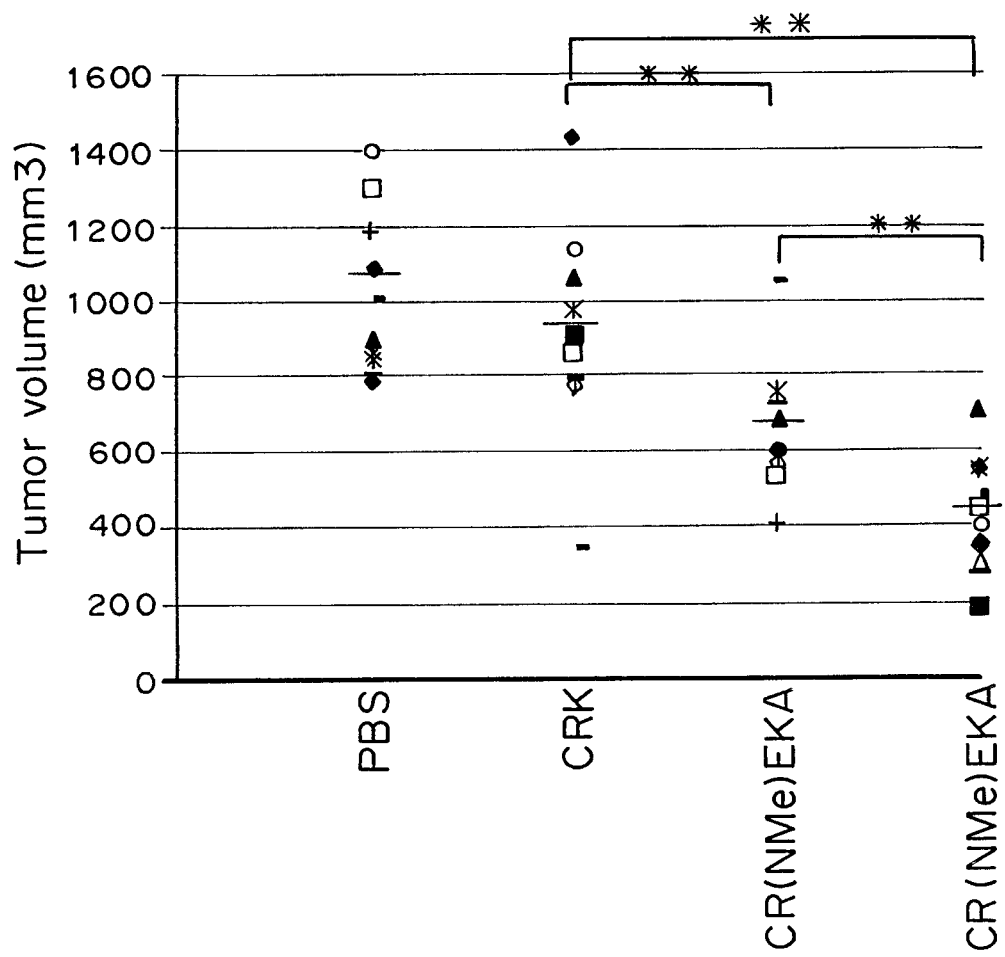
FIGS. 14A and 14B show tumor treatment with targeted nanoworms. Mice bearing 2 week-old orthotopic xenografts of 22Rv-1 human prostate cancer were intravenously injected CRKDKC coated nanoworms, or CR(NMe)EKA-coated, or a combination of both particles in equal amounts. All nanoworms were also coated with 5K polyethylene glycol. The particles were given every other day for 14 days (5 mg/kg/day, total cumulative dose 35 mg/kg).
Figure 14B:
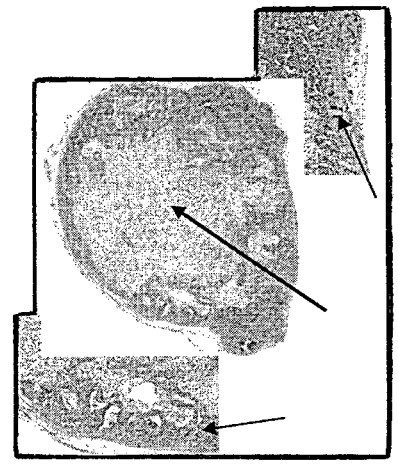
Figure 14B:
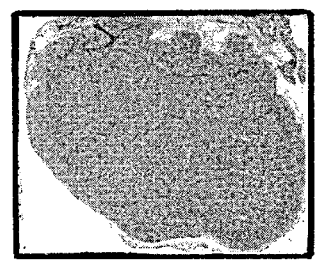

Tumor treatment with targeted nanoworms results in a decrease in tumor volume. Mice bearing 2 week-old orthotopic xenografts of 22Rv-1 human prostate cancer were intravenously injected CRKDKC-coated (SEQ ID NO:5) nanoworms, CR(NMe)EKA-coated (SEQ ID NO:1) nanoworms, or a combination of both particles in equal amounts. All nanoworms were also coated with 5K polyethylene glycol. The particles were given every other day for 14 days (5 mg/kg/day, total cumulative dose 35 mg/kg). Tumor volume one day after the last injection shows a statistically significant decrease in tumor volume with CRKDKC (SEQ ID NO:5) alone, more with methylated CREKA alone, and the most decrease with the combination (see FIG. 14A). Similar results were obtained in two independent experiments. H&E staining showing a large necrotic area in the middle of a treated tumor and blocked blood vessels in the viable tumor rim. Similarly sized tumors in the group that received CRKDKC particles, which home to tumor vessels but do not cause clotting, show no necrosis or blocked blood vessels.

Figure 15A:
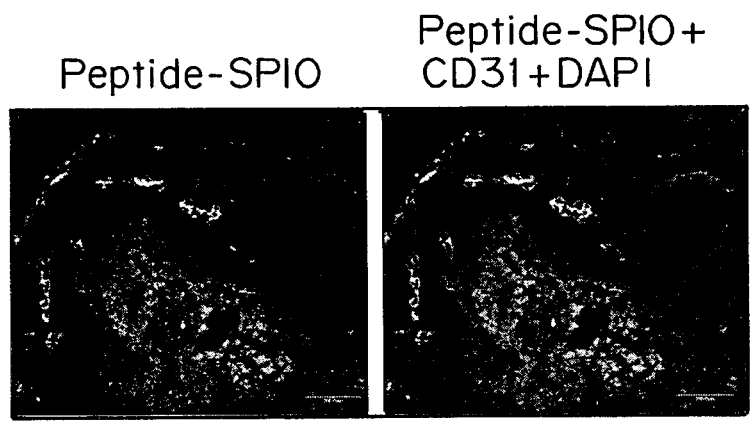
FIGS. 15A-15C show tumor treatment study with 5K-PEG-SPIO coated with CRK, CR(NMe)EKA, or combination (mixture of CRK and CR(NMe)EKA particle).
Figure 15B:
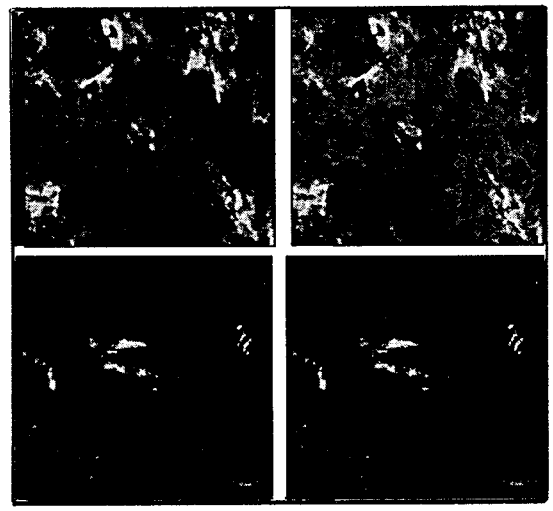
Figure 15C:
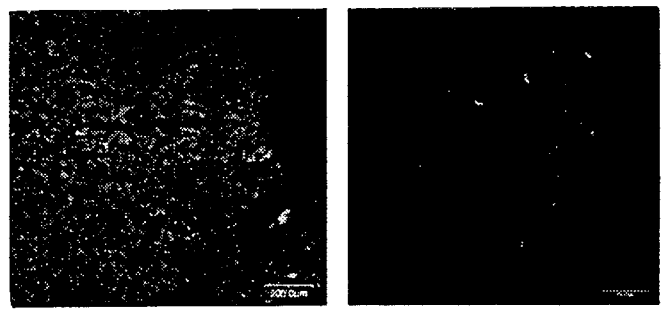
Figure 15C:
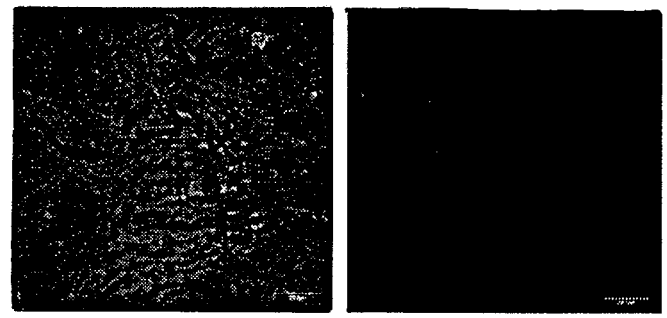

FIGS. 15A-15C A tumor treatment study with 5K-PEG-SPIO coated with CRK, CR(NMe)EKA, or combination (mixture of CRK and CR(NMe)EKA particle) showed no damage or fibrin-filled blood vessels were detected in normal organs of the treated tumor mice in histological examination and fibrin(ogen) staining FIGS. 15A and 15B: Fluorescence images of tumor-homing CRK-mixed with CR(NMe)EKA-conjugated SPIO nanoparticles were made a day after last injection. Tumor sections were stained with anti-CD-31 (FIG. 15A) or anti-fibrino(gen) (FIG. 15B) and examined by confocal microscopy. Nuclei were stained with DAPI, mixture peptides conjugated SPIO, and blood vessels were visualized with CD31 (FIG. 15A) Fibrinogen (FIG. 15B) staining No damage or fibrin-filled blood vessels were detected in normal organs of the treated tumor mice in histological examination and fibrin(ogen) staining.

C. Example 3

Nanoparticle-Induced Vascular Blockade in Human Prostate Cancer

1. Introduction

The prevalence of prostate cancer and the large number of deaths from this disease underscore the need for a paradigm shift in the strategies to develop better treatments for this cancer (Jemal, 2008). Since the 1970's, progress in fundamental cancer biology has led to enormous advances in our understanding of the processes that underlie malignant transformation and metastatic dissemination. Nonetheless, eradication of cancer remains an elusive clinical goal, largely due to the heterogeneous nature of individual cancers and our inability to target therapies to neoplastic cells without damaging normal tissues. Prostate tumors are anatomically, histologically and genetically heterogeneous (Macintosh, 1998; Ruijter, 1996; Miller, 1994), causing variable responses to various therapies. These obstacles are further magnified by limited ability to image cancerous regions and track the progression of treatments (Jain, 2002; Weissleder, 2002).

One approach to overcome the heterogeneity of tumors is to focus on tumor vasculature. Tumor vasculature has proven to be particularly well suited as a site for homing-based (synaphic) targeting. It expresses a multitude of molecules that are not expressed in the vessels of normal tissues, and the vascular wall is readily accessible for blood-borne substances (Ruoslahti, 2010). Most vascular strategies use anti-angiogeneic therapy to prevent formation of new blood vessels in a growing solid tumor; these approaches have been found to be useful, particularly in treating advanced-stage cancers (Folkman, 1995; Ferrara, 1999; Folkman, 2007; Carmeliet, 2000; Beecken, 2001). An alternative strategy is based on occluding the vasculature of a tumor and thereby inducing tumor necrosis. Targeting of truncated tissue factor to tumors has been used for this purpose with some success (Bieker, 2009; Huang, 1997; Kessler, 2005; Nilsson, 2001; Ran, 1998). Nanomedicine is an emerging field that uses nanoparticles to facilitate the diagnosis and treatment of diseases. Nanoparticles can be engineered to perform multiple functions, which provide a potential advantage over simple drugs. In this study we designed nanomedicine-based approaches to more effectively and safely block the tumor circulation.

Previous screens of phage-displayed peptide libraries in vivo and ex vivo discovered specific targets in tumor vessels (Hoffman, 2004). Some of the tumor-homing peptides identified in this manner recognize products of blood clotting on the walls of tumor vessels and in tumor stroma that are not present in normal vessels and tissues. The reasons for this difference are thought to be a pro-coagulant tumor environment and seepage of plasma proteins including fibrinogen from the leaky tumor vessels into the tissue (Abe, 1999;

Dvorak, 1985). Three tumor-homing peptides have been identified that recognize these clotting products in the vessels of a variety of tumor types, including human cancers (Pilch, 2006; Simberg, 2007). Tumors grown in mutant mice null for fibrinogen, or mice lacking plasma fibronectin, which becomes covalently bound to fibrin during blood clotting, are not recognized by these peptides, indicating that the peptides target fibrin-fibronectin complexes.

Recently one of the peptides that recognize fibrin-fibronectin complexes, a pentapeptide with the sequence CREKA, was used to design a self-amplifying nanoparticle delivery system (Simberg, 2007). Iron oxide nanoparticles coated with this peptide accumulate in tumor vessels, where they induce additional local clotting, and thereby produce new binding sites for more particles. This amplification system enhanced homing of the nanoparticles in a mouse tumor model without causing clotting or other obvious side effects elsewhere in the body. The self-amplified tumor accumulation produced enhancement of tumor imaging, but significant inhibition of tumor growth was not obtained. Disclosed herein is an effective theranostic system based on earlier findings using prostate cancer as the target tumor.

2. Methods i. Cell Lines and Tumors

The 22Rv1 prostate cancer cell line was obtained from American Type Culture Collection (Manassas, Va.). The cells were grown in RPMI 1640 media supplemented with 2 mM glutamine, 1% penicillin-streptomycin, and 10% FCS at 37° C. and 5% CO2. Xenografts were created by injecting BALB/c nude mice with $2 \times 10^6$ cells in PBS, orthotopically into the prostate gland. The LAPC9 human prostate adenocarcinoma xenograft was from Dr. Lily Wu (University of California, Los Angeles) and used to produce tumors as described (Agemy, 2008). Animal experimentation was performed according to procedures approved by the Animal Research Committee at the University of California, Santa Barbara, and the Sanford-Burnham Medical Research Institute, San Diego.

ii. Peptide Synthesis

Peptides were synthesized with an automatic microwave assisted peptide synthesizer (Liberty; CEM, Matthews, N.C.) using standard solid-phase Fmoc/t-Bu chemistry. During synthesis, the peptides were labeled with 5(6)-carboxyfluorescein (FAM) with a 6-aminohexanoic acid spacer separating the dye from the sequence. The preparation of the non-proteinogenic amino acids used for the synthesis of the N/Cα-methylated CREKA analogs will be reported elsewhere. The synthesis of CRKDKC with an extra N-terminal cysteine used for the chemoselective ligation used in this work will be described elsewhere.

iii. Computer Modeling

The conformational profiles of the CREKA analogs, which were constructed by replacing each residue (one-by-one) by its N-methyl or Cα-methyl counterpart, were characterized by Molecular Dynamics simulations. Methodology and clustering analyses were as described in (Zanuy, 2009).

iv. Preparation of NW and Ni-Liposomes

NW (Park, 2009), NW coated with peptides and Ni-liposomes were prepared as described (Simberg, 2007). The aminated nanoworms were PEGylated with maleimide-5KPEG-NHS (JenKem Technology). In the experiments in which Ni-liposomes were used, the nanoworms were functionalized for subsequent peptide coupling with N-α-maleimidoacetoxy)succinimide ester (AMAS; Pierce). Peptides were conjugated to the nanoparticles with the Michael addition reaction between the thiol from a cysteine in the peptide sequence and the maleimide on the functionalized particles.

v. In Vivo Peptide Homing

Orthotopic prostate cancers were used when they reached 0.5-1 cm in size. Synthetic peptides labeled with fluorescein (approximately 200 µg) were intravenously injected into tumor-bearing mice and allowed to circulate for 15 minutes to 3 hours. The mice were perfused with PBS through the heart under anesthesia, and tissues were collected and observed under UV light (Illumatool Bright Light System LT-9900, Lightools Research, Encinitas, Calif.), and then processed for immunofluorescence or immunohistochemistry.

vi. In Vivo NW Injections

To analyze NW biodistribution, mice bearing orthotopic 22Rv1 tumors were injected into the tail vein (5 mg of iron per kg body weight). In homing experiments, the mice were euthanized 5-6 hours after the injection by cardiac perfusion with PBS under anesthesia, and organs were dissected and analyzed for particle homing. In tumor treatment experiments, nude mice bearing 2 week-old 22Rv-1 or LAPC9 orthotopic xenografts (typically about 200-250 mm$^3$ in tumor volume) were intravenously injected with NW in 150 µl PBS or PBS as a control. The NW were injected every other day for 14 days. The total cumulative dose was 35 mg iron/kg. At the end of the treatment, the mice were perfused with PBS under anesthesia, and the tumors were harvested. Tumor volume was calculated using the following formula: volume (mm3) $=(d2 \times D)/2$, where d and D are the smallest and largest tumor diameters, respectively.

vii. Peptide Stability

The peptides were conjugated with a linker that bridges the NW and a cysteine residue on the peptide, forming a disulfide with the OPSS group. The peptide-coated NW were injected into animals, and blood was collected 15 minutes and 3 hours after the injection. The plasma was separated and NW were collected by ultracentrifugation (100,000×g for 10 minutes at 4° C.). Proteins bound to the NW were removed by incubation with glycine-HCl, pH 2.8 on a magnetic LS columns (MACS separation columns, Miltenyi Biotec, Bergisch Gladbach, Germany). The peptides were cleaved from the NW by incubating with 10 mM dithiothreitol for 30 minutes at room temperature. The iron oxide was separated from the peptide by ultracentrifugation (100,000×g for 10 minutes at 4° C.) and the supernatant fractions containing the peptide were analyzed by matrix-assisted laser desorption ionization-time of flight (MALDI-TOF) mass spectrometry.

viii. Immunofluorescence and Immunohistochemistry

Tissues from mice injected with nanoparticles were fixed in 4% paraformaldehyde overnight at 4° C., cryo-protected in 30% sucrose overnight and frozen in OCT embedding medium. For histological analysis, 7-µm sections were cut and sections were H&E stained.

For immunostaining, tissue sections were first incubated for 1 hour at room temperature with 10% serum from the species in which the secondary antibody was generated, followed by incubation with the primary antibody overnight at 4° C. The following antibodies were used: rat monoclonal anti-mouse CD31 (10 µg/mL; BD Pharmingen, San Jose, Calif.), mouse fibrin(ogen) antiserum (1:100; Nordic, Tilburg, Netherlands). The primary antibodies were detected with Alexa 647 goat anti-rat, and 647 donkey anti-goat secondary antibodies (1:1000; Molecular Probes, Eugene, Oreg.). Each staining experiment included sections stained with secondary antibodies only as negative controls. Nuclei were counterstained with DAPI (5 µg/mL; Molecular Probes). The sections were mounted in gel/mount mounting medium (Biomeda, Foster City, Calif.) and viewed under a Fluoview 500 confocal microscope (Olympus America, Center Valley, Pa.; 200 micron micrographs, 20× magnification and 50 microns, 40×).

For immunohistochemical staining of frozen tissue sections, endogenous peroxidases were quenched with 3% $H_2O_2$ (DAKO-Cytomation). Sections were blocked for 1 hour in 5% Donkey serum in Dako cytomation Ab dilution solution. Sections were treated with DAKO Biotin/Avidin Blocking system; incubated overnight at 4° C. with mouse fibrin(ogen) antiserum. The primary antibody was detected with biotinylated anti-mouse IgG and Vectastain ABC kit (Vector Laboratories, Burlingame, Calif.). Nuclei were counterstained with hematoxylin (Vector Laboratories Burlingame, Calif.). To quantify the homing area of fibrin(ogen) within tumors the stained section were scanned with the Scanscope CM-1 scanner and analyzed with the ImageScope software41 (Aperio Technologies, Vista, Calif.).

Apoptosis was determined using the TUNEL assay for the identification of double-stranded DNA breaks using the In situ Cell Death Detection Kit (Roche Applied Science, Indianapolis, Ind.), according to the manufacturer's instructions.

ix. Magnetic Resonance Imaging

Nude mice bearing 22Rv-1 orthotopic human prostate cancer xenografts were intravenously injected with superparamagnetic iron oxide NW coated with peptides, or left not coated at a dose of 5 mg of iron per kg body weight. Each animal received Ni-liposomes (0.2 mmol of Ni) intravenously 1 hour prior to the NW to increase the blood half-life of the NW. Approximately 7-8 hours after the NW injection, the mice were anesthetized with isoflurane and subjected to T2-weighted MRI scans with a 3-Tesla MR imager (GE Healthcare Technologies, Milwaukee, Wis.). After imaging, tissues of interest were harvested and processed for immunofluorecence.

x. Contrast-Enhanced Ultrasound (CEUS)

Definity® contrast agent (Lantheus Medical Imaging; 5 µl in 45 µl of saline) were injected into the tail vein of mice using a 28 gauge insulin syringe. Philips iU22 with a L12-5 transducer was used for imaging with a low mechanical index (MI), contrast specific imaging mode (power modulation mode). The imaging parameters were set as follows and kept identical throughout the study: depth 2 cm, focus zone 2 cm, MI 0.06, 5 frames per second. Two-minute cine loop was saved for time intensity curve analysis using Philips QLab. CEUS was performed prior to, 1, 3, and 6 hours after injection of mice with CREKA-NW alone or in combination with CRKDKC-NW. The tumor rim, center, and the surrounding tissue were separately examined to quantify the efficiency of tumor circulation. CEUS analysis of tumors treated for 2 weeks with the NW was carried out using Photoshop with a threshold method, in which the pixels with enhancement and those without were counted (the threshold was set arbitrarily, as there was no fixed number). The percent area with enhancement=the pixel number of the enhanced area/the pixel number of the entire tumor×100.

xi. Statistical Analysis

Data were analyzed by 2-tailed Student unpaired t-test or 1-way analysis of variance followed by a suitable post-hoc test. P values of less than 0.05 were considered statistically significant.

Figure 16A:
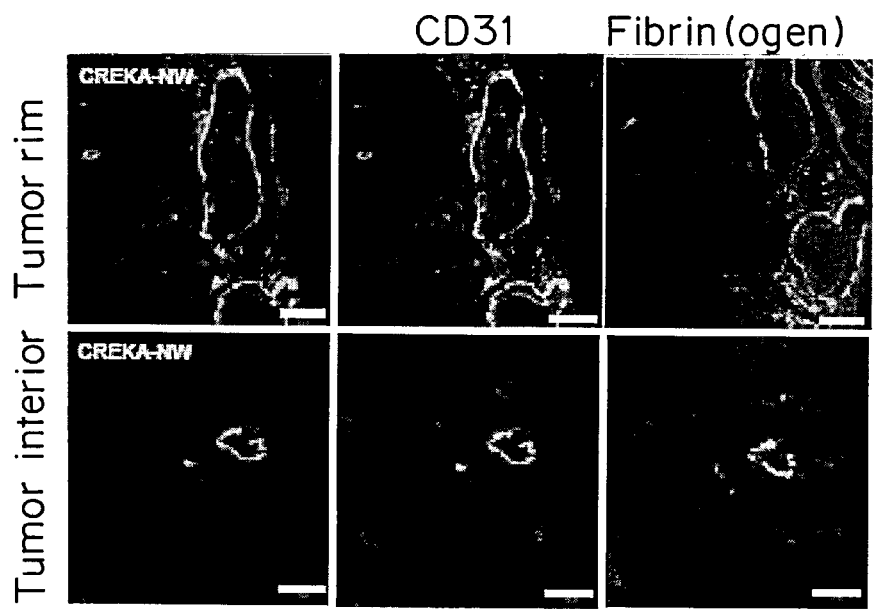
FIGS. 16A, 16B, 16C and 16D show that combining CREKA-NWs with nanoworms coated with another tumor homing peptide enhances homing efficiency. (A) Iron oxide nanoworms coated with FAM-labeled CREKA peptide were injected intravenously (5 mg of iron per kilogram of body weight) into nude mice bearing orthotropic 22Rv1 human prostate tumors. The mice had been preinjected with Ni-liposomes to reduce uptake by the reticuloendothelial system (Simberg D et al. Biomimetic amplification of nanoparticle homing to tumors. *Proc Natl Acad Sci USA*. 2007; 104(3): 932-936). Tumors were harvested 5 hours later, and tumor sections were stained with antibodies and examined by confocal microscopy (the 5-hour time point was found to be optimal for nanoworm homing with regard to accumulation of the nanoworms in the tumor and clearance of nanoworms from the blood). The CREKA-coated particles are shown with bright staining; blood vessels and clotting were visualized separately with anti-CD31 (example shown with arrowhead) or antifibrin(ogen) staining (example shown with arrow); nuclei were stained with DAPI (dark staining) Bars represent 200 μm. (B) Nanoworms coated with FAM-labeled CRKDKC or CGKRK were injected intravenously, and the tissues were collected and processed as in A. CRKDKC- or CGKRK-coated particles are shown in light gray; blood vessels visualized with anti-CD31 are magenta (white indicates colocalization of CD31 and coated particles) and those visualized with anti-fibrin(ogen) staining are dark gray (asterisks indicates colocalization of fibrin(ogen) and coated particles); nuclei were stained with DAPI (dark stained circles). Large vessels were selected for the panels on the right because intravascular clotting (which is not promoted by CRKDKC-NWs or CGKRK-NWs) is most apparent in larger vessels. Bars represent 200 μm (left and middle panels) and 100 μm (right panels). (C) A mixture of nanoworms coated with rhodamine-labeled CREKA (light gray staining in first panel) and FAM-labeled CRKDKC (light gray staining in second panel) was injected intravenously (2.5 mg of iron per kilogram of each nanoworm preparation), and the tissues were collected and processed as in A and stained for fibrin(ogen) (light gray in third panel); nuclei were stained with DAPI (dark stained circles). Bars represent 200 μm. (D) Mice were injected with the indicated materials as in panels A, B, or C. The sections stained with anti-fibrin(ogen) antibody were subjected to image analysis with Scanscope to quantify fibrin (ogen)-positive areas. The insets show examples of anti-fibrin (ogen) immunostaining in the tumor rim (left) and interior (right) from mice injected with the nanoworm mixture. Bars represent 50 μm. Statistical analyses were performed with analysis of variance. Error bars represent SEM (n=5-6); **P<0.01
Figure 16B:
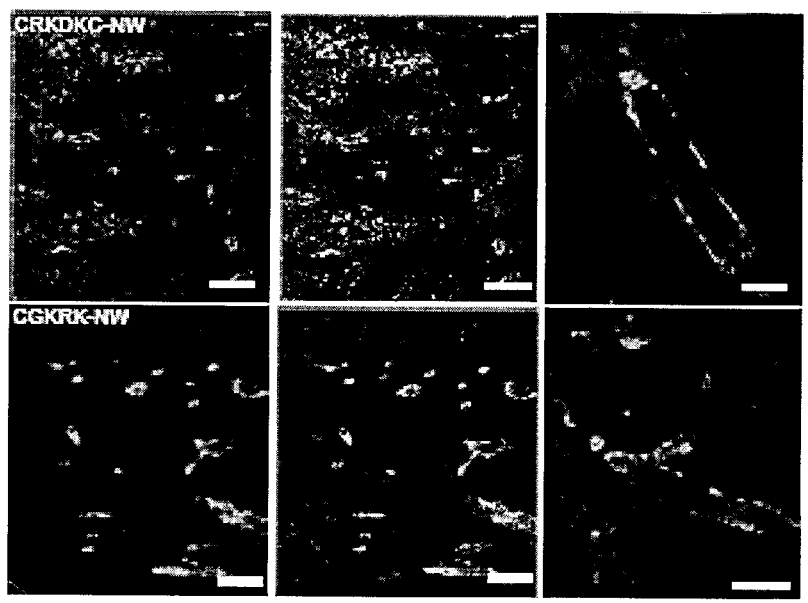

3. Results i. Nanoworm Combinations for Enhancing the Activity of CREKA Nanoparticles Elongated iron oxide nanoparticles, "nanoworms" (NW), which are more effective in peptide-mediated cell binding than spherical particles were used (Park, 2009). Nanoworms (NW) coated with the CREKA peptide accumulated in the vessels of orthotopic 22Rv1 human prostate cancer xenograft tumors and caused clotting in them, as evidenced by the presence of fibrin(ogen)-containing deposits in the vessel lumens (FIG. 16a). In tumors of untreated mice or mice treated with nanoparticles coated with peptides other than CREKA, mainly the blood vessel walls were positive for fibrin(ogen) (FIG. 16b). Most of the increased fibrin(ogen) staining in the CREKA-NW-treated 22Rv1 tumors was in the tumor periphery, whereas little NW accumulation or clotting was seen in the center of the tumors.

It was possible to improve the tumor delivery of NW by combining CREKA with a tumor-homing peptide that recognizes a different target molecule other than CREKA, and therefore can bind to different vessels in the tumor. Two tumor-homing peptides were tested for their ability to increase CREKA-NW homing: CRKDKC, which was originally identified as a wound-homing peptide (Jarvinen, 2007), and CGKRK (Hoffman, 2003). Both peptides bind to the blood vessels in various kinds of tumors (Jarvinen, 2007; Hoffman, 2003). Both CRKDKC-NW and CGKRK-NW accumulated in more than 70% of the 22Rv1 tumor vessels as evidenced by colocalization with CD31 staining (FIG. 16b; data not shown).

Figure 16C:
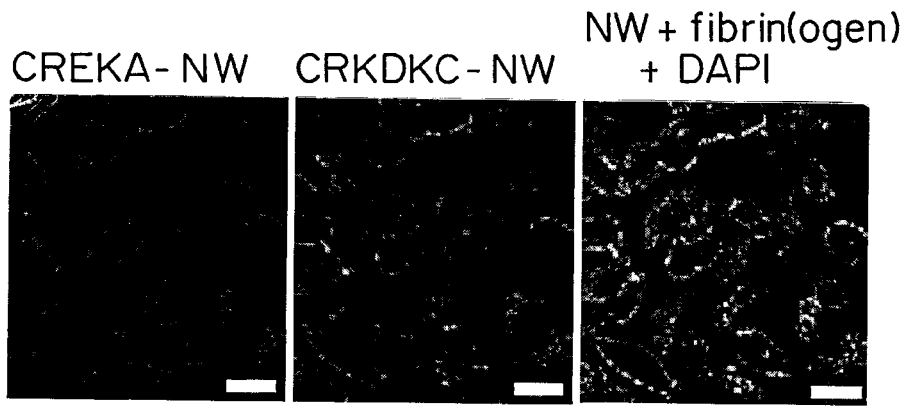
Figure 16D:
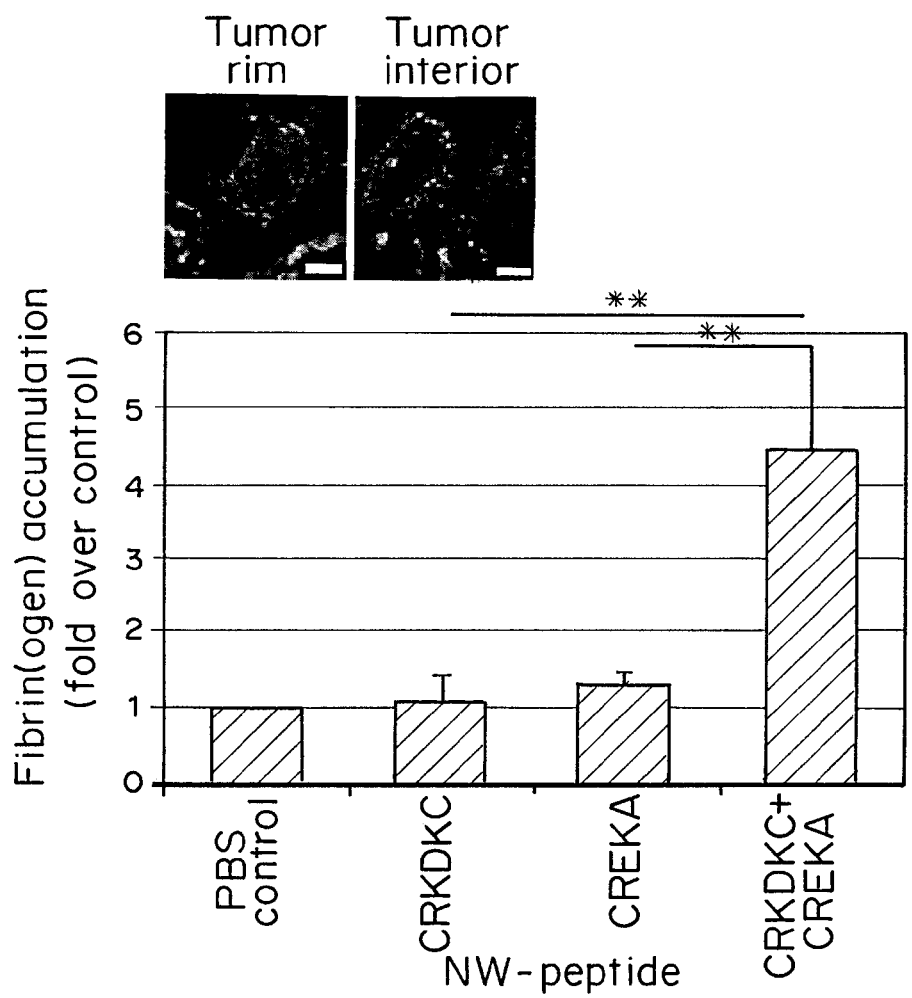
Figure 17A:
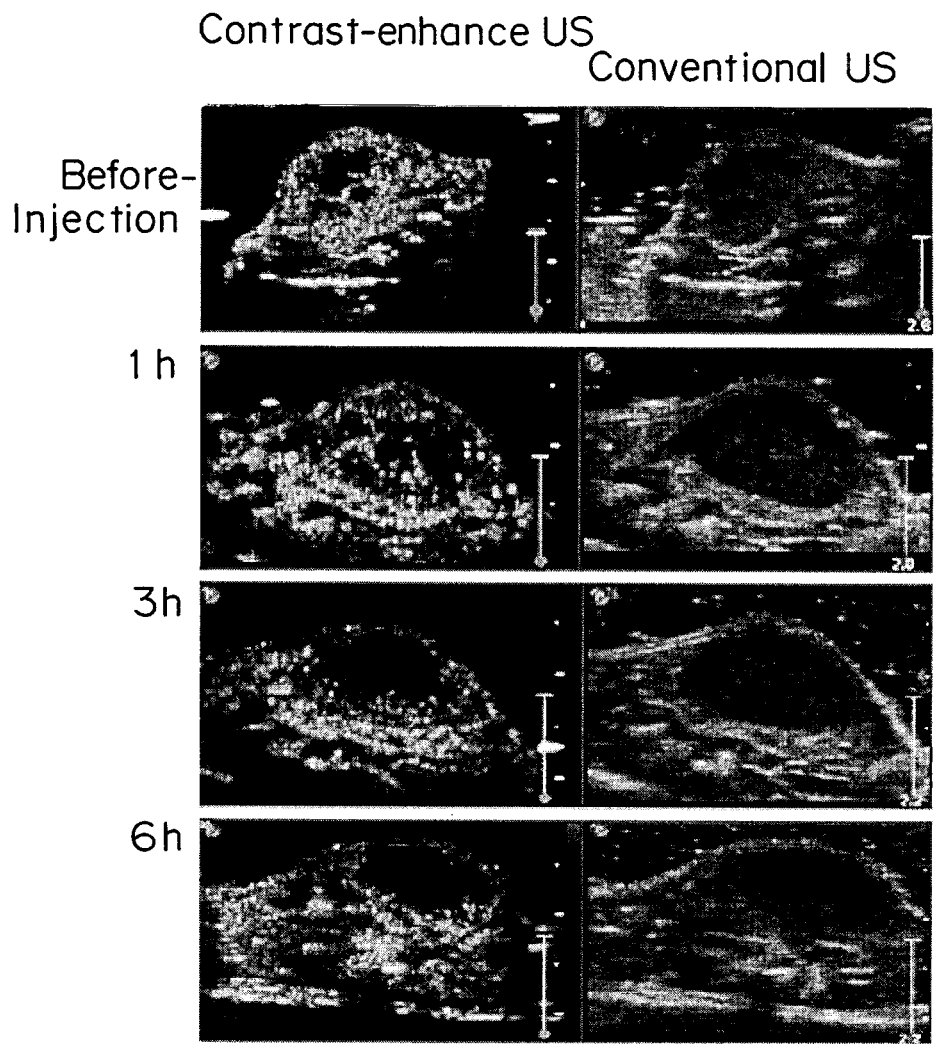

Next NW double-coated with CREKA and one of the other peptides were tested. However, the double-coated NW showed only minimal tumor homing (data not shown). Coating the nanoparticles with two different peptides on the same nanoparticle can reduce the surface density of each peptide to an extent that adversely affects the homing. Surprisingly, mixtures of CREKA-NW with CRKDKC-NW or CGKRK-NW, which were used as controls, were quite effective in delivering CREKA-NW to vessels in the tumor interior and causing clotting in them. The mixed single-peptide particles can aggregate in tumor vessels, making it possible for each peptide to carry both types of particles to the target. Among the particle mixtures, the CREKA-CRKDKC mixture was particularly effective in homing to the entire tumor (FIG. 16c), and subsequently this combination was focused on. Quantification of fibrin(ogen) accumulation showed that combining CREKA-NW with CRKDKC-NW enhanced clotting by 4-5 fold compared to CREKA-NW alone (FIG. 16d). Contrast-Enhanced Ultrasound (CEUS) Imaging showed a 90% reduction in blood flow at 6 hours after the injection of the NW mixture (FIG. 17).

ii. Enhancing the Activity of CREKA by Incorporation of Non-Coded Amino Acids

Figure 18A:
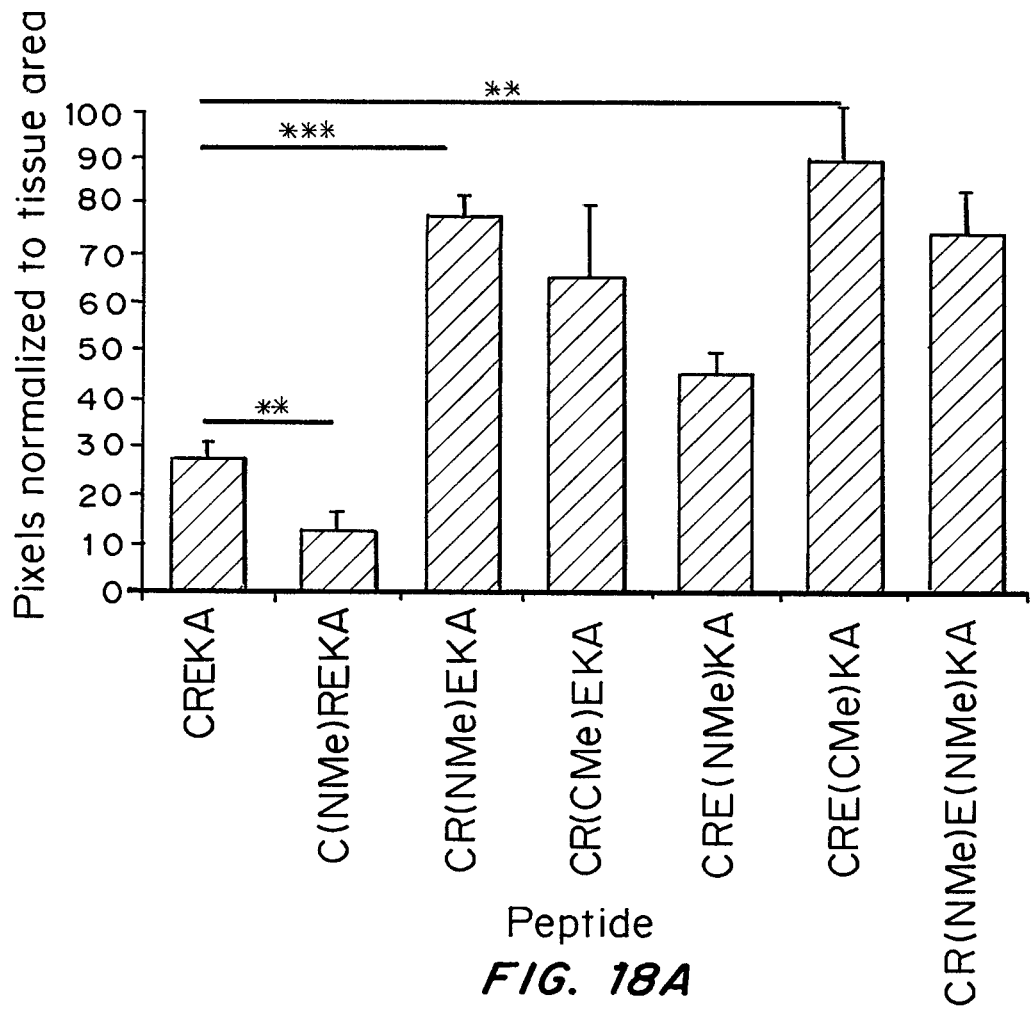
FIGS. 18A, 18B, 18C and 18D show tumor accumulation of the CREKA peptide and its N/Cα-methylated variants. Mice bearing orthotropic 22Rv1 xenograft tumors were injected intravenously with 200 μg of FAM-labeled CREKA or N/Cα-methylated CREKA peptides, which were allowed to circulate for 3 hours. This time point highlights the differences between nonmodified CREKA and some of the methylated variants (D). The mice were perfused through the heart with PBS, and the organs shown were collected and viewed under ultraviolet light. (A) Quantification of fluorescence with ImageJ software. Several N/Cα-methylated CREKA analogs produced stronger fluorescence than unmodified CREKA. Statistical analyses were performed with analysis of variance. Error bars show SEM (n=3-4); P<0.01; *P<0.001. (B-C) Representative images from mice injected with the CREKA or CR(NMe)EKA peptides (B, 22Rv1 xenografts; C, LAPC9 xenografts). In the top panels, white dotted lines show where the organs were placed in a macroscopic examination, and the yellow lines outline the tumor. The bottom panels show confocal images of tumor sections from mice injected with the peptides (light gray staining) indicated above. Blood vessels were visualized with anti-CD31 (shown with asterisks); nuclei were stained with DAPI (dark stained circles). Bars represent 200 μm. (B right panels) Representative confocal image fields illustrate the localization of the CR(NMe)EKA peptide (bright staining) in relation to anti-fibrin(ogen) (dark gray staining) and anti-fibronectin (dark gray staining) staining used as markers of tumor stroma; nuclei were stained with DAPI (blue). Bar represents 50 μm. (C right panels) Quantification of fluorescence with ImageJ software. Statistical analysis was performed with Student t test. Error bars show SEM (n=3); P<0.01. (D) Quantification of fluorescence with ImageJ software 15 minutes or 3 hours after peptide injection into 22Rv1 tumor-bearing mice. CR(NMe)EKA produced stronger fluorescence over time than unmodified CREKA. Statistical analysis was performed with Student t test. Error bars show SEM (n=3-4); *P<0.001. (NMe) and (CMe) indicate an N- or Cα-methylated residue, respectively.
Figure 18B:
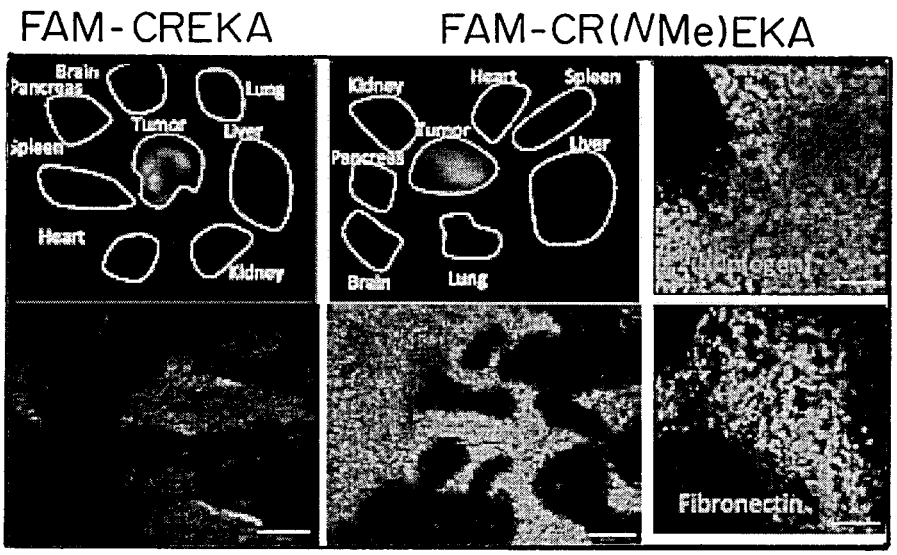
Figure 18C:
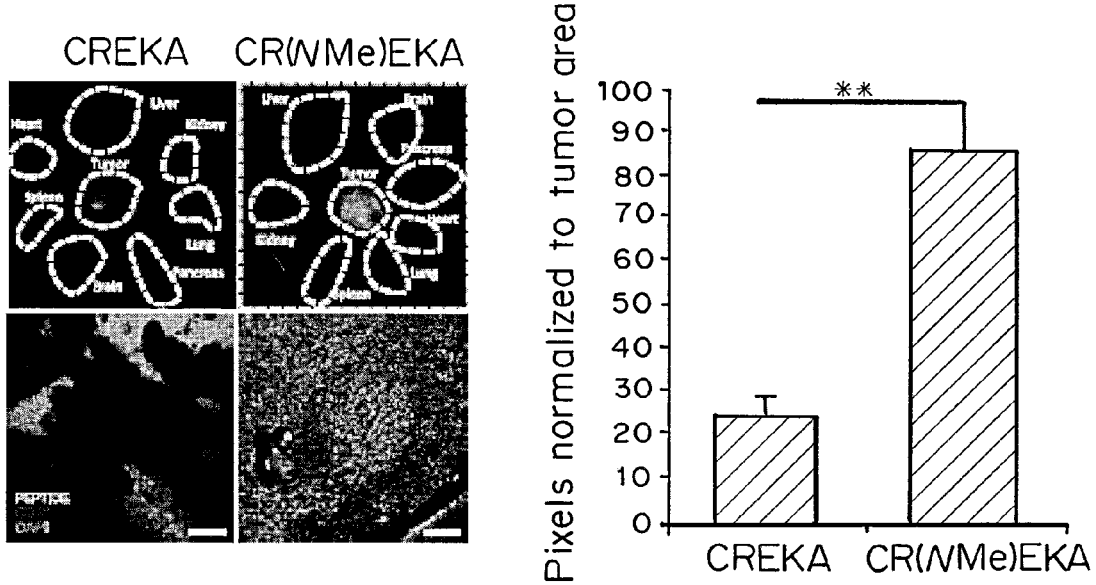
Figure 19:
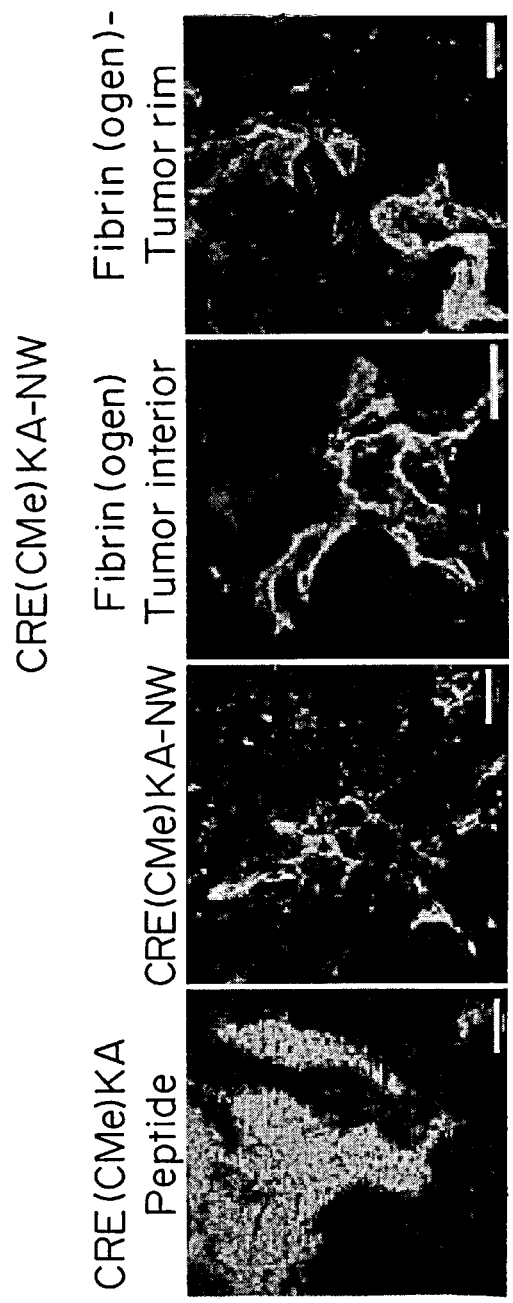
FIG. 19 shows CRE(CMe)KA-NW homing to 22Rv1 tumors. Mice bearing orthotropic 22Rv1 xenograft tumors were injected intravenously with 200 μg of FAM-labeled CRE(CMe)KA or 5 mg of iron per kilogram of nanoworms coated with FAM-CRE(CMe)KA. The peptide was allowed to circulate for 3 hours, and nanoworms were allowed to circulate for 5 hours. The mice were then perfused through the heart with PBS, and the tumors were collected. Tumor sections were stained with CD31 or anti-fibrin(ogen) (light gray staining) and examined by confocal microscopy. Nanoworms are brightly stained; nuclei were stained with DAPI (dark stained circles). Bars represent 200 μm. n=3.

Protecting CREKA against proteolytic degradation can further increase the efficacy of the tumor homing. Proteolysis protection can be achieved through the incorporation of non-proteinogenic amino acids, provided that the bioactive conformation of the peptide is retained (Chatterjee, 2008; Zanuy, 2009). Based on molecular modeling studies (Zanuy, 2009), several N- and Cα-methylated amino acids were selected to replace the key residues in CREKA. This chemical modification can be viewed as the methylation in certain positions of the peptide backbone (at either N or Cα). The CREKA analogs incorporating the N/Cα-methylated amino acids were synthesized as fluorescein (FAM)-labeled peptides. Several of the CREKA analogs showed significantly higher accumulation in the tumors than unmodified CREKA (FIG. 18a). An exception was C(NMe)REKA, in which the arginine residue is N-methylated. This peptide gave only weak tumor fluorescence. Confocal microscopy confirmed the organ-level analyses (shown for CR(NMe)EKA in 22Rv1 tumors in FIG. 18b and for LAPC9 tumors in FIG. 18c). The active CREKA analogs displayed a meshwork pattern within the tumor stroma that was stronger and more extensive than that seen with CREKA. As expected, staining of tumor sections with antibodies against fibrin(ogen) and fibronectin showed that the CREKA analogs accumulated in areas rich in deposition of these proteins (FIG. 18b, panels on the right). CR(NMe) EKA and CRE(CaMe)KA appeared to be equally active in this regard (FIG. 19).

Figure 18D:
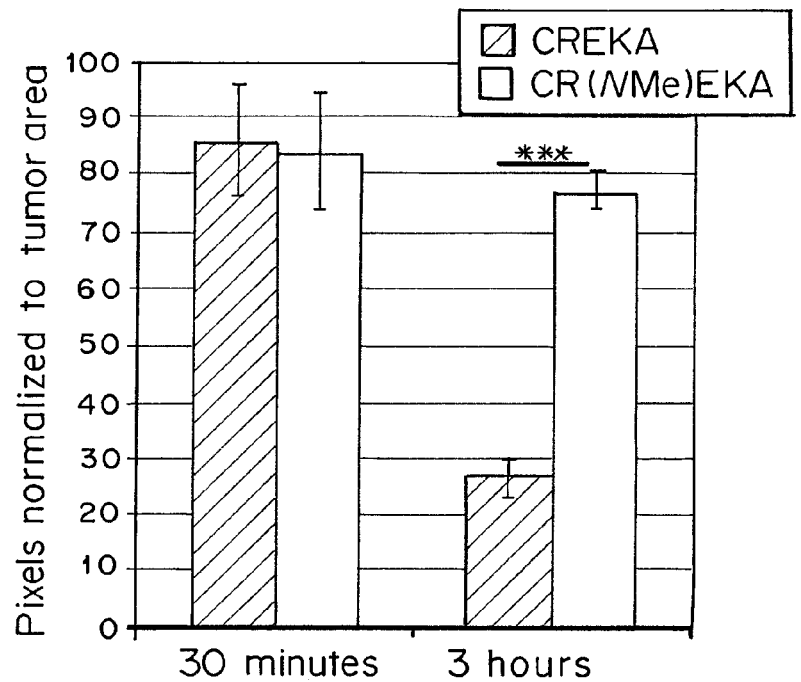

To investigate the stability of CREKA and CR(NMe)EKA in the tumor in vivo, these peptides were intravenously injected into mice bearing 22Rv1 tumors. The peptides gave equally strong fluorescence in the tumors 30 minutes after the injection (FIG. 18d).

Figure 20A:
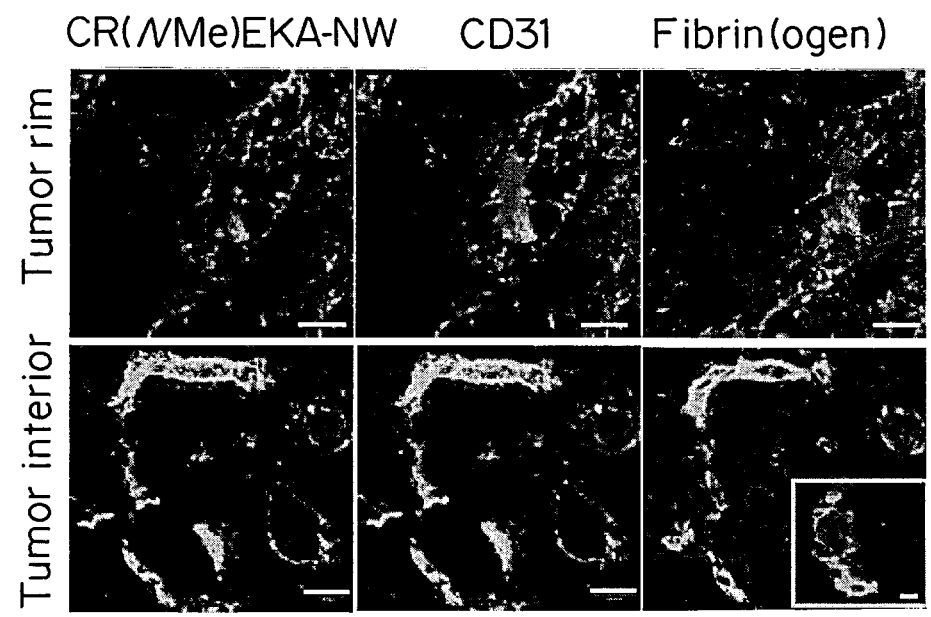
FIGS. 20A and 20B show improved tumor homing of nanoworms coated with an N-methylated CREKA peptide analog. Nanoworms coated with FAM-labeled CREKA peptide or its N-methylated variant, CR(NMe)EKA, were injected intravenously into mice bearing 22Rv1 tumors (total dose 5 mg of iron per 1 kg). (A) Tumors were harvested 5 hours later, and tumor sections were stained with antibodies and examined by confocal microscopy. CR(NMe)EKA-NWs are brightly stained; blood vessels and clotting were visualized separately with anti-CD31 or anti-fibrin(ogen) staining (dark gray staining). Nuclei were stained with DAPI (dark stained circles). Bars represent 100 μm (50 μm in the inset). (B) T2-weighted magnetic resonance images (fast spin echo, repetition time=6.4 seconds, echo time=69 ms). CREKA-NWs or CR(NMe)EKA-NWs were injected intravenously into tumor-bearing mice. The particles were allowed to circulate for 7-8 hours (the time determined in preliminary experiments to be optimal for differential homing). Grayscale images of axial planes through the tumors are shown. Gadolinium (Gd) and Feridex (iron) were used as reference standards. n=3-4.

However, after 3 hours the CREKA fluorescence had decreased by 70%, whereas CR(NMe)EKA showed no significant decrease, suggesting greater stability. Based on these observations, we selected the backbone-methylated peptides CR(NMe)EKA and CRE(CαMe)KA for studies with nanoparticles.

iii. Intratumoral Distribution of Iron Oxide Nanoworms Coated with CREKA Analogs Intravenously injected CRE(CαMe)KA-NW and CR(NMe)EKA-NW showed greatly enhanced accumulation in the blood vessels of the tumor rim and interior (FIG. 19 and FIG. 20a). These areas were also positive for anti-fibrin (ogen) staining This distribution of the NW coated with the N/Cα-methylated peptides within tumors was markedly different from CREKA-NW, in which the nanoparticles appear less abundant in the interior of tumors, (compare FIGS. 19 and 20a with FIG. 16a). No fluorescence from the various NW formulations was observed in normal tissues of the tumor-bearing mice, with the exception of the liver and the spleen, which non-selectively take up all nanoparticles. The liver accumulation of these NW was similar. Significantly more tumor accumulation of CR(NMe)EKA-NW than CREKA-NW was also observed in a different prostate cancer xenograft model, LAPC9.

Figure 20B:
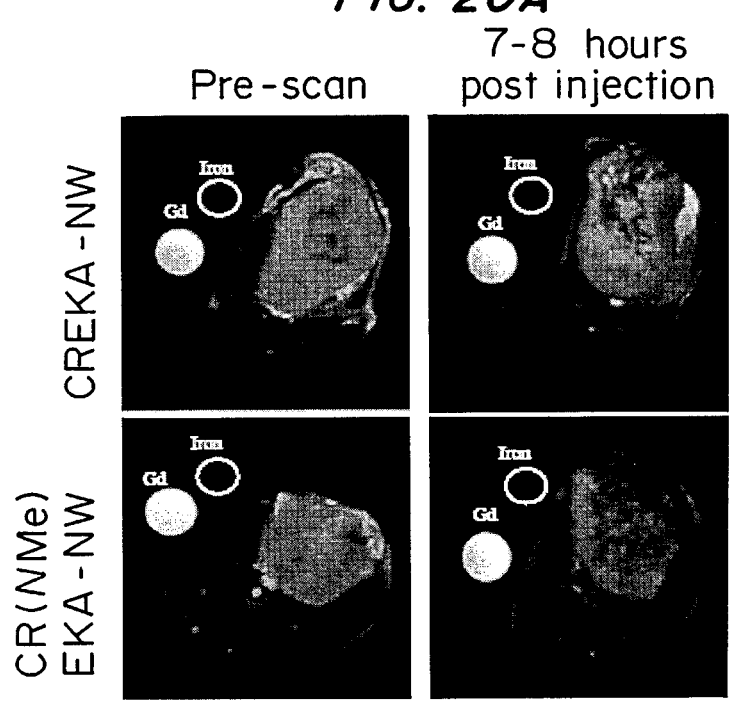

Magnetic resonance imaging of 22Rv1 tumor mice after intravenous injection of NW showed hypointense vascular signals throughout the tumor for the CR(NMe)EKA-NR, and similar, but weaker signals with CREKA-NW (FIG. 20b). Non-targeted nanoworms gave no detectable signal in these tumors after most of the nanoparticles had been cleared from the blood (Sugahara, 2009).

iv. Therapeutic Efficacy of Tumor Blood Vessel Blockage by Peptide-Coated NW

Having optimized the CREKA self-amplified targeting system, by combining CREKA-NW with CRKDKC-NW and by incorporation of N/Cα-methylated amino acids, the tumor treatment potential of the enhanced system was tested. The Ni-liposome pre-treatment used in the short-term experiments to block liver uptake of NW was not suitable for the long-term treatment experiments; it would have doubled the number of injections needed, and some deaths among mice that received multiple injections of Ni-liposomes were observed. The liposome pre-treatment was omitted and instead the NW were coated with polyethylene glycol (PEG) and coupled the homing peptide to the nanoparticles through the PEG chains.

The peptides bound to the NW through PEG were used to directly compare the in vivo stability of CREKA and of CR(NMe)EKA. The peptides were coupled through a reversible disulfide linkage to the PEG coating, and the coated NW were intravenously injected into mice bearing 22Rv1 tumors. The NW were recovered from the blood, and the peptides were isolated and analyzed by mass spectrometry. CREKA and CR(NMe)EKA were equally abundant in the blood samples obtained after 15 minutes of circulation. However, after 3 hours, CREKA was undetectable, indicating that all the peptide was degraded, whereas the amount of CR(NMe) EKA only declined by about 60%. These results show that, as intended by the chemical modification, CR(NMe)EKA is more stable in vivo than CREKA. CR(NMe)EKA bound to plasma clots with somewhat higher affinity than CREKA ($K_d$=2.5 μM and 6.0 μM, respectively; data not shown), which indicates that affinity may also contribute to the superior homing properties of the methylated peptide.

Figure 21A:
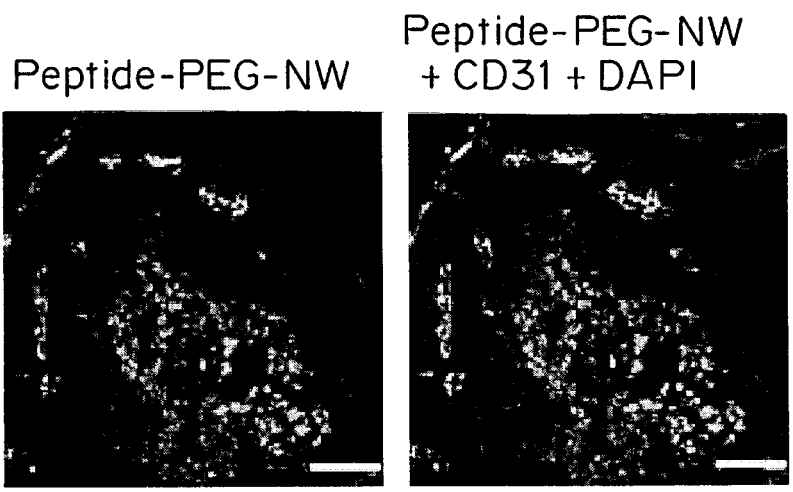
FIGS. 21A, 21B, 21C and 21D show nanoworm distribution and effects on intravascular clotting, tumor apoptosis, and tumor therapy. Mice bearing 2-week-old orthotopic xenografts of 22Rv1 human prostate cancer were injected intravenously with nanoworms coated with peptides through a 5-kDa PEG spacer. The nanoworms were administered every other day for 14 days (5 mg of iron per kilogram per day, total cumulative dose 35 mg/kg). (A) Tumor sections were stained with anti-CD31 (light gray staining); CR(NMe)EKA-NW/CRKDKC-NW combination is shown as bright staining; nuclei were stained with DAPI (dark stained circles). Bars represent 200 μm. The necrotic area at the center of the tumor is autofluorescent. (B) CEUS imaging and analysis showed reduction in tumor blood flow at the end of treatment. The images are representative of n=3. (C) Staining with hematoxylin and eosin showed a large necrotic area (arrow) in the middle of a typical tumor treated with the CR(NMe)EKA-NW/CRKDKC-NW combination and occluded vessels in the viable rim of these tumors (broken arrows). A tumor of a similar size from a mouse treated with CRKDKC-NWs alone is shown for comparison. (D) Apoptosis analysis by TUNEL staining is shown as light gray staining; nanoworm combination is shown as brightly stained spots; nuclei were stained with DAPI. Bars represent 200 μm.
Figure 21B:
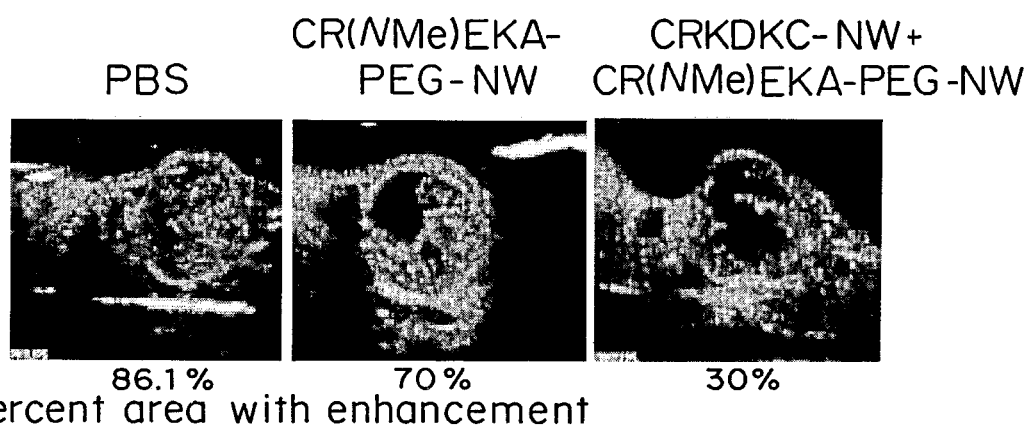

There was some loss of homing activity and clotting in tumor vessels compared to the PEG-free nanoparticles. Multiple injections can make up for this reduced activity. Indeed, many of the blood vessels in the tumors of the mice treated for 2 weeks with the NW combination were filled with peptide particles and deposits positive for a fibrin(ogen) immunostaining (FIG. 21A, data not shown). Moreover, CEUS (Contrast-Enhanced Ultrasound) analysis of tumors treated with the NW revealed a reduction in tumor blood flow; CR(NMe)EKA-PEG-NW alone gave a 30% reduction, and combining CR(NMe)EKA-PEG-NW with CRKDKC-PEG-NW more than doubled the effect (FIG. 21B).

Figure 21C:
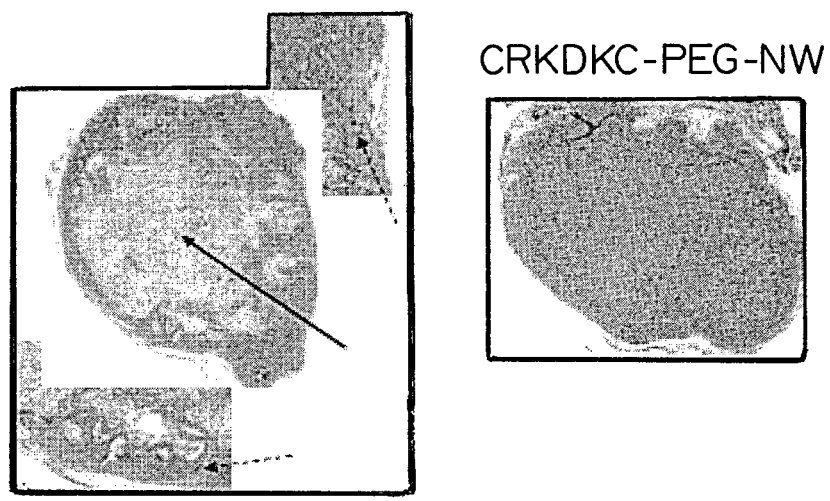
Figure 21D:
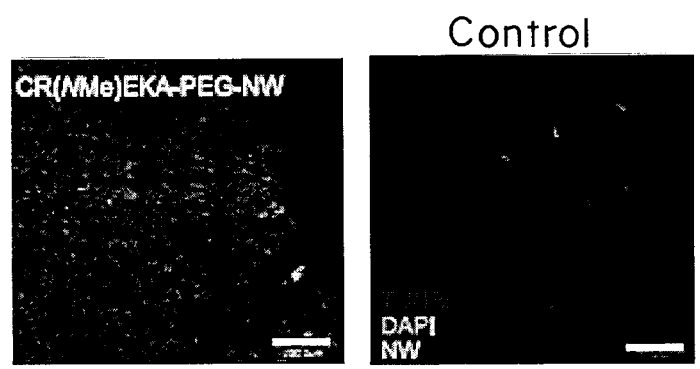
Figure 21D:
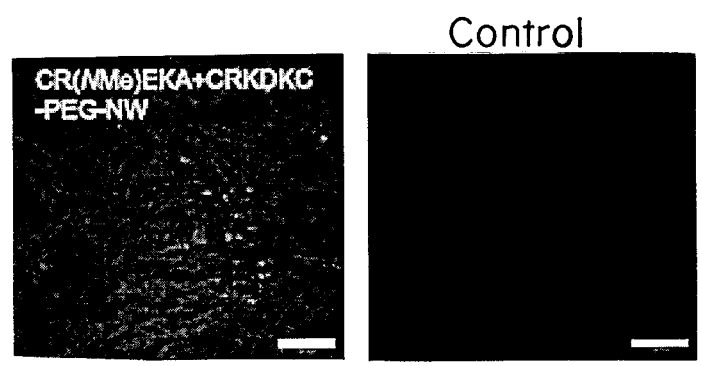
Figure 22A:
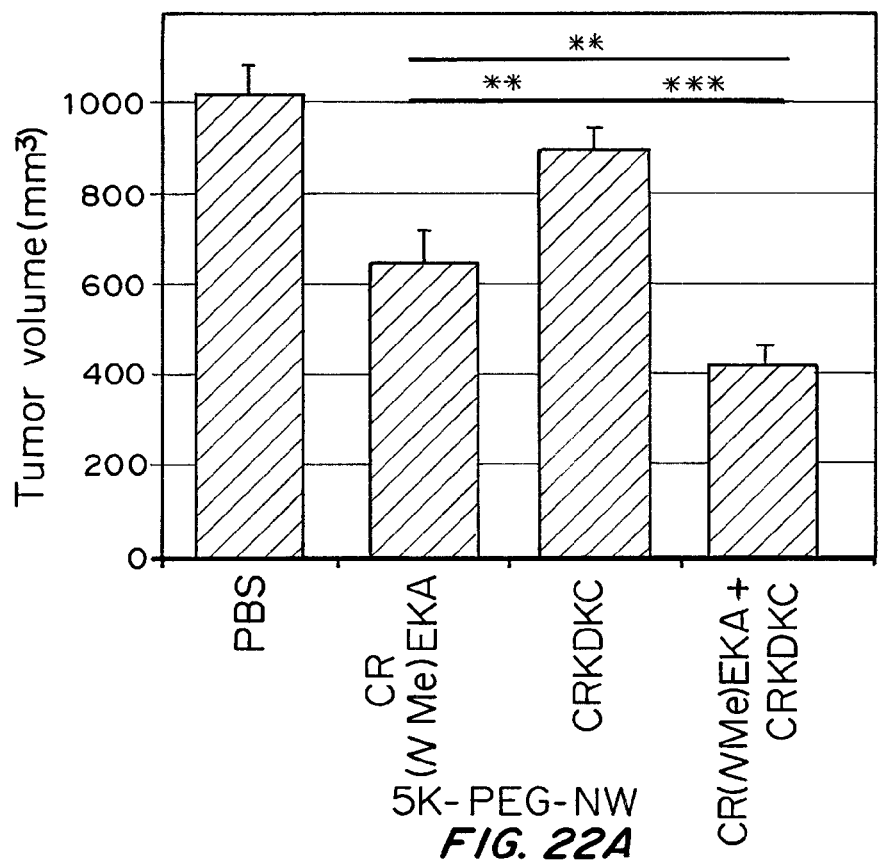
FIGS. 22A and 22B show tumor treatment with targeted nanoworms. Mice bearing orthotopic xenografts of 22Rv1 or LAPC9 human prostate cancer (2 weeks or 10 days after inoculation, respectively) were injected intravenously with nanoworms coated with peptides through a 5-kDa PEG spacer. The particles were administered every other day for 14 days (5 mg of iron per kilogram per day, total cumulative dose 35 mg/kg). (A) Tumor volume 1 day after the last injection in the 22Rv1 model is shown. Statistical analyses were performed with analysis of variance. Error bars show SEM (n=10-12); P<0.01; *P<0.001. Similar results were obtained in 2 independent experiments. (B) Mice bearing LAPC9 tumors were treated as described in panel A, and survival was monitored over time (n=8 per group). The arrow indicates the day the nanoworm treatment was stopped.
Figure 22B:
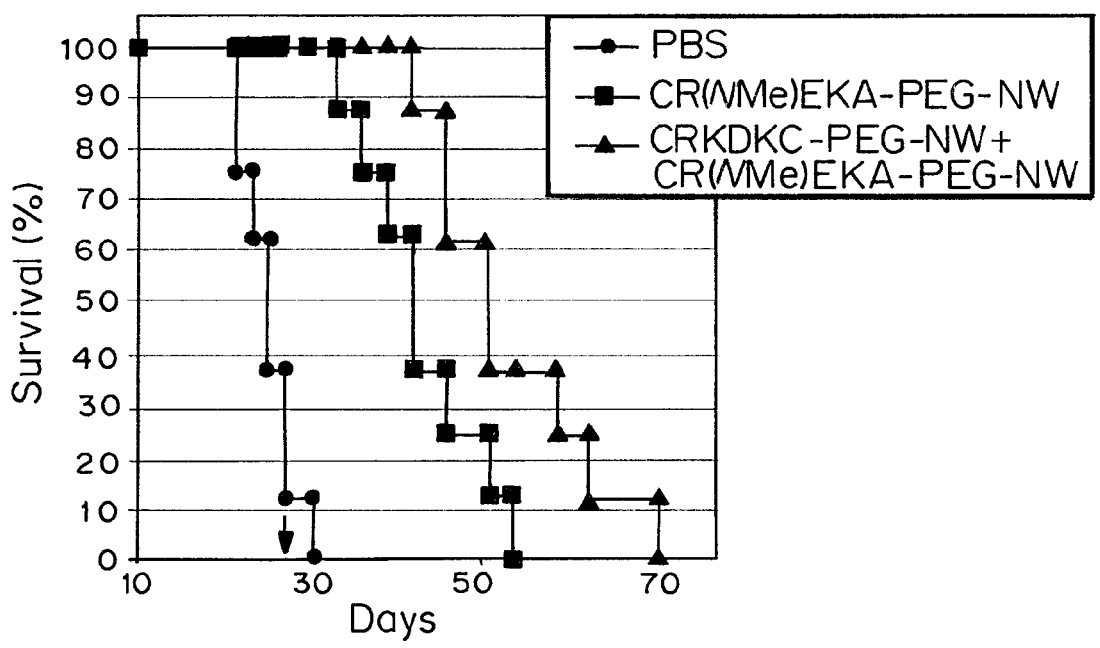

Histological analysis of tumors from mice treated with CR(NMe)EKA-PEG-NW in combination with CRKDKC-PEG-NW showed extensive necrosis as evidenced by a typical loss of nuclei in the center of the tumors (FIG. 21c). No signs of apoptosis or necrosis were observed in similarly sized tumors in the control groups (CRKDKC-PEG-NW and PBS). TUNEL staining revealed extensive apoptosis in the surviving areas of the tumors treated with CR(NMe)EKA-PEG-NW and CRKDKC-PEG-NW combination (FIG. 21d). There was highly significant inhibition of tumor growth in the mice treated with the combination compared with mice that received PBS or CRKDKC-PEG-NW alone (FIG. 22a). CR(NMe)EKA-PEG-NW alone showed a modest but significant inhibition of tumor growth. Neither treatment showed any obvious systemic toxicity as evidenced by body weight measurements and histological analysis of organs from the treated mice. No signs of blood clotting elsewhere in the body (e.g. sudden death or paralysis due to stroke, pulmonary embolism, deep vein thrombosis) or signs of DIC (disseminated intravascular coagulation) were observed. The CR(NMe)EKA-PEG-NW and CRKDKC-PEG-NW combination treatment also inhibited tumor growth in LAPC9 tumor mice, producing a significant survival increase compared to mice treated with vehicle alone (FIG. 22b). These treatments showed no obvious systemic toxicity, as evidenced by body weight measurements and histological analysis of organs from the treated mice. No signs of blood clotting elsewhere in the body (e.g., sudden death or paralysis due to stroke, pulmonary embolism, or deep vein thrombosis) or signs of disseminated intravascular coagulation were observed.

v. Discussion

These results establish a tumor treatment and imaging strategy that is based on synergistic and self-amplifying accumulation of homing peptide-coated iron oxide NW in prostate tumor blood vessels. As shown herein, extensive coverage of tumor vessels can be achieved by combining nanoparticles that were coated with either of two tumor-homing peptides, CREKA or CRKDKC. Also shown is that protecting the CREKA peptide against proteolysis through the incorporation of N/Cα-methylated residues increases the ability of the CREKA-NW to home to tumor blood vessels and to cause clotting in them. Combining the two approaches allowed effective MRI imaging of the tumors and produced extensive inhibition of tumor growth.

The changes introduced into the CREKA self-amplifying tumor vessel homing system (Simberg, 2007) revealed surprising cooperation of two nanoparticle species coated with different peptides. It was assumed that to achieve greater coverage of prostate cancer vessels, the two peptides should be on the same particle, but the disclosure herein shows that having them on separate particles was more effective. Co-accumulation with CREKA-NW was not limited to the CRKDKC peptide; NW coated with another tumor-homing peptide, CGKRK, also enhanced the accumulation of CREKA-NW in tumor vessels, albeit not as strongly as CRKDKC-NW. A likely explanation for this phenomenon is co-aggregation of the two species of nanoparticles, which apparently only happens at the high concentrations of NW achieved within tumor vessels. The clotting induced by the CREKA-NW can contribute to the co-accumulation by trapping loosely bound CRKDKC-NW that would otherwise be washed away by the blood flow. Another cooperative two-particle nanosystem has been described recently (Park, 2009).

The pro-thrombotic activity of the CREKA-nanoworms is selective for tumors. This is partly attributable to the selective accumulation of CREKA-NW, and the NW mixture, in tumor vessels. Both the peptide and the iron oxide component of the nanoparticles are responsible for the thrombotic activity, as other types of nanoparticles coated with CREKA and the free CREKA peptide lack this activity (Karmali, 2009; Peters, 2009), and iron oxide NW coated with tumor-homing peptides other than CREKA (CRKDKC and CGKRK) also do not cause clotting. Iron oxide nanoparticles are known to be procoagulant, and the affinity of CREKA for clotting products apparently enhances that activity. The NW, like other nanoparticles, non-specifically accumulate in the liver and spleen (Thorek, 2006). However, no clotting in the normal tissues of the tumor mice have been observed in this study, or in an earlier study that used a similar but less effective system (Simberg, 2007). Thus, the tumor environment, which is pro-coagulant (Abe, 1999; Dvorak, 1985) can play a role in bringing about the clotting in the tumor vessels. Atherosclerotic plaques tend to show subtle spontaneous clotting (Peters 2009; Smith 1993). Thus, the presence of atherosclerosis could be a limitation in the clinical application of the CREKA technology.

The potential of peptides as drug candidates is limited by poor pharmacokinetics, which includes rapid elimination from the circulation through filtration into the urine and susceptibility to proteolysis. Elimination into the urine is not a problem with peptides coated onto a nanoparticle, but the results do demonstrate the importance of proteolysis. Because each nanoparticle is coated with multiple peptides, one might expect the nanoparticle coating to tolerate some proteolysis without significant loss of activity. The results indicate that this is not the case; protecting the peptide against proteolytic cleavage by incorporating non-coded amino acids substantially improved the tumor-homing efficiency and increased the blockade of tumor vessels. Direct measurement of the stability of the peptides in vivo supported the conclusion that increased peptide stability is responsible, at least partially, for the improved characteristics of the methylated CREKA analogs. If extended to other peptide-coated nanoparticles, this result could have significant implications for the design of effective nanoparticle therapies.

Disclosed herein is anti-tumor activity of the system against two orthotropic prostate cancer xenograft tumors, 22Rv-1 and LAPC9. It is likely that other tumor types can be similarly targeted, as other types of tumors have been shown to be targeted by the CREKA system (Simberg, 2007). The efficiency of the combined CREKA-NW strongly correlated with the degree of tumor vessel blockade achieved with the various treatments. CR(NMe)EKA-PEG-NW caused 30% reduction in tumor blood flow, as documented by CEUS, and produced a modest reduction in tumor size. The CRKDKC-PEG-NW and CR(NMe)EKA-PEG-NW combination blocked 70% of tumor blood flow and gave a strong reduction in tumor size, as well as extended survival of the animals. Significantly, these results were obtained by utilizing only the inherent properties of the NW, which also allowed imaging of the tumors. Adding a drug to the particles can further enhance the utility of this theranostic nanosystem.

REFERENCES

1. Desai N, Trieu V, Yao Z, Louie L, Ci S, Yang A, Tao C, De T, Beals B, Dykes D, Noker P, Yao R, Labao E, Hawkins M, Soon-Shiong P (2006) *Clin Cancer Res* 12: 1317-1324.
2. Weissleder R, Bogdanov A, Jr, Neuwelt E A, Papisov M (1995) *Advanced Drug Delivery Reviews* 16: 321-334.
3. Sinek J, Frieboes H, Zheng X, Cristini V (2004) *Biomed Microdevices* 6: 297-309.
4. Boucher Y, Baxter L T, Jain, R K (1990) *Cancer Res* 50: 4478-4484.
5. Hoffman J A, Giraudo E, Singh M, Zhang L, Inoue M, Porkka K, Hanahan D, Ruoslahti E (2003) *Cancer Cell* 4: 383-391.
6. Oh P, Li Y, Yu J, Durr E, Krasinska K M, Carver L A, Testa J E, Schnitzer J E (2004) *Nature* 429: 629-635.
7. Ruoslahti, E (2002) *Nat Rev Cancer* 2: 83-90.
8. DeNardo S J, DeNardo G L, Miers L A, Natarajan A, Foreman A R, Gruettner C, Adamson G N, Ivkov R (2005) *Clin Cancer Res* 11: 7087s-7092s.
9. Akerman M E, Chan W C, Laakkonen P, Bhatia S N, Ruoslahti E (2002) *Proc Natl Acad Sci USA* 99: 12617-12621.
10. Cai W, Shin D W, Chen K, Gheysens O, Cao Q, Wang S X, Gambhir S S, Chen X (2006) *Nano Lett* 6: 669-676.
11. Pasqualini R, Ruoslahti E (1996) *Nature* 380: 364-366.
12. Hutchinson J N, Muller W J (2000) *Oncogene* 19: 6130-6137.
13. Dvorak H F, Senger D R, Dvorak A M, Harvey V S, McDonagh J (1985) *Science* 227: 1059-1061.
14. Abe K, Shoji M, Chen J, Bierhaus A, Danave I, Micko C, Casper K, Dillehay D L, Nawroth P P, Rickles F R (1999) *Proc Natl Acad Sci USA* 96: 8663-8668.
15. Pilch J, Brown D M, Komatsu M, Jarvinen T A, Yang M, Peters D, Hoffman R M, Ruoslahti E (2006) *Proc Natl Acad Sci USA* 103: 2800-2804.
16. Jung C W, Jacobs P (1995) *Magn Reson Imaging* 13: 661-674.
17. Jung, C W (1995) *Magn Reson Imaging* 13: 675-691.
18. Weissleder R, Stark, D D, Engelstad B L, Bacon B R, Compton C C, White D L, Jacobs P, Lewis J (1989) *AJR Am J Roentgenol* 152: 167-173.
19. Van Rooijen N, Sanders A (1994) *J Immunol Methods* 174: 83-93.
20. Moghimi S M, Hunter A C, Murray J C (2001) *Pharmacol Rev* 53: 283-318.
21. Moore A, Weissleder R, Bogdanov A, Jr (1997) *J Magn Reson Imaging* 7: 1140-1145.
22. Souhami R L, Patel H M, Ryman B E (1981) *Biochim Biophys Acta* 674: 354-371.
23. Fernandez-Urrusuno R, Fattal E, Rodrigues J M, Jr, Feger J, Bedossa P, Couvreur P (1996) *J Biomed Mater Res* 31: 401-408.
24. Radomski A, Jurasz P, Alonso-Escolano D, Drews M, Morandi M, Malinski T, Radomski M W (2005) *Br J Pharmacol* 146: 882-93.

25. Khandoga A, Stampfl A, Takenaka S, Schulz H, Radykewicz R, Kreyling W, Krombach F (2004) *Circulation* 109: 1320-1325.
26. Van der Heyde H C, Gramaglia I, Sun G, Woods C (2005) *Blood* 105: 1956-1963.
27. Gorbet M B, Sefton M V (2004) *Biomaterials* 25: 5681-5703.
28. Boccaccio C, Sabatino G, Medico E, Girolami F, Follenzi A, Reato G, Sottile A, Naldini L, Comoglio P M (2005) *Nature* 434: 396-400.
29. Huang X, Molema G, King S, Watkins L, Edgington T S, Thorpe P E (1997) *Science* 275: 547-550.
30. El-Sheikh A, Borgstrom P, Bhattacharjee G, Belting M, Edgington T S (2005) *Cancer Res* 65: 11109-11117.
31. Hutchinson J N, Muller W J (2000) *Oncogene* 19: 6130-6137.
32. Laakkonen P, Porkka K, Hoffman J A, Ruoslahti E (2002) *Nat Med* 8: 751-755.
33. Laakkonen P, Akerman M E, Biliran H, Yang M, Ferrer F, Karpanen T, Hoffman R M, Ruoslahti E (2004) *Proc Natl Acad Sci USA* 101: 9381-9386.
34. Suh T T, Holmback K, Jensen N J, Daugherty C C, Small K, Simon D I, Potter S, Degen J L (1995) *Genes Dev* 9: 2020-2033.
35. Van Rooijen N, Sanders A (1994) *J Immunol Methods* 174: 83-93.
36. Park, J-H., von Maltzahn, G., Zhang, L., Derfus, A. M., Simberg, D., Harris, T. J., Bhatia, S, N., Ruoslahti, E., Sailor, M. J. Systematic Surface Engineering of Magnetic Nanoworms for in vivo Tumor Targeting. Small, 5(6):694-700 (2009).
37. Simberg, D., Duza T., Park, J. H., Essler M., Pilch, J., Zhang, L., Derfus A. M., Yang M., Hoffman R. M. Bhatia S., Sailor, M. J., and Ruoslahti, E. Biomimetic amplification of nanoparticle homing to tumors. Proc. Natl. Acad. Sci. USA 104: 932-936 (2007).

| | Sequences |
|---|---|
| SEQ ID NO: 1 | CREKA |
| SEQ ID NO: 2 | CGLIIQKNEC |
| SEQ ID NO: 3 | CNAGESSKNC |
| SEQ ID NO: 4 | CXXXXXXXC, where C is cysteine and X is any amino acid |
| SEQ ID NO: 5 | CRKDKC |
| SEQ ID NO: 6 | CARSKNKDC |
| SEQ ID NO: 7 | CGKRK |
| SEQ ID NO: 8 | C(NMe)REKA |
| SEQ ID NO: 9 | CR(NMe)EKA |
| SEQ ID NO: 10 | CR(CMe)EKA |
| SEQ ID NO: 11 | CRE(NMe)KA |
| SEQ ID NO: 12 | CRE(CMe)KA |
| SEQ ID NO: 13 | CR(NMe)E(NMe)KA |

We claim:

1. A composition comprising a surface molecule selected from the group consisting of an iron oxide nanoworm, an iron oxide nanoparticle, an albumin nanoparticle, a liposome, a microparticle, and a fluorocarbon microbubble and at least one clot-binding compound, wherein the clot-binding compound comprises an amino acid sequence selected from the group consisting of C(NMe)REKA (SEQ ID NO:8), CR(NMe)EKA (SEQ ID NO:9), CR(CMe)EKA (SEQ ID NO:10), CRE(NMe)KA (SEQ ID NO:11), CRE(CMe)KA (SEQ ID NO:12), and CR(NMe)E(NMe)KA (SEQ ID NO: 13) and selectively binds to clotted plasma protein, wherein the composition causes clotting and amplifies the accumulation of the composition in tumors, wherein the clot-binding compound enhances the clotting in tumors compared to its unmodified derivative.

2. The composition of claim 1, wherein the clot-binding compound consists of an amino acid sequence selected from the group consisting of C(NMe)REKA (SEQ ID NO:8), CR(NMe)EKA (SEQ ID NO:9), CR(CMe)EKA (SEQ ID NO:10), CRE(NMe)KA (SEQ ID NO:11), CRE(CMe)KA (SEQ ID NO:12), and CR(NMe)E(NMe)KA (SEQ ID NO: 13).

3. The composition of claim 1, wherein the amino acid sequence is selected from the group consisting of CR(NMe)EKA (SEQ ID NO:9), CRE(CMe)KA (SEQ ID NO:11), and CR(NMe)E(NMe)KA (SEQ ID NO:13).

4. The composition of claim 1, further comprising a plurality of clot-binding compounds, each of the plurality of clot-binding compounds comprising an amino acid sequence selected from the group consisting of C(NMe)REKA (SEQ ID NO:8), CR(NMe)EKA (SEQ ID NO:9), CR(CMe)EKA (SEQ ID NO:10), CRE(NMe)KA (SEQ ID NO:11), CRE(CMe)KA (SEQ ID NO:12), and CR(NMe)E(NMe)KA (SEQ ID NO: 13), wherein the clot-binding compounds selectively bind to clotted plasma protein, wherein the plurality of clot-binding compounds causes clotting and amplifies the accumulation of the composition in tumors.

5. The composition of claim 4, wherein the each of the plurality of clot-binding compounds consists of an amino acid sequence selected from the group consisting of C(NMe)REKA (SEQ ID NO:8), CR(NMe)EKA (SEQ ID NO:9), CR(CMe)EKA (SEQ ID NO:10), CRE(NMe)KA (SEQ ID NO:11), CRE(CMe)KA (SEQ ID NO:12), and CR(NMe)E(NMe)KA (SEQ ID NO: 13).

6. The composition of claim 1, further comprising one or more tumor-homing compounds.

7. The composition of claim 6, wherein one or more of the tumor-homing compounds comprises an amino acid segment.

8. The composition of claim 7, wherein one or more of the amino acid segments of the tumor-homing compounds comprises the amino acid sequence CRKDKC (SEQ ID NO:5) or the amino acid sequence CGKRK (SEQ ID NO:7).

9. The composition of claim 6, wherein one or more of the tumor-homing compounds is thrombogenic.

10. The composition of claim 1, wherein the composition binds inside tumor blood vessels.

11. The composition of claim 10, wherein the composition reduces tumor growth.

12. The composition of claim 1, wherein the composition comprises at least 100 clot-binding compounds.

13. The composition of claim 12, wherein the composition comprises at least 1000 clot-binding compounds.

14. The composition of claim 13, wherein the composition comprises at least 10,000 clot-binding compounds.

15. The composition of claim 1, further comprising one or more moieties.

16. The composition of claim 15, wherein the moieties are independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, an image contrast agent, a fluorophore, fluorescein, rhodamine, a radionuclide, indium-Ill, technetium-99, carbon-11, and carbon-13.

17. The composition of claim 15, wherein at least one of the moieties is a therapeutic agent.

18. The composition of claim 17, wherein the therapeutic agent is a paclitaxel albumin-stabilized nanoparticle formulation.

19. The composition of claim 17, wherein the therapeutic agent is paclitaxel.

20. The composition of claim 17, wherein the therapeutic agent is taxol.

21. The composition of any claim 15, wherein at least one of the moieties is thrombogenic.

22. The composition of claim 15, wherein at least one of the moieties is not a clot-binding compound.

23. The composition of claim 15, wherein none of the moieties are clot-binding compounds.

24. The composition of claim 15, wherein at least one of the moieties is a homing compound, wherein the homing compound is not a clot-binding compound.

25. The composition of claims 15, wherein at least one of the moieties is a detectable agent.

26. The composition of claim 25, wherein the detectable agent is FAM.

27. The composition of claim 1, wherein the composition comprises a sufficient number and composition of clot-binding compounds such that the composition causes clotting and amplifies the accumulation of the composition in tumors.

28. The composition of claim 27, wherein sufficiency of the number and composition of clot-binding compounds is determined by assessing clotting and amplification of the accumulation of the composition in tumors in a non-human animal.

29. The composition of claim 1, wherein the composition comprises a sufficient density and composition of clot-binding compounds such that the composition causes clotting and amplifies the accumulation of the composition in tumors.

30. The composition of claim 29, wherein sufficiency of the density and composition of clot-binding compounds is determined by assessing clotting and amplification of the accumulation of the composition in tumors in a non-human animal.

31. The composition of claim 1, wherein the surface molecule is thrombogenic.

32. The composition of claim 1, wherein the modified clot-binding compound is thrombogenic.

33. A method comprising administering to a subject the composition of claim 1, wherein the composition selectively homes to clotted plasma protein, wherein the composition causes clotting and amplifies the accumulation of the composition at the site of the clotted plasma protein.

34. The method of claim 33, wherein the composition selectively homes to tumor vasculature, wound sites, or both.

35. The method of claim 33, wherein the composition has a therapeutic effect.

36. The method of claim 35, wherein the therapeutic effect is a slowing in the increase of or a reduction of tumor burden.

37. The method of claim 35, wherein the therapeutic effect is a slowing of the increase of or reduction of tumor size.

38. The method of claim 35, wherein the therapeutic effect is a reduction or blocking of blood circulation in a tumor.

39. The method of claim 35, wherein the therapeutic effect is a reduction or cessation of bleeding at a wound site.

40. The method of claim 35, wherein the therapeutic effect is a decrease in the time for bleeding to stop at a wound site.

41. The method of claim 35, wherein the therapeutic effect comprises a reduction in inflammation, an increase in speed of wound healing, reduction in amounts of scar tissue, decrease in pain, decrease in swelling, decrease in necrosis, or a combination thereof.

42. The method of claim 33, wherein the clotting has a therapeutic effect.

43. The method of claim 33, wherein the subject has one or more sites to be targeted, wherein the composition homes to one or more of the sites to be targeted.

44. The method of claim 33, wherein the subject has a tumor, wherein the composition has a therapeutic effect on the tumor.

45. A method comprising administering to a subject a plurality of different compositions, wherein the plurality of different compositions each comprise a composition of claim 1, wherein the compositions selectively home to clotted plasma protein, wherein the compositions cause clotting and amplifies the accumulation of the compositions at the site of the clotted plasma protein.

46. A method comprising administering to a subject a plurality of different compositions, wherein at least one of the plurality of different compositions comprises a composition of claim 1, wherein at least one of the compositions selectively homes to clotted plasma protein, wherein at least one of the compositions causes clotting and amplifies the accumulation of the composition at the site of the clotted plasma protein.

47. The method of claim 46, wherein each of the at least one of the plurality of different compositions selectively homes to clotted plasma protein, wherein each of the at least one of the plurality of compositions causes clotting and amplifies the accumulation of the compositions at the site of the clotted plasma protein.

48. The method of claim 46, wherein at least one of the plurality of different compositions comprises a surface molecule and at least one unmodified clot-binding compound, wherein the surface molecule is selected from the group consisting of an iron oxide nanoworm, an iron oxide nanoparticle, an albumin nanoparticle, a liposome, a microparticle, and a fluorocarbon microbubble and the unmodified clot-binding compound selectively binds to clotted plasma protein.

49. The method of claim 46, wherein at least one of the plurality of different compositions comprises a surface molecule and at least one homing compound, wherein the surface molecule is selected from the group consisting of an iron oxide nanoworm, an iron oxide nanoparticle, an albumin nanoparticle, a liposome, a microparticle, and a fluorocarbon microbubble and the homing compound is not a clot-binding compound.

50. The method of claim 49, wherein the homing compound selectively binds to tumor vasculature.

51. The method of claim 49, wherein the homing compound is a tumor-homing compound.

52. The method of claim 51, wherein the tumor-homing compound comprises an amino acid segment.

53. The method of claim 52, wherein the amino acid segment of the tumor-homing compound comprises the amino acid sequence CRKDKC (SEQ ID NO:5) or the amino acid sequence CGKRK (SEQ ID NO:7).

54. The method of claim 49, wherein at least two of the plurality of different compositions differ in the homing compounds of which the compositions are comprised.

55. A method comprising administering to a subject a plurality of different compositions, wherein at least one of the plurality of different compositions comprises a composition of claim 1, wherein at least one of the plurality of different compositions comprises a surface molecule selected from the group consisting of an iron oxide nanoworm, an iron oxide nanoparticle, an albumin nanoparticle, a liposome, a microparticle, and a fluorocarbon microbubble and at least one unmodified clot-binding compound, wherein the unmodified clot-binding compound selectively binds to clotted plasma protein, and wherein at least one of the plurality of different compositions comprises a surface molecule and at least one homing compound, wherein the homing compound is not a clot-binding compound.

56. The method of claim 45, wherein at least two of the plurality of different compositions differ in the clot-binding compounds of which the compositions are comprised.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: chemically synthesized; homing peptide
<220> FEATURE:
<221> NAME/KEY: peptide
<222> LOCATION: (1)..(5)

<400> SEQUENCE: 1

Cys Arg Glu Lys Ala
1               5

<210> SEQ ID NO 2
<211> LENGTH: 10
<212> TYPE: PRT
<213> ORGANISM: Artificial Sequence
<220> FEATURE:
<223> OTHER INFORMATION: chemically synthesized; clot binding peptide
<220> FEATURE:
<221> NAME/KEY: peptide
<222> LOCATION: (1)..(10)

<400> SEQUENCE: 2

Cys Gly Leu Ile Ile Gln Lys Asn Glu Cys
1               5                   10

<210> SEQ ID NO 3
<211> LENGTH: 10
```

```
<212> TYPE: PRT
<213> ORGANISM: Artificial Sequence
<220> FEATURE:
<223> OTHER INFORMATION: chemically synthesized; clot binding peptide
<220> FEATURE:
<221> NAME/KEY: peptide
<222> LOCATION: (1)..(10)

<400> SEQUENCE: 3

Cys Asn Ala Gly Glu Ser Ser Lys Asn Cys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: chemically synthesized; general structural
      sequence
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid

<400> SEQUENCE: 4

Cys Xaa Xaa Xaa Xaa Xaa Xaa Xaa Cys
1               5

<210> SEQ ID NO 5
<211> LENGTH: 6
<212> TYPE: PRT
<213> ORGANISM: Artificial Sequence
<220> FEATURE:
<223> OTHER INFORMATION: chemically synthesized; tumor homing peptide
<220> FEATURE:
<221> NAME/KEY: peptide
<222> LOCATION: (1)..(6)

<400> SEQUENCE: 5

Cys Arg Lys Asp Lys Cys
1               5

<210> SEQ ID NO 6
<211> LENGTH: 9
<212> TYPE: PRT
<213> ORGANISM: Artificial Sequence
<220> FEATURE:
<223> OTHER INFORMATION: chemically synthesized; clot binding peptide
<220> FEATURE:
```

```
<221> NAME/KEY: peptide
<222> LOCATION: (1)..(9)

<400> SEQUENCE: 6

Cys Ala Arg Ser Lys Asn Lys Asp Cys
1               5

<210> SEQ ID NO 7
<211> LENGTH: 5
<212> TYPE: PRT
<213> ORGANISM: Artificial Sequence
<220> FEATURE:
<223> OTHER INFORMATION: chemically synthesized; tumor homing peptide
<220> FEATURE:
<221> NAME/KEY: peptide
<222> LOCATION: (1)..(5)

<400> SEQUENCE: 7

Cys Gly Lys Arg Lys
1               5

<210> SEQ ID NO 8
<211> LENGTH: 5
<212> TYPE: PRT
<213> ORGANISM: Artificial Sequence
<220> FEATURE:
<223> OTHER INFORMATION: chemically synthesized; homing peptide
<220> FEATURE:
<221> NAME/KEY: PEPTIDE
<222> LOCATION: (1)..(5)
<223> OTHER INFORMATION: C is N-methylated

<400> SEQUENCE: 8

Cys Arg Glu Lys Ala
1               5

<210> SEQ ID NO 9
<211> LENGTH: 5
<212> TYPE: PRT
<213> ORGANISM: Artificial Sequence
<220> FEATURE:
<223> OTHER INFORMATION: chemically synthesized; homing peptide
<220> FEATURE:
<221> NAME/KEY: peptide
<222> LOCATION: (1)..(5)
<223> OTHER INFORMATION: R is N-methylated

<400> SEQUENCE: 9

Cys Arg Glu Lys Ala
1               5

<210> SEQ ID NO 10
<211> LENGTH: 5
<212> TYPE: PRT
<213> ORGANISM: Artificial Sequence
<220> FEATURE:
<223> OTHER INFORMATION: chemically synthesized; homing peptide
<220> FEATURE:
<221> NAME/KEY: peptide
<222> LOCATION: (1)..(5)
<223> OTHER INFORMATION: R is C-methylated

<400> SEQUENCE: 10

Cys Arg Glu Lys Ala
1               5

<210> SEQ ID NO 11
<211> LENGTH: 5
<212> TYPE: PRT
```

```
<213> ORGANISM: Artificial Sequence
<220> FEATURE:
<223> OTHER INFORMATION: chemically synthesized; homing peptide
<220> FEATURE:
<221> NAME/KEY: peptide
<222> LOCATION: (1)..(5)
<223> OTHER INFORMATION: E is N-methylated

<400> SEQUENCE: 11

Cys Arg Glu Lys Ala
1               5

<210> SEQ ID NO 12
<211> LENGTH: 5
<212> TYPE: PRT
<213> ORGANISM: Artificial Sequence
<220> FEATURE:
<223> OTHER INFORMATION: chemically synthesized; homing peptide
<220> FEATURE:
<221> NAME/KEY: peptide
<222> LOCATION: (1)..(5)
<223> OTHER INFORMATION: E is C-methylated

<400> SEQUENCE: 12

Cys Arg Glu Lys Ala
1               5

<210> SEQ ID NO 13
<211> LENGTH: 5
<212> TYPE: PRT
<213> ORGANISM: Artificial Sequence
<220> FEATURE:
<223> OTHER INFORMATION: chemically synthesized; homing peptide
<220> FEATURE:
<221> NAME/KEY: peptide
<222> LOCATION: (1)..(5)
<223> OTHER INFORMATION: R is N-methylated; E is N-methylated

<400> SEQUENCE: 13

Cys Arg Glu Lys Ala
1               5
```